(12) United States Patent
Duesterhoft et al.

(10) Patent No.: US 9,084,530 B2
(45) Date of Patent: Jul. 21, 2015

(54) COMPUTATIONAL METHODS AND SYSTEMS FOR REPORTING INFORMATION REGARDING APPURTENANCES TO WOUND DRESSINGS

(75) Inventors: Paul Duesterhoft, Issaquah, WA (US); Nicholas Dykstra, Seattle, WA (US); Daniel Hawkins, Bellevue, WA (US); Roderick A. Hyde, Redmond, WA (US); Jordin T. Kare, Seattle, WA (US); Eric C. Leuthardt, St. Louis, MO (US); Elizabeth L. Schubert, Bellevue, WA (US); Clarence T. Tegreene, Bellevue, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 340 days.

(21) Appl. No.: 13/445,220

(22) Filed: Apr. 12, 2012

(65) Prior Publication Data

US 2013/0271278 A1    Oct. 17, 2013

Related U.S. Application Data

(63) Continuation-in-part of application No. 13/445,174, filed on Apr. 12, 2012.

(51) Int. Cl.
  *G08B 1/08* (2006.01)
  *A61B 5/00* (2006.01)
  *A61M 1/00* (2006.01)
  *A61B 5/145* (2006.01)

(52) U.S. Cl.
  CPC ............. *A61B 5/002* (2013.01); *A61B 5/0022* (2013.01); *A61B 5/445* (2013.01); *A61B 5/14539* (2013.01); *A61M 1/0088* (2013.01)

(58) Field of Classification Search
  None
  See application file for complete search history.

(56) References Cited

U.S. PATENT DOCUMENTS

| 4,384,288 A | 5/1983 | Walton |
| 5,704,352 A | 1/1998 | Tremblay et al. |
| 5,904,671 A | 5/1999 | Navot et al. |

(Continued)

FOREIGN PATENT DOCUMENTS

| EP | 0 430 608 A1 | 6/1991 |
| WO | WO 00/08203 | 2/2000 |

(Continued)

OTHER PUBLICATIONS

U.S. Appl. No. 13/491,677, Duesterhoft et al.

(Continued)

*Primary Examiner* — John A. Tweel, Jr.
*Assistant Examiner* — Brian Wilson
(74) *Attorney, Agent, or Firm* — Dorsey & Whitney LLP

(57) ABSTRACT

Computational systems and methods for reporting information regarding appurtenances to wound dressings are described. A system can include an appurtenance to a wound dressing, including a substrate, a transmission unit, a selectively activated switch, and a projection of a size and shape to extend into an interior region of a wound dressing and configured to sample a fluid associated with a wound; a local unit, including a receiver configured to receive signals from the transmission unit, a transmitter configured to send signals to the transmission unit, a processor, non-volatile memory, and a power source; and a central assembly, including a processor, a receiver configured to receive signals from the local unit, and at least one user interface.

47 Claims, 47 Drawing Sheets

(56) References Cited

U.S. PATENT DOCUMENTS

| | | | |
|---|---|---|---|
| 5,912,114 | A | 6/1999 | Hutchinson et al. |
| 5,939,205 | A | 8/1999 | Yokoyama et al. |
| 6,037,879 | A | 3/2000 | Tuttle |
| 6,270,455 | B1 | 8/2001 | Brown |
| 6,283,938 | B1 | 9/2001 | McConnell |
| 6,348,640 | B1 | 2/2002 | Navot et al. |
| 6,420,622 | B1 | 7/2002 | Johnston et al. |
| 6,693,513 | B2 | 2/2004 | Tuttle |
| 6,863,220 | B2 | 3/2005 | Selker |
| 6,889,165 | B2 | 5/2005 | Lind et al. |
| 6,963,772 | B2 | 11/2005 | Bloom et al. |
| 7,030,764 | B2 | 4/2006 | Smith et al. |
| 7,055,754 | B2 | 6/2006 | Forster |
| 7,215,976 | B2 | 5/2007 | Brideglall |
| 7,297,112 | B2 | 11/2007 | Zhou et al. |
| 7,372,780 | B1 | 5/2008 | Braunberger |
| 7,411,505 | B2 | 8/2008 | Smith et al. |
| 7,446,660 | B2 | 11/2008 | Posamentier |
| 7,479,886 | B2 | 1/2009 | Burr |
| 7,507,675 | B2 | 3/2009 | Zuilhof et al. |
| 7,612,424 | B1 | 11/2009 | Espinosa et al. |
| 7,666,151 | B2 | 2/2010 | Sullivan et al. |
| 7,667,606 | B2 | 2/2010 | Packert et al. |
| 7,703,334 | B2 | 4/2010 | Cochran |
| 7,724,136 | B2 | 5/2010 | Posamentier |
| 7,794,925 | B2 | 9/2010 | Cullen |
| 7,813,226 | B2 | 10/2010 | Braunberger |
| 7,825,776 | B2 | 11/2010 | Smith et al. |
| 7,914,867 | B2 | 3/2011 | Mori et al. |
| 7,945,302 | B2 | 5/2011 | McAdams |
| 7,951,605 | B2 | 5/2011 | Pitner et al. |
| 7,964,390 | B2 | 6/2011 | Rozakis et al. |
| 7,986,235 | B2 | 7/2011 | Posamentier |
| 8,014,234 | B2 | 9/2011 | Braunberger |
| 2003/0199783 | A1 | 10/2003 | Bloom et al. |
| 2003/0216663 | A1 | 11/2003 | Jersey-Willuhn et al. |
| 2006/0036145 | A1 | 2/2006 | Brister et al. |
| 2006/0047218 | A1 | 3/2006 | Bloom et al. |
| 2007/0171076 | A1 | 7/2007 | Stevens et al. |
| 2007/0204691 | A1* | 9/2007 | Bogner et al. ............... 73/432.1 |
| 2007/0231380 | A1 | 10/2007 | Shah et al. |
| 2007/0247316 | A1 | 10/2007 | Wildman et al. |
| 2007/0252712 | A1 | 11/2007 | Allen et al. |
| 2007/0269851 | A1 | 11/2007 | Sanders et al. |
| 2008/0166397 | A1 | 7/2008 | Trotter et al. |
| 2009/0167495 | A1 | 7/2009 | Smith et al. |
| 2009/0192369 | A1 | 7/2009 | Say et al. |
| 2009/0209883 | A1 | 8/2009 | Higgins et al. |
| 2009/0243813 | A1 | 10/2009 | Smith et al. |
| 2009/0299161 | A1 | 12/2009 | Cullen et al. |
| 2010/0022990 | A1 | 1/2010 | Karpowicz et al. |
| 2010/0030167 | A1 | 2/2010 | Thirstrup et al. |
| 2010/0100061 | A1 | 4/2010 | Odland |
| 2010/0166694 | A1 | 7/2010 | Stephens et al. |
| 2010/0204606 | A1 | 8/2010 | Kim et al. |
| 2010/0331634 | A1 | 12/2010 | Müller et al. |
| 2011/0015591 | A1 | 1/2011 | Hanson et al. |
| 2011/0054340 | A1* | 3/2011 | Russ et al. .................... 600/529 |
| 2011/0082356 | A1 | 4/2011 | Yang et al. |
| 2011/0092927 | A1 | 4/2011 | Wilkes et al. |
| 2011/0105854 | A1 | 5/2011 | Kiani et al. |
| 2011/0140703 | A1 | 6/2011 | Chiao et al. |
| 2011/0178375 | A1* | 7/2011 | Forster .......................... 600/301 |
| 2011/0213559 | A1 | 9/2011 | Pollack et al. |
| 2012/0010099 | A1 | 1/2012 | Stephens et al. |
| 2012/0109034 | A1* | 5/2012 | Locke et al. .................... 602/42 |
| 2013/0261409 | A1* | 10/2013 | Pathak et al. ................. 600/301 |
| 2013/0304006 | A1* | 11/2013 | Toth .............................. 604/319 |

FOREIGN PATENT DOCUMENTS

| | | |
|---|---|---|
| WO | WO 03/040406 A2 | 5/2003 |
| WO | WO 2005/009328 A1 | 2/2005 |
| WO | WO 2007/130239 A1 | 11/2007 |

OTHER PUBLICATIONS

U.S. Appl. No. 14/445,174, Duesterhoft et al.

"Body-fluid battery"; Science News; Sep. 10, 2005; pp. 1-2; located at http://findarticles.com/p/articles/mi_m1200/is_11_168/ai_n15674798/; Science Service, Inc. and Gale Group.

Goodisman, Jerry; "Observations on Lemon Cells"; Journal of Chemical Education; Apr. 2001; pp. 516-518; vol. 78, No. 4.

Huang et al.; "Development of an $IrO_x$ Micro pH Sensor Array on Flexible Polymer Substrate"; Nanosensors and Microsensors for Bio-Systems 2008, edited by Vijay K. Varadan, Proc. of SPIE, vol. 6931, 693104; 2008; pp. 1-9.

Huang et al.; "Investigation of Repeatability of Sol-Gel Iridium Oxide pH Sensor on Flexible Substrate"; Micro- and Nanotechnology: Materials, Processes, Packaging, and Systems IV, edited by Jung-Chih Chiao et al., Proc. of SPIE, vol. 7269, 726916; 2008; pp. 1-9.

Karthik MNS; "Could blood be used to power batteries?"; Feb. 2009; pp. 1-4; located at: http://hoowstuffworks.blogspot.com/2009/02/could-blood-be-used-to-power-batteries.html.

Lee et al.; "Water Activated Disposable and Long Shelf Life Microbatteries"; 2003; pp. 387-390; IEEE.

Löfgren et al.; "Low-power humidity sensor for RFID applications"; Multi-Material Micro Manufacture; 2008; 4 pages; Cardiff University.

Nature News; "A miniature biofuel cell operating in a physiological buffer"; Nature; Nov. 12, 2002; pp. 1-2; located at http://www.nature.com/news/2002/021112/full/news021111-1.html.

Pan et al.; "Development of the real-time pH sensing system for array sensors"; Sensors and Actuators B 108; 2005; pp. 870-876; Elsevier B.V.

Pushparaj et al.; "Flexible energy storage devices based on nanocomposite paper"; PNAS; Aug. 21, 2007; pp. 13574-13577; vol. 104, No. 34; The National Academy of Sciences of the USA.

Sammoura et al.; "Water-activated disposable and long shelf life microbatteries"; Sensors and Actuators A 111; 2004; pp. 79-86; Elsevier B.V.

Sidén et al.; "The 'Smart' Diaper Moisture Detection System"; IEEE MTT-S Digest, WE4B-3; 2004; pp. 659-662; IEEE.

University of Texas Arlington, Office of Technology Management; "Smart Wound Condition Monitoring pH Sensor Array on Flexible Substrate"; Technology Summary; printed on Apr. 12, 2012; pp. 1-2.

PCT International Search Report; International App. No. PCT/US13/36000; Jul. 5, 2013; pp. 1-3.

PCT International Search Report; International App. No. PCT/US2013/035993; Jun. 25, 2013; pp. 1-2.

U.S. Appl. No. 13/795,667, Duesterhoft et al.

Bluestein et al.; "Pressure Ulcers: Prevention, Evaluation, and Management"; American Family Physician; Nov. 15, 2008; pp. 1186-1194; vol. 78, No. 10; American Academy of Family Physicians.

Clay, Karen S.; "Preventing pressure ulcers in your facility: Karen S. Clay, RN, BSN, CWCN, presents a primer on how to protect frail residents—and avoid costly reprimands"; bearing a date of 2004; 14 pages; HCPro, Inc.

Dowd et al.; "Survey of bacterial diversity in chronic wounds using Pyrosequencing, DGGE, and full ribosome shotgun sequencing"; BMC Microbiology; bearing a date of 2008, published Mar. 6, 2008; pp. 1-15; vol. 8, No. 43; BioMed Central Ltd.

Grist et al.; "Optical Oxygen Sensors for Applications in Microfluidic Cell Culture"; Sensors; bearing a date of 2010, published Oct. 15, 2010; pp. 9286-9316; vol. 10; MDPI; Basel, Switzerland.

Abhisam; "RFID systems for pharmaceutical distributors to meet the new FDA regulations on drugs"; Discover the power of e-learning!; bearing a date of 2006; pp. 1-7; Abhisam Software.

Alien Technology; "Battery Assisted Passive Tags"; Alien Technology brochure; downloaded from the web Oct. 17, 2011; pp. 1-2; located at: http://www.alientechnology.com/docs/AT_DS_BAP.pdf; Alien Technology Corp.

Berggren et al.; "Capacitive Biosensors"; Electroanalysis; bearing a date of 2001; pp. 173-180; vol. 13, No. 3; Wiley-VCH Verlag GmbH.

Chawla et al.; "An Overview of Passive RFID"; IEEE Applications & Practice; Sep. 2007; pp. 11-17; IEEE.

(56) References Cited

OTHER PUBLICATIONS

Chen et al.; "A 2G-RFID-Based E-Healthcare System"; IEEE Wireless Communications; Feb. 2010; pp. 37-43; IEEE.
Chen et al.; "Ultrasonic Measurement System with Infrared Communication Technology"; Journal of Computers; Nov. 2011; pp. 2468-2475; vol. 6, No. 11; Academy Publisher.
Collier, Mark; "Recognition and management of wound infections"; World Wide Wounds; Jan. 2004; pp. 1-9.
Cui et al.; "Nanowire Nanosensors for Highly Sensitive and Selective Detection of Biological and Chemical Species"; Science; Aug. 17, 2001; pp. 1289-1292, and 1 cover page; vol. 293; American Association for the Advancement of Science.
Cutting et al.; "Criteria for identifying wound infection"; Journal of Wound Care; Jun. 1994; pp. 198-201; vol. 3, No. 4.
Fadlullah et al; "Indoor High-Bandwidth Optical Wireless Links for Sensor Networks"; Journal of Lightwave Technology; Nov. 1, 2010; pp. 3086-3094; vol. 28, No. 21; IEEE.
Finkenzeller, Klaus; "Fundamental Operating Principles" Chapter 3 of the RFID Handbook: Fundamentals and Applications in Contactless Smart Cards and Identification; bearing a date of 2003; pp. 29-59; John Wiley & Sons, Ltd.
Fisher et al.; "Tracking the social dimensions of RFID systems in hospitals"; International Journal of Medical Informatics; bearing a date of 2008; pp. 176-183; vol. 77; Elsevier Ireland Ltd.
Fisher, Jill A.; "Indoor Positioning and Digital Management: Emerging Surveillance Regimes in Hospitals"; Chapter 5 in T. Monahan (Ed), Surveillance and Security: Technological Politics and Power in Everyday Life; May 23, 2006; pp. 77-88; Routledge.
Frost & Sullivan; "Advances in Wound Healing Techniques"; Technical Insights; Publication D11A; bearing a date of 2008; pp. 1-118; Frost & Sullivan.
Frost & Sullivan; "An Overview of Ulceration Wounds"; Publication M4BB-54; Dec. 2009; pp. 1-77; Frost & Sullivan.
Frost & Sullivan; "U.S. Advanced Wound Care Market"; Publication N71A-54; Aug. 2010; pp. 1-90; Frost & Sullivan.
Gray, David; "Assessment, Diagnosis and Treatment of Infection"; Wounds UK; bearing a date of 2011; pp. 4-9; vol. 7, No. 2, supplement.
Ibridge Network; "pH Sensor Array on Flexible Substrate for Wound Care (UTA Ref. No. 08-21)"; Nov. 28, 2011; pp. 1-2; Kauffman Innovation Network, Inc.
Intel; "WISP: Wireless Identification and Sensing Platform"; Intel Labs Seattle; printed on Oct. 8, 2011; pp. 1-4; located at http://www.seattle.intel-research.net/WISP/.
Intelleflex; "Worldwide RFID UHF Map"; printed on Oct. 17, 2011; p. 1; located at: http://www.intelleflex.com/pdf/Worldwide_UHF_Chart.pdf ; Intelleflex Corporation.
Kavehrad, Mohsen; "Sustainable Energy-Efficient Wireless Applications Using Light"; IEEE Communications Magazine; Dec. 2010; pp. 66-73; IEEE.
Kelly-Quintos et al.; "Characterization of the Opsonic and Protective Activity Against *Staphylococcus aureus* of Fully Human Monoclonal Antibodies Specific for the Bacterial Surface Polysaccharide Poly-*N*-Acetylglucosamine"; Infection and Immunity; May 2006; pp. 2742-2750; vol. 74, No. 5; American Society for Microbiology.
Lim et al.; "A Micromechanical Biosensor with Interdigitated Capacitor Readout"; Proceedings of the 2011 IEEE/ICME International Conference on Complex Medical Engineering; May 22-25, 2011; pp. 42-46; IEEE.
McColl et al.; "Monitoring moisture without disturbing the wound dressing"; Wounds UK; bearing a date of 2009; pp. 94-96, and 98-99; vol. 5, No. 3.
Murata Manufacturing Co., Ltd.; "Piezoelectric Sound Components"; Cat. No. P37E-23; Nov. 2009; pp. 1-33, and two cover pages.
Murata Manufacturing Co., Ltd.; "Ultrasonic Sensor Application Manual"; Cat. No. S15E-5; Aug. 2009; pp. 1-3, and 2-14, and one supplemental page.
Ohno et al.; "Graphene Field-Effect Transistors for Label-Free Biological Sensors"; IEEE Sensors 2010 Conference Proceedings; Nov. 1-4, 2010; pp. 903-906; IEEE.
Pacific Northwest National Laboratory; "Juvenile Salmon Acoustic Telemetry System (JSATS) Acoustic Transmitters"; Mar. 2010; pp. 1-2.
Patauner et al.; "High Speed RFID/NFC at the Frequency of 13.56 MHz"; presented at the First International EURASIP Workshop on RFID Technology; Sep. 24-25, 2007; pp. 1-4.
Ruhanen et al.; "Sensor-enabled RFID tag handbook"; Building Radio Frequency Identification for the Global Environment; Jan. 2008; pp. 1-47; IST-2005-033546; European Commission.
Sample et al.; "A Capacitive Touch Interface for Passive RFID Tags"; IEEE International Conference on RFID; Apr. 27-28, 2009; pp. 103-109; IEEE.
Sample et al.; "Design of an RFID-Based Battery-Free Programmable Sensing Platform"; IEEE Transactions on Instrumentation and Measurement; Nov. 2008; pp. 2608-2615; vol. 57, No. 11; IEEE.
Sample et al.; "Photovoltaic Enhanced UHF RFID Tag Antennas for Dual Purpose Energy Harvesting"; 2011 International Conference on RFID; Apr. 12-14, 2011; pp. 146-153; IEEE.
Stevens et al.; "RuBee (IEEE 1902.1)—The Physics Behind, Real-Time, High Security Wireless Asset Visibility Networks in Harsh Environments"; Sep. 2010; retrieved from web Nov. 17, 2011; pp. 1-6; located at: http://www.rubee.com/White-SEC/RuBee-Security-080610.pdf.
Tehrani et al.; "Detection of Monoclonal Antibodies using Chemically Modified Graphite Substrates"; IEEE Sensors 2010 Conference Proceedings; Nov. 1-4, 2010; pp. 428-431; IEEE.
Visible Assets; "RuBee Technology, Real-Time Asset Visibility"; printed from web Nov. 17, 2011; pp. 1-3; located at: http://www.rubee.com/Techno/index.html ; Visible Assets.
Wang, Wencheng; "A Design Method of Ultrasonic Ranging System with High Accuracy"; Journal of Computational Information Systems; Jul. 2011; pp. 2444-2451; vol. 7, No. 7; Binary Information Press.
Yeager et al.; "Wirelessly-Charged UHF Tags for Sensor Data Collection"; 2008 IEEE International Conference on RFID; Apr. 16-17, 2008; pp. 320-327; IEEE.
U.S. Appl. No. 14/252,136, Duesterhoft et al.
U.S. Appl. No. 14/252,049, Allin et al.
DeHennis et al.; "A Wireless Microsystem for the Remote Sensing of Pressure, Temperature, and Relative Humidity"; Journal of Microelectromechanical Systems; Feb. 2005; pp. 12-22; vol. 14, No. 1; IEEE.
Mehmood et al.; "Applications of modern sensors and wireless technology in effective wound management"; Journal of Biomedical Materials Research B: Applied Biomaterials; bearing a date of Sep. 27, 2013; pp. 1-11; Wiley Periodicals, Inc.
U.S. Appl No. 14/675,792, Duesterhoft et al.

\* cited by examiner

FIG. 7
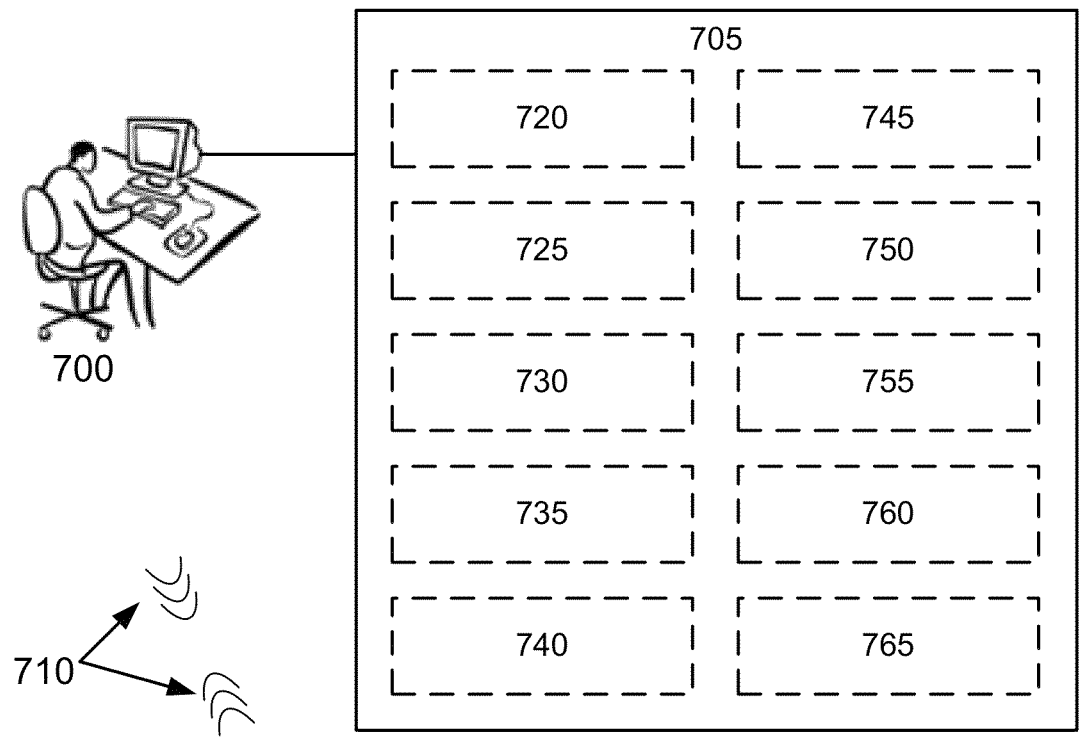
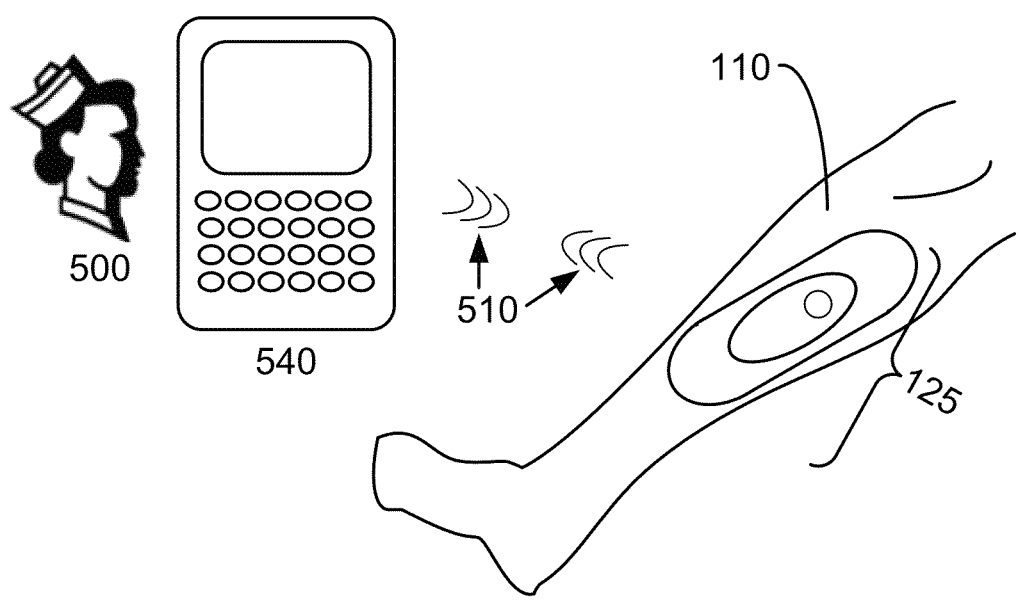

FIG. 39

| |
|---|
| 3910 Receiving a first transmission from a local unit, the first transmission including first information regarding an appurtenance attached to a wound dressing |
| 3915 Associating a first time point with the receipt of the first transmission |
| 3920 Associating wound dressing parameters with the received first information regarding the appurtenance |
| 3925 Determining, based on the associated wound dressing parameters and the received first information, a first status of the appurtenance |
| 3930 Determining, based on the determined first status of the appurtenance, a first response |
| 3935 Saving into memory as a record of the appurtenance the first time point, the received first information and the associated wound dressing parameters |
| 3940 Receiving a second transmission from the local unit, the second transmission including second information regarding the appurtenance attached to the wound dressing |
| 3945 Associating a second time point with the receipt of the second transmission |
| 3950 Associating the record of the appurtenance with the received second information regarding the appurtenance |
| 3955 Determining, based on the associated record and the received second information, a second status of the appurtenance |
| 3960 Determining, based on the determined second status of the appurtenance, a second response |
| 3965 Saving into memory with the record of the appurtenance the second time point and the received second information |

FIG. 42

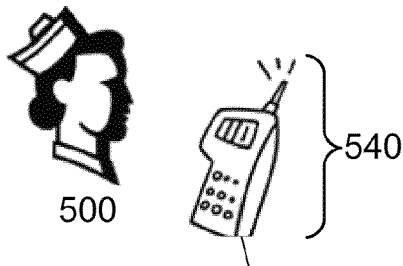

500  540

4200 Circuitry configured to monitor an appurtenance attached to a wound dressing 4210 Circuitry for transmitting a first signal configured to be received by an appurtenance attached to a wound dressing 4220 Circuitry for receiving a first signal from the appurtenance 4230 Circuitry for associating a first time point with the receipt of the first signal 4240 Circuitry for transmitting a second signal configured to be received by the appurtenance 4250 Circuitry for receiving a second signal from the appurtenance 4260 Circuitry for associating a second time point with the receipt of the second signal

FIG. 43

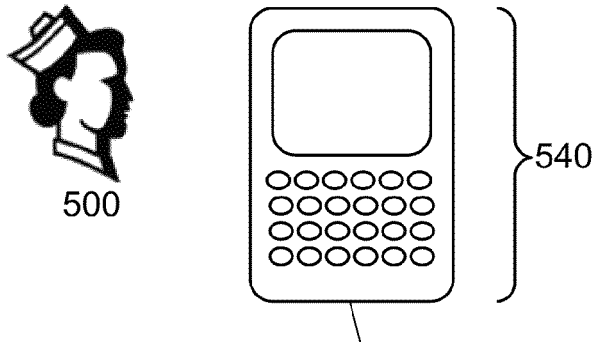

500  540

4300 Circuitry configured to monitor an appurtenance attached to a wound dressing 4310 Circuitry for transmitting a first signal from a local unit, the first signal configured to be received by an appurtenance attached to a wound dressing 4320 Circuitry for receiving a first signal from the appurtenance at the local unit 4330 Circuitry for transmitting information regarding the first signal from the local unit to a central assembly 4340 Circuitry for associating a first time point with the receipt of the first signal 4350 Circuitry for transmitting a second signal from the local unit, the second signal configured to be received by the appurtenance 4360 Circuitry for receiving a second signal from the appurtenance at the local unit 4370 Circuitry for transmitting information regarding the first signal from the local unit to a central assembly 4380 Circuitry for associating a second time point with the receipt of the second signal

FIG. 44

700

| |
|---|
| 4400 Circuitry configured for monitoring an appurtenance attached to a wound dressing |
| 4410 Circuitry for receiving a first transmission from a local unit, the first transmission including first information regarding an appurtenance attached to a wound dressing |
| 4415 Circuitry for associating a first time point with the receipt of the first transmission |
| 4420 Circuitry for associating wound dressing parameters with the received first information regarding the appurtenance |
| 4425 Circuitry for determining, based on the associated wound dressing parameters and the received first information, a first status of the appurtenance |
| 4430 Circuitry for determining, based on the determined first status of the appurtenance, a first response |
| 4435 Circuitry for saving into memory as a record of the appurtenance the first time point, the received first information and the associated wound dressing parameters |
| 4440 Circuitry for receiving a second transmission from the local unit, the second transmission including second information regarding the appurtenance attached to the wound dressing |
| 4445 Circuitry for associating a second time point with the receipt of the second transmission |
| 4450 Circuitry for associating the record of the appurtenance with the received second information regarding the appurtenance |
| 4455 Circuitry for determining, based on the associated record and the received second information, a second status of the appurtenance |
| 4460 Circuitry for determining, based on the determined second status of the appurtenance, a second response |
| 4465 Circuitry for saving into memory with the record of the appurtenance the second time point and the received second information |

FIG. 45

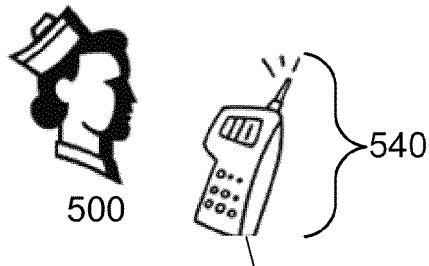

4500 A computer system configured to monitor an appurtenance attached to a wound dressing, the computer system including

| 4510 One or more instructions for transmitting a first signal configured to be received by an appurtenance attached to a wound dressing |

| 4520 One or more instructions for receiving a first signal from the appurtenance |

| 4530 One or more instructions for associating a first time point with the receipt of the first signal |

| 4540 One or more instructions for transmitting a second signal configured to be received by the appurtenance |

| 4550 One or more instructions for receiving a second signal from the appurtenance |

| 4560 One or more instructions for associating a second time point with the receipt of the second signal |

FIG. 46

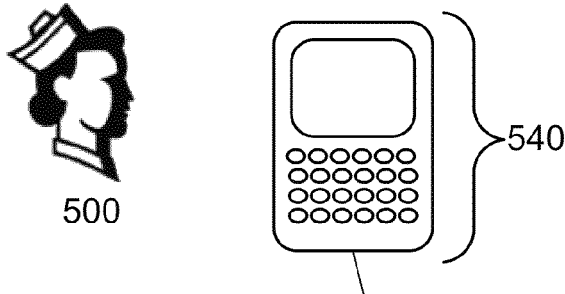

4600 A computer system configured to monitor an appurtenance attached to a wound dressing 4610 One or more instructions for transmitting a first signal from a local unit, the first signal configured to be received by an appurtenance attached to a wound dressing 4620 One or more instructions for receiving a first signal from the appurtenance at the local unit 4630 One or more instructions for transmitting information regarding the first signal from the local unit to a central assembly 4640 One or more instructions for associating a first time point with the receipt of the first signal 4650 One or more instructions for transmitting a second signal from the local unit, the second signal configured to be received by the appurtenance 4660 One or more instructions for receiving a second signal from the appurtenance at the local unit 4670 One or more instructions for transmitting information regarding the first signal from the local unit to a central assembly 4680 One or more instructions for associating a second time point with the receipt of the second signal

FIG. 47

700

4700 A computer system configured to monitor an appurtenance attached to a wound dressing 4710 One or more instructions for receiving a first transmission from a local unit, the first transmission including first information regarding an appurtenance attached to a wound dressing 4715 One or more instructions for associating a first time point with the receipt of the first transmission 4720 One or more instructions for associating wound dressing parameters with the received first information regarding the appurtenance 4725 One or more instructions for determining, based on the associated wound dressing parameters and the received first information, a first status of the appurtenance 4730 One or more instructions for determining, based on the determined first status of the appurtenance, a first response 4735 One or more instructions for saving into memory as a record of the appurtenance the first time point, the received first information and the associated wound dressing parameters 4740 One or more instructions for receiving a second transmission from the local unit, the second transmission including second information regarding the appurtenance attached to the wound dressing 4745 One or more instructions for associating a second time point with the receipt of the second transmission 4750 One or more instructions for associating the record of the appurtenance with the received second information regarding the appurtenance 4755 One or more instructions for determining, based on the associated record and the received second information, a second status of the appurtenance 4760 One or more instructions for determining, based on the determined second status of the appurtenance, a second response 4765 One or more instructions for saving into memory with the record of the appurtenance the second time point and the received second information

COMPUTATIONAL METHODS AND SYSTEMS FOR REPORTING INFORMATION REGARDING APPURTENANCES TO WOUND DRESSINGS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/445,174, entitled APPURTENANCES FOR REPORTING INFORMATION REGARDING WOUND DRESSINGS, naming Paul Duesterhoft, Nicholas Dykstra, Daniel Hawkins, Roderick A. Hyde, Jordin T. Kare, Eric C. Leuthardt, Elizabeth L. Schubert, Clarence T. Tegreene, and Lowell L. Wood, Jr. as inventors, filed 12 Apr. 2012, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

In one aspect, a system includes but is not limited to a system for monitoring a wound dressing, including: an appurtenance to a wound dressing, wherein the appurtenance includes one or more projections configured to be positioned into the wound dressing and configured to sample a fluid associated with a wound, a processor, and at least one transmitter operably attached to the processor; and a local unit including a receiver for the at least one transmitter, at least one processor operably attached to the receiver, and at least one communication unit operably attached to the processor. In one aspect, a system includes but is not limited to a system for monitoring a wound dressing, including: an appurtenance to a wound dressing, including a substrate, a transmission unit, a selectively activated switch, and a projection of a size and shape to extend into an interior region of a wound dressing; a local unit, including a receiver configured to receive signals from the transmission unit, a transmitter configured to send signals to the transmission unit, a processor, non-volatile memory, and a power source; and a central assembly, including a processor, a receiver configured to receive signals from the local unit, and at least one user interface. In one aspect, a system includes but is not limited to a system for monitoring a wound dressing, including: an appurtenance to a wound dressing, including a substrate, a transmission unit, a selectively activated switch, and a projection of a size and shape to extend into an interior region of a wound dressing and configured to sample a fluid associated with a wound; a local unit, including a receiver unit configured to receive signals from the transmission unit, a transmitter configured to send signals to the transmission unit, a processor, non-volatile memory, and a power source; a central assembly, including a processor, a receiver configured to receive signals from the local unit, a transmitter, and at least one user interface; and one or more user indicator devices including a receiver configured to receive signals from the central unit, a processor, non-volatile memory, and an indicator. In addition to the foregoing, other system aspects are described in the claims, drawings, and text forming a part of the present disclosure.

In one aspect, a method of monitoring an appurtenance attached to a wound dressing includes but is not limited to: transmitting a first signal configured to be received by an appurtenance attached to a wound dressing; receiving a first signal from the appurtenance; associating a first time point with the receipt of the first signal; transmitting a second signal configured to be received by the appurtenance; receiving a second signal from the appurtenance; and associating a second time point with the receipt of the second signal. In one aspect, a method of monitoring an appurtenance attached to a wound dressing includes but is not limited to: transmitting a first signal from a local unit, the first signal configured to be received by an appurtenance attached to a wound dressing; receiving a first signal from the appurtenance at the local unit; transmitting information regarding the first signal from the local unit to a central assembly; associating a first time point with the receipt of the first signal; transmitting a second signal from the local unit, the second signal configured to be received by the appurtenance; receiving a second signal from the appurtenance at the local unit; transmitting information regarding the first signal from the local unit to a central assembly; and associating a second time point with the receipt of the second signal. In one aspect, a method of monitoring an appurtenance attached to a wound dressing includes but is not limited to: receiving a first transmission from a local unit, the first transmission including first information regarding an appurtenance attached to a wound dressing; associating a first time point with the receipt of the first transmission; associating wound dressing parameters with the received first information regarding the appurtenance; determining, based on the associated wound dressing parameters and the received first information, a first status of the appurtenance; determining, based on the determined first status of the appurtenance, a first response; saving into memory as a record of the appurtenance the first time point, the received first information and the associated wound dressing parameters; receiving a second transmission from the local unit, the second transmission including second information regarding the appurtenance attached to the wound dressing; associating a second time point with the receipt of the second transmission; associating the record of the appurtenance with the received second information regarding the appurtenance; determining, based on the associated record and the received second information, a second status of the appurtenance; determining, based on the determined second status of the appurtenance, a second response; and saving into memory with the record of the appurtenance the second time point and the received second information. In addition to the foregoing, other method aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 7 is a schematic of an appurtenance to a wound dressing in communication with a local unit and a central assembly.

FIG. 38 is a flowchart displaying aspects of a method such as illustrated in

FIG. 26.

FIG. 39 is a flowchart of a method.

FIG. 42 illustrates a system including circuitry.

FIG. 43 shows a system including circuitry.

FIG. 44 illustrates a system including circuitry.

FIG. 45 shows a system including circuitry.

FIG. 46 illustrates a system including circuitry.

FIG. 47 shows a system including circuitry.

DETAILED DESCRIPTION

Figure 1:
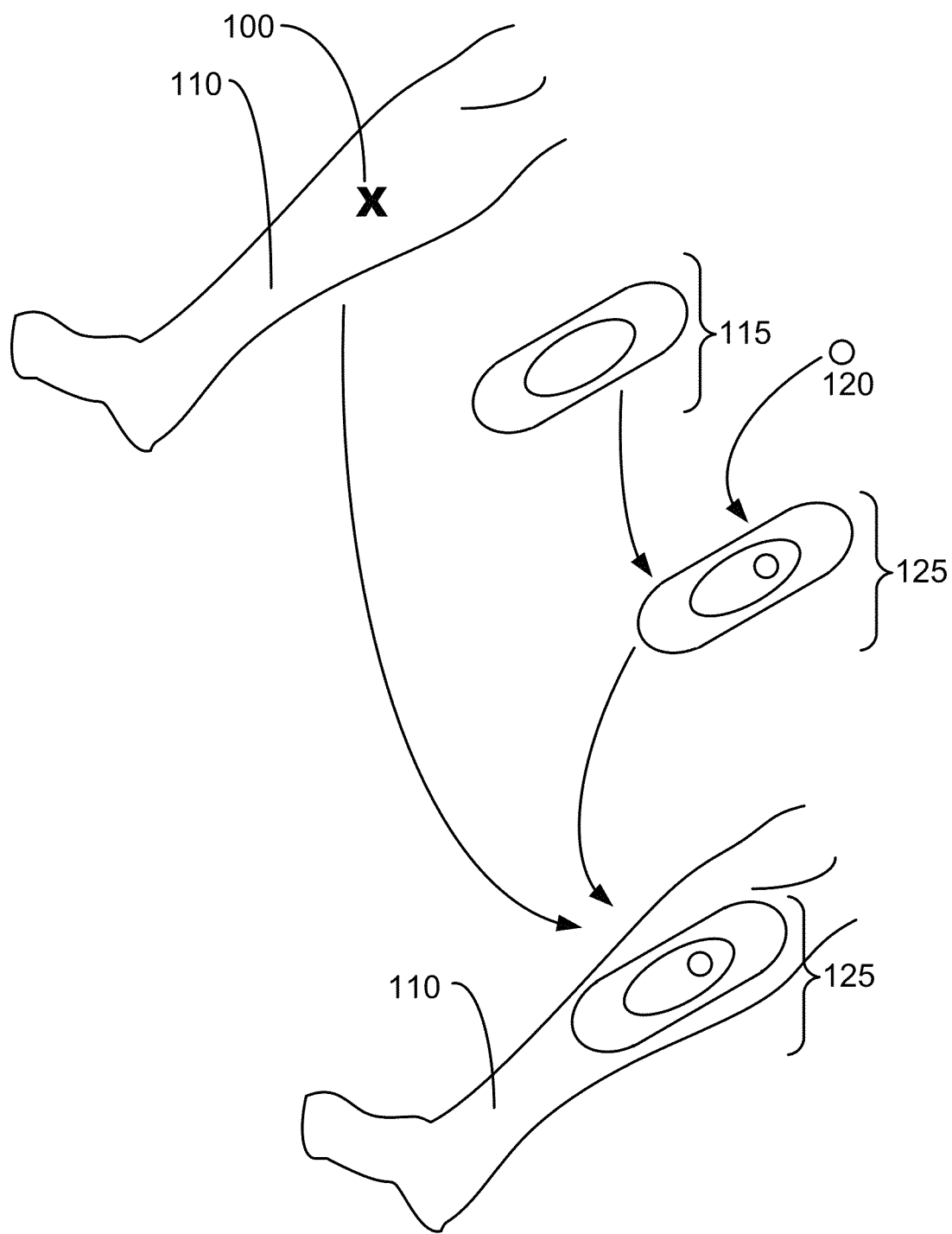
FIG. 1 is a schematic of an appurtenance to a wound dressing in use with a wound.

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments can be utilized, and other changes can be made, without departing from the spirit or scope of the subject matter presented here.

The use of the same symbols in different drawings typically indicates similar or identical items.

A wound dressing 115, selected by a medical caregiver as appropriate in size, shape and type for the wound 100, has an appurtenance 120 attached to generate an appurtenance affixed to a wound dressing combination unit, 125. The appurtenance 120 can be attached to the wound dressing 115 with a mechanical attachment, such as with attachments shaped like prongs, barbs, bristles, spikes, or spurs. The appurtenance 120 can be attached to the wound dressing 115 with a chemical attachment, such as a pressure-sensitive adhesive, a contact adhesive, or a quick-drying adhesive. The appurtenance 120 is a separate and distinct element that can be attached to the wound dressing 115 in a manner sufficient for operation during the use of a specific wound dressing 115. The appurtenance 120 is a separate and distinct element that can be attached to the wound dressing 115 in an irreversible manner.

For example, the appurtenance-wound dressing combination unit, 125, can be disposed of after use. Immediate disposal after use can be desirable to minimize biosafety, contamination and biohazard issues. The appurtenance 120 is a separate and distinct element that can be attached to the wound dressing 115 in a reversible manner. For example, the appurtenance-wound dressing combination unit, 125, can be taken apart into its component wound dressing 115 and appurtenance 120 after use. For example, the appurtenance 120 can be configured for reuse with a new wound dressing 115. The appurtenance 120 can be configured for reuse after treatment, such as after disinfection, cleaning, or sterilization. An appurtenance 120 to a wound dressing 115 can be reused, for example, on a succession of wound dressings 115 used by the same patient.

The appurtenance 120 is configured for functional use only when attached to the wound dressing 115. The appurtenance 120 is of a size, shape and material for functional use only when attached to the wound dressing 115. The appurtenance 120 is configured to operate in conjunction with the wound dressing 115. The appurtenance 120 is appended to the wound dressing 115 to generate an appurtenance-wound dressing combination unit 125, as illustrated in the lower right region of FIG. 1. The appurtenance 120 includes at least one region that projects into the structure of the wound dressing 115. In some embodiments, the region that projects into the structure of the wound dressing 115 is of a size and shape to be entirely enclosed within the structure of the wound dressing 115. In some embodiments, the region that projects into the structure of the wound dressing 115 is of a size and shape to project through the wound dressing 115, for example to a region adjacent to a wound. In some embodiments, the region that projects into the structure of the wound dressing 115 is of a size and shape to project through the wound dressing 115, for example to a wound bed region. In some embodiments, the region that projects into the structure of the wound dressing 115 is of a size and shape to project through a portion of the wound dressing 115, for example to a sinus or cavity of the wound bed. In some embodiments, the region that projects into the structure of the wound dressing 115 is of a size and shape to project through a portion of the wound dressing 115, for example to a dressing placed within a sinus or cavity of the wound bed. In some embodiments, the region that projects into the structure of the wound dressing 115 is of a size and shape to project through a portion of the wound dressing 115, for example to a layer placed adjacent to the wound surface. The appurtenance 120 affixed to the wound dressing 115 forms an integrated unit of the appurtenance and the wound dressing as a combination unit 125 (see, e.g. FIGS. 2, 5, and 7-11). In some embodiments, the wound dressing-appurtenance combination unit 125 is not readily separable, and the individual wound dressing 115 and appurtenance 120 are not suitable for separation and individual use after they have been joined together. As illustrated in the lower portion of FIG. 1, once the appurtenance 120 is affixed to the wound dressing 115, the appurtenance and the wound dressing together as a combination unit 125 are used to cover and monitor the wound 100.

In some aspects, an appurtenance 120 to a wound dressing 115 is configured to monitor one or more aspects of a wound 100. An appurtenance 120 to a wound dressing 115 can be used by a caregiver or a patient to monitor a wound 100. In some aspects, an appurtenance 120 to a wound dressing 115 is configured to monitor one or more aspects of a wound dressing 115. An appurtenance 120 to a wound dressing 115 can be used by a caregiver, including a patient, to monitor a wound dressing 115. An appurtenance 120 to a wound dressing 115 is configured to allow a user, such as a caregiver or patient, to monitor a wound dressing and the adjacent wound without disturbing the wound dressing 115 such as through removing the dressing 115 from the patient's wound 100. This approach, inter alia, improves comfort to the patient, reduces the chance of accidental infection in or contamination from uncovered wounds, and minimizes time requirements in wound care. As described further below, in some aspects, an appurtenance 120 to a wound dressing 115 includes a transmitter that sends a signal to a device used by a caregiver or patient to monitor the wound dressing from the same room as the patient. As also described further below, in some aspects, an appurtenance 120 to a wound dressing 115 includes a transmitter that sends a signal to a device used by a caregiver remotely, such as through a pager, remote computing device, cell phone, or dedicated remote signaling device. The signal transmitter sends a signal containing information associated a wound and/or adjacent wound dressing such that a caregiver is able to receive, directly or indirectly, information relating to monitoring a wound and adjacent wound dressing at a distance from the patient, without disturbing the patient and with minimal time spent analyzing the wound 100 or wound dressing 115.

As described further below, in some aspects, an appurtenance 120 to a wound dressing 115 is part of a system configured to automatically process and save information relating to an appurtenance 120 and the related wound dressing 115 to a medical record system, such as a medical records database. This automatic process reduces the potential for accidental loss or error in data entry regarding wound care, and reduces the time required by a caregiver in data entry into a record.

The wound dressing with the affixed appurtenance combination unit 125 is used to cover the wound 100 on the body part 110. The wound dressing with the affixed appurtenance combination unit 125 can be secured to the body part 110 in a routine manner for the type of wound dressing 115 generally, such as through adhesive integral to the wound dressing 115 or with additional adhesive, wrappings, tapes or glues as generally applicable to the type of wound dressing 115 utilized in a given medical situation. Although not illustrated in FIG. 1, the wound dressing with the affixed appurtenance combination unit 125 can similarly be removed using standard removal procedures, such as with gentle pressure, gentle pulling, unwrapping, allowing it to loosen over time, or biocompatible solvents. The appurtenances 120 described herein can be single-use and disposable along with the affixed wound dressing 115. In some embodiments, the appurtenances 120 described herein can be removed from a first wound dressing and then reconditioned, such as through cleaning or sterilization, and reused with a second wound dressing. In some embodiments, an appurtenance 120 can be reused for multiple wound dressings used on a single wound from a patient. The appurtenances 120 described herein are generally intended to be operable for the period of time a given wound dressing 115 is in use under standard conditions and time periods. After the wound dressing with the affixed appurtenance combination unit, 125 is removed from the body part 110, it can be disposed of as a unit with routine disposal methods.

It is envisioned that the appurtenances 120 described herein will be utilized while affixed to wound dressings 115 over wounds 100 of a variety of types, and operable to assist in the monitoring of wounds of a variety of types. For example, appurtenances 120 can be used in conjunction with wound dressings 115 to assist in monitoring acute wounds, such as those resulting from accidental injury or surgery. For example, appurtenances 120 can be used in conjunction with wound dressings 115 to assist in monitoring wounds closed by primary intention. For example, the appurtenances 120 can be used to assist in monitoring wound dressings over surgical wounds, such as incisions and surgical stitches. For example, the appurtenances 120 can be used to assist in monitoring wound dressings over acute wounds from injury, such as burn injuries, lacerations, or penetrating wounds. For example, appurtenances 120 can be used in conjunction with wound dressings 115 to assist in monitoring wounds closed by secondary intention. The appurtenances 120 can also be used to assist in monitoring wound dressings over chronic wounds, such as those arising from chronic medical conditions and situations. For example, the appurtenances can be used to monitor the status of wound dressings covering venous leg ulcers, diabetic foot ulcers, pressure ulcers or arterial ulcers. See: "Advances in Wound Healing Techniques," publication D11A, Frost and Sullivan, 2008; "An Overview of Ulceration Wounds," Publication M4BB-54, Frost and Sullivan 2009; and "US Advanced Wound Care Market," Publication N71A-54, Frost and Sullivan 2010, which are each incorporated herein by reference.

The appurtenances 120 described herein can be useful in conjunction with an affixed wound dressing as a combination unit 125 to monitor potential problems with a wound, such as excessive bleeding or other fluid formation that would be present in the wound dressing, or the presence of conditions in the dressing that indicate infection in an adjacent wound. See: Collier, "Recognition and Management of Wound Infections," *World Wide Wounds*, pages 1-9, (January 2004); and Gray, "Assessment, Diagnosis and Treatment of Infection," Wounds UK, vol. 7, no. 2, supplement, (2011), which are each incorporated herein by reference. For example, some types of wound discharge can indicate infection. See, for example, Cutting and Harding, "Criteria for Identifying Wound Infection," *Journal of Wound Care*, vol. 3, no. 4, 198-201 (1994), which is incorporated herein by reference. The appurtenances 120 as part of combination units 125 and related systems described herein can be used in conjunction with readily available types of wound dressings to monitor aspects of the affixed wound dressing, including parameters that indicate that a person should physically examine the wound dressing, such as excessive wetness, dryness, an elapsed period of time, or the presence of specific factors detected by one or more sensors of the appurtenance. The appurtenances 120 as well as related systems described herein can be used in conjunction with readily available types of wound dressings to monitor aspects of the affixed wound dressing, including indications that the wound dressing should be changed (i.e. excessively wet, dry, or soiled).

The appurtenances described herein include transmission units configured to transmit signals, and thereby report information regarding the status of the affixed wound dressing or wound, to associated systems. The resulting information reporting can be used, in some embodiments, to supplement the medical record for a patient in an automated system and automatic process. The resulting information reporting can be used, in some embodiments, to automatically notify a caregiver that the status of the wound dressing has altered, indicating that a person should physically inspect the wound dressing.

As used herein, a caregiver includes at least one of a patient, a caregiver, and medical personnel. A caregiver can utilize some embodiments of the appurtenances and related systems described herein in relation with multiple types of wound dressings. Appurtenances can be fabricated in shapes and sizes to conform to a variety of standard wound dressing sizes, shapes and types. Appurtenances can be fabricated with, for example, transmission units, antennas and sensors appropriate for use with a variety of wound dressings. Appurtenances can be fabricated with, for example, transmission units, antennas and sensors appropriate for different medical situations and monitoring requirements. Appurtenances can be fabricated with, for example, one or more projections of a size, shape and material appropriate for use with a variety of wound dressings. While it is envisioned that every appurtenance will not be appropriate for use with every wound dressing (for example due to size, shape or material compatibility), a given appurtenance is expected to be suitable for use with a range of potential wound dressings. For example, a given appurtenance of a specific size, shape and fabrication, including type of transmission unit, sensors, and projection(s), should be suitable for use with a variety of wound dressings of conforming sizes, shapes and types. Generally, any specific appurtenance embodiment is not expected to only conform to use with a unique wound dressing of a specific size, shape and type. Instead, it is expected that a specific appurtenance embodiment will be suitable for use with a range of wound dressings. Similarly, it is expected that a specific appurtenance embodiment will be suitable for use with a range of wound and wound dressing monitoring requirements.

In the attached drawings, an appurtenance 120 is generally illustrated as affixed to an outer surface of a wound dressing 115, for example an outer surface distal to a surface of the body part 110 adjacent to the wound 100. However, in some embodiments, an appurtenance 120 can be configured to attach to one or more surfaces of a wound dressing 115 adjacent to a surface of the body part 110 adjacent to the wound 100. For example, in embodiments wherein an appurtenance 120 is configured to be attached to a wound dressing 115 of a substantially rectangular, ovoid, or raised conformation, an appurtenance 120 can be configured to be attached to a side surface of the wound dressing 115. For example, in embodiments wherein an appurtenance 120 is configured to be attached to a wound dressing 115 with an unusually strong or thick outer cover layer, the appurtenance 120 can be configured to attach to an underside of the wound dressing 115. In some embodiments, an appurtenance is configured to attach to a surface of a wound dressing 115 in contact with the surface of the body part 110.

For example, the appurtenances described herein can be configured to be affixed to a dry gauze dressing, which can or can not include an outer cover layer. For example, the appurtenances described herein can be configured to be attached to a dry silicone or other solid foam dressing, which can or can not include an outer cover layer. For example, the appurtenances described herein can be configured to be affixed to a wound dressing used to close a small or thin wound or surgical incision, such as a butterfly dressing (e.g. SteriStrip™ adhesive strips, available from Nexcare™, part of 3M Corporation). For example, appurtenances such as those described herein can be configured to be affixed to a dressing configured to maintain moisture or other materials adjacent to the wound surface. For example, appurtenances such as those described herein can be configured to be used with hydrogel wound dressings, for example Aquaflo™ Hydrogel Wound Dressing by Kendall Corporation, or Elasto-Gel™ Hydrogel Occlusive Dressing by Southwest Technologies. For example, appurtenances such as those described herein can be affixed to wound dressings including hydrocolloids, for example DuoDERM CGF Sterile Hydrocolloid Dressing manufactured by DuoDERM Corporation. For example, appurtenances such as those described herein can be configured to be used with wound dressings containing one or more medicinal agents, such as antibiotics. For example, appurtenances such as those described herein can be used with wound dressings impregnated with PHMB (Polyhexamethylene Biguanide), such as Telfa™ A.M.D. antimicrobial wound dressings, manufactured by Kendall Corporation. For example, appurtenances such as those described herein can be configured to be used with wound dressings including ionic silver, such as Maxorb™ Extra Ag wound dressings manufactured by Medline Corporation. Appurtenances such as those described herein can be configured to be affixed to wound dressings over wounds wherein the tissue of the wound is being directly monitored using other devices, for example as described in U.S. Pat. No. 6,963,772 to Bloom et al., titled "User-retainable Temperature and Impedance Monitoring Methods and Devices," which is incorporated herein by reference. Appurtenances such as those described herein can be configured to be affixed to wound dressings over wounds wherein the patient is being directly monitored using other devices, for example as described in U.S. Pat. No. 7,030,764 to Smith and Cooper, titled "Apparatus and Method for Reducing the Risk of Decubitus Ulcers;" U.S. Pat. No. 7,297,112 to Zhou et al., titled "Embedded Bio-Sensor System;" U.S. Pat. Nos. 7,372,780, 8,014,234 and 7,813,226 to Braunberger, titled "Timing System and Device and Method for Making the Same;" U.S. Pat. No. 7,666,151 to Sullivan et al., titled "Devices and Methods for Passive Patient Monitoring;" U.S. Pat. No. 7,703,334 to Cochran, titled "Bandage Type Sensor Arrangement and Carrier Assembly Therefore, and Method of Manufacture;" and International Patent Publication No. WO 2005/009328 to Nikolic, titled "ABT-Anti-Bedsore Timer," which are each incorporated herein by reference. Appurtenances such as those described herein can also be used in conjunction with a system to monitor assets within a health care facility, for example as described in US Patent Application No. 2007/0247316 to Wildman et al., titled "Article Locating and Tracking Apparatus and Method," which is incorporated herein by reference.

Wound dressings 115 such as those described herein are generally used for a relatively short period of time, on the order of hours or days, and then removed for disposal. Similarly, a wound dressing with an affixed appurtenance combination unit 125 should be configured for use over the course of hours or days and then removed and disposed of using standard methods. A wound dressing with an affixed appurtenance is single use and disposable after use. For example, a caregiver can require a new wound dressing every 24 hours (1 day) for an acute wound. Any wound dressing utilized in this type of situation would, consequently, be of a size and shape to remain affixed to the wound region over the course of at least a 24 hour period and then removed for disposal. An appurtenance to a wound dressing intended for use over the course of a 24 hour time period, similarly should be of a size, shape, material fabrication, and capabilities to function while affixed to the wound dressing over the 24 hour period that the dressing is in use. As an additional example, a caregiver can decide that for another type of wound, such as a chronic wound, the wound dressing needs to be removed and replaced once every 3 days, or every 4 days, or every 5 days, or every 6 days, or every 7 days. Correspondingly, an appurtenance affixed to a wound dressing intended for use over the course of at least 3 to 7 days should be of a size, shape, material fabrication, and capabilities to function while affixed to the wound dressing over at least the 3 to 7 day period that the dressing is in use. In embodiments wherein an appurtenance is intended for reuse, such as reuse on a second or subsequent wound dressing used over a wound, the appurtenance should be of a size, shape, material fabrication and capabilities to function during the entire intended use, including the time period of removal from a first wound dressing and application to a second wound dressing.

Figure 2A:
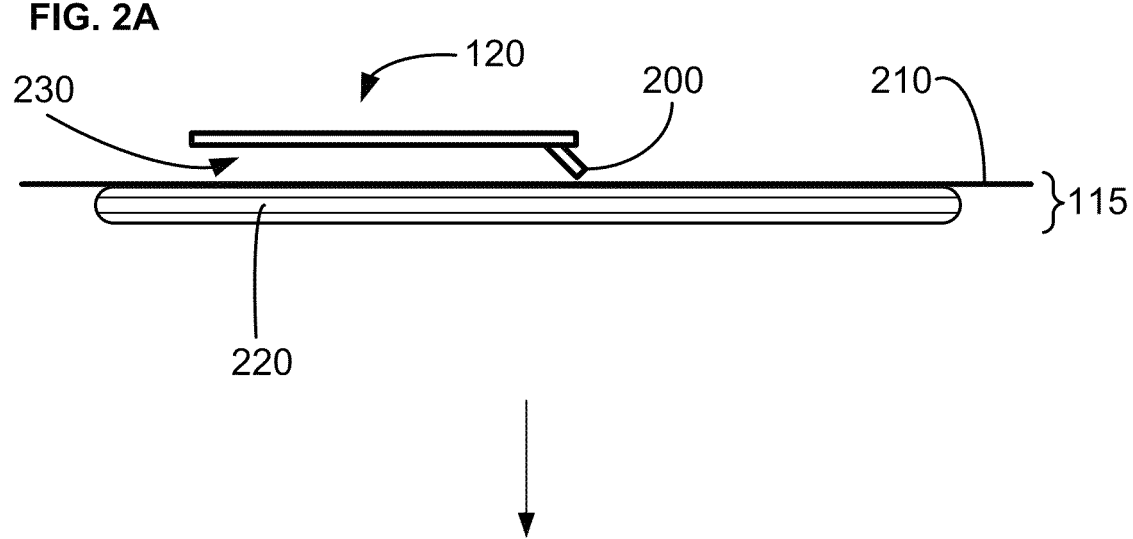
FIG. 2A is a schematic of an appurtenance to a wound dressing prior to attachment to a wound dressing.
Figure 2B:
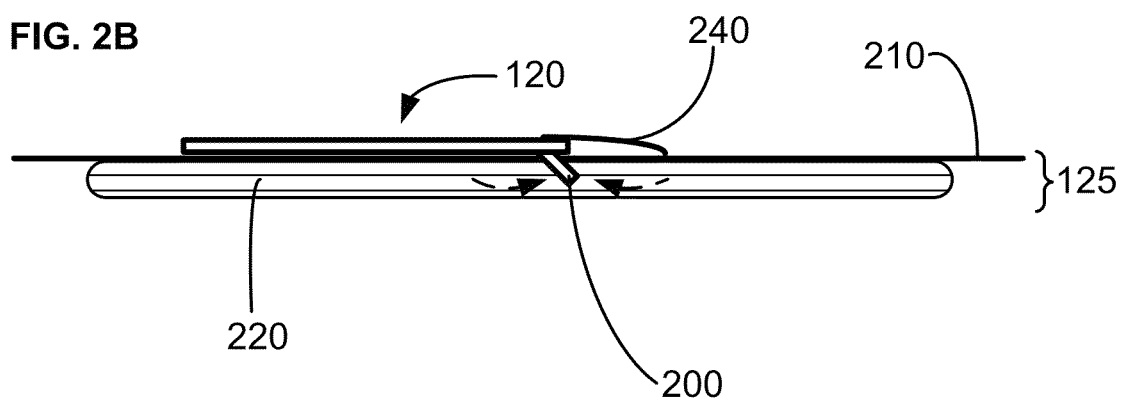
FIG. 2B is a schematic of an appurtenance to a wound dressing after attachment to a wound dressing.

FIGS. 2A and 2B depict further aspects of some embodiments of appurtenances to wound dressings. FIGS. 2A and 2B depict cross-section views of an appurtenance 120 to a wound dressing 115. As illustrated in FIG. 2A, the appurtenance 120 includes a substantially planar section and a projection 200. The substantially planar section includes a surface 230 configured to substantially conform with an outer surface of the wound dressing 115. In some embodiments, the surface 230 of the appurtenance 120 configured to conform with an outer surface of the wound dressing 115 can include adhesive of a type expected to reversibly or irreversibly adhere to the surface of the wound dressing 115. In some embodiments, the surface 230 of the appurtenance 120 configured to conform with an outer surface of the wound dressing 115 can include adhesive of a type expected to adhere to the surface of the wound dressing 115 for a period of time, and to be removable. In some embodiments, the surface 230 of the appurtenance 120 configured to conform with an outer surface of the wound dressing 115 can include barbs, hooks, pins, prongs or other extensions configured to adhere or fix onto the outer surface of the wound dressing 115. For example, an appurtenance 120 configured to conform with an outer surface of the wound dressing 115 can include barbs, hooks, pins, prongs or other extensions that irreversibly adhere to the outer surface of the wound dressing 115, such as by imbedding into the outer surface. For example, an appurtenance 120 configured to conform with an outer surface of the wound dressing 115 can include barbs, hooks, pins, prongs or other extensions that reversibly adhere to the outer surface of the wound dressing 115, such as by reversibly interacting with extensions projecting from the outer surface.

The appurtenance 120 depicted in FIGS. 2A and 2B includes a projection 200. As shown in FIGS. 2A and 2B, the projection extends from a surface 230 of the appurtenance 120 configured to conform with an outer surface of the wound dressing 115. The single projection depicted in FIGS. 2A and 2B projects at an angle from the plane formed by the substantially planar section of the appurtenance 120 conforming to the surface of the wound dressing 115. This angle is depicted in FIG. 2A as θ. In FIGS. 2A and 2B, for example, the angle shown as θ is approximately 135 degrees. A single projection 200 is shown in FIGS. 2A and 2B. However, in some embodiments an appurtenance 120 can include a plurality of projections 200. Depending on the embodiment, the projections 200 can also be at a variety of angles relative to the section of the appurtenance 120 conforming to the surface of the wound dressing 115. For example, in some embodiments, one or more projections can be at angles less than approximately 135 degrees, between approximately 135 degrees and approximately 90 degrees, or substantially at approximately 90 degree angles relative to a planar section of the appurtenance 120. In some embodiments, an appurtenance 120 includes a substantially planar region including a transmission unit, wherein the substantially planar region is configured to conform with an outer surface of the wound dressing 115, and one or more projections 200 projecting substantially perpendicular to the surface 230 configured to conform with an outer surface of the wound dressing 115. Depending on the embodiment, the projections 200 can project in a direction substantially away from the surface of the appurtenance configured to conform with an outer surface of the wound dressing 115 (e.g. as in FIGS. 2A and 2B), or angle in a direction substantially perpendicular to the surface 230 configured to conform with an outer surface of the wound dressing 115 of the appurtenance. Some embodiments include at least one projection 200 which is curvilinear. Some embodiments include at least one projection 200 which is a composite shape. In embodiments including one or more projections that are not substantially straight, an angle (e.g. θ as illustrated in FIG. 2A) of the projection 200 can be determined by the angle formed at the base of the projection immediately adjacent to the surface of the appurtenance configured to conform with an outer surface of the wound dressing 115.

The projection 200 can be a substantially hollow tubular structure. Although not illustrated in FIGS. 2A and 2B in this view, a substantially hollow tubular structure of the projection 200 includes an opening on the distal end of the projection 200. While the projection 200 depicted in FIGS. 2A and 2B can be a substantially tubular structure, in some embodiments projections can be of different shapes and conformations. For example, a projection 200 can be solid, tubular, conical, cylindrical, tapered, curved, angular or other shape or combination of shapes as appropriate to the specific embodiment. Embodiments including a plurality of projections can include projections of different sizes and shapes. A projection 120 can be substantially straight and form a substantially linear internal channel (e.g. as depicted in FIGS. 2A and 2B), or it can be curved and form a substantially curvilinear internal channel. The drawings illustrated herein are not to scale. The drawings illustrated herein represent relationships and shapes of the items described. Although not expressly illustrated herein, a projection 200 can be relatively large relative to the total size of the appurtenance. For example, the volume of a projection or a group of projections attached to an appurtenance can be 51%, 55%, 60%, 65%, 70%, 75%, 80%, 85%, 90%, 95% or 100% of the volume of the portion of the appurtenance configured to conform with an outer surface of a wound dressing (e.g. the substantially planar region as illustrated in FIGS. 2A and 2B). Similarly, a projection 200 can be relatively small relative to the total size of the appurtenance. For example, the volume of a projection or a group of projections attached to an appurtenance can be 49%, 45%, 40%, 35%, 30%, 25%, 20%, 15%, 10%, or 5% of the volume of the portion of the appurtenance configured to conform with an outer surface of a wound dressing (e.g. the substantially planar region as illustrated in FIGS. 2A and 2B). In some embodiments, a projection 200 is located at an edge region of the substantially planar region of the appurtenance 120, and in some embodiments a projection 200 is located substantially centrally to the planar surface 230 of the appurtenance 120 configured to conform with an outer surface of the wound dressing 115. In some embodiments, a substantially planar appurtenance 120 includes at least one projection 200 wherein the entire appurtenance 120 is of a size and shape to be secured against an external surface of a wound dressing 115 with force, for example from a human thumb or finger.

In some embodiments, an appurtenance 120 can be fabricated with one or more regions configured for the attachment of different modules. In some embodiments, an appurtenance 120 includes modules that are configured for removal and replacement. During fabrication, a basic appurtenance structure can be utilized and different specific modules added as desired in a particular embodiment. For example, an appurtenance 120 can be fabricated with at least one region configured to attach a projection. For example a region configured to attach a projection can include a region with a surface conforming to an outer surface of the projection. For example a region configured to attach a projection can include a conduit configured to align with the hollow interior of the projection. The region of the appurtenance 120 configured to attach a projection can be configured for attachment of different projection types, depending on the embodiment. For example, the region of the appurtenance 120 configured to attach a projection can be configured for attachment of projections of different lengths or different materials as desired in the construction of a particular embodiment. In some embodiments, an appurtenance 120 can have multiple regions configured for attachment of multiple projections of different types. In some embodiments, an appurtenance 120 can have one or more removable antenna modules. For example, an appurtenance 120 can have one or more removable power source modules, such as batteries or solar cells. In some embodiments, a module can include a spacer element, or a component configured to assist in physically positioning one or more other modules.

An appurtenance 120 can be fabricated from a variety of materials, as appropriate to an embodiment. An appurtenance 120 can be fabricated, for example, substantially from a plastic material. For example, a structural portion, such as a shell or base can be fabricated from a plastic material. For example, one or more projections can be fabricated from a plastic material. An appurtenance 120 can be fabricated, for example, from one or more acrylics, polyesters, silicones, polyurethanes and halogenated plastics. An appurtenance 120 can include one or more projections 200 fabricated, for example, from one or more plastic materials. An appurtenance 120 can include one or more projections 200 fabricated, for example, from one or more acrylics, polyesters, silicones, polyurethanes and halogenated plastics. An appurtenance 120 can be fabricated from one or more bio-compatible materials, for example bio-compatible plastics, resins, epoxies and metals. An appurtenance 120 can be fabricated from one or more composite materials, such as plastic with an overlay of epoxy or plastic with an overlay of one or more metals. An appurtenance 120 including a transmission unit can include, for example, one or more metal components, for example as circuitry or as one or more antennas. An appurtenance 120 including a transmission unit can include, for example, stainless steel, copper or zinc alloy. An appurtenance 120 can be fabricated from one or more ceramic materials, such as within a transmission unit. Generally, it is envisioned that materials with low weight will be suitable for a variety of appurtenance embodiments, so as to reduce weight and associated physical stress on a wound dressing. Similarly, it is envisioned that materials with sufficient strength and toughness to be fabricated into small and thin components will be desirable for fabrication of appurtenance embodiments. As the appurtenances are to be permanently affixed to the wound dressings and disposed of with the wound dressings, materials that do not require special handling or disposal are preferable in most embodiments.

In some embodiments, the appurtenance 120 includes a substrate, (e.g. 250) that is configured to attach to the wound dressing 115. For example, the substrate can be configured as a support for other features of the appurtenance 120. In some embodiments, the substrate includes a substantially planar structure wherein the area of surface 230 is less than the area of the wound dressing 115. In some embodiments, the substrate is configured to irreversibly attach directly to an external surface of the wound dressing 115. In some embodiments, the substrate includes an adhesive on a surface conforming to an external surface of the wound dressing 115 (e.g. surface 230 in FIG. 2A). An adhesive may be a pressure-sensitive adhesive, a contact adhesive, or a drying adhesive. For example, the surface conforming to an external surface of the wound dressing 115 can include a glue, epoxy, sealant, mucilage, paste or other binder material. In some embodiments, the surface of the substrate conforming to an external surface of the wound dressing 115 can include an adhesive covered by a removable protective sheet configured for detachment and exposure of the adhesive when the appurtenance 120 is attached to the wound dressing 115. In some embodiments, the surface 230 of the substrate of the appurtenance 120 configured to conform with an outer surface of the wound dressing 115 can include barbs, hooks, pins, prongs or other extensions configured to adhere or fix into the outer surface of the wound dressing 115. In some embodiments, the surface 230 of the substrate of the appurtenance 120 configured to conform with an outer surface of the wound dressing 115 can include a mixture or combination of any of the above.

In some embodiments, the substrate includes a flexible material. For example, the substrate can include a pliable plastic, a woven fabric material, soft mesh or other flexible material. In some embodiments, the substrate includes a rigid material. For example, the substrate can include at least one rigid plastic material in a location configured to provide support for a portion of the appurtenance. For example, the substrate can include at least one rigid plastic material at a location configured to attach a projection, the rigid plastic configured to provide physical support for the attached projection. In some embodiments, the substrate includes at least one bio-compatible material. For example, the substrate can include one or more bio-compatible plastic materials, one or more bio-compatible fabric materials, or one or more bio-compatible metals.

FIG. 2A depicts a cross section view of an appurtenance 120 adjacent to a wound dressing 115. As shown in FIG. 2A, the wound dressing 115 includes a dressing layer 220 and an outer layer 210. Not all wound dressings 115 should be expected to include multiple layers, and it is to be expected that some wound dressings 115 substantially include only a wound dressing material and not additional layers, structures or coverings. However, as illustrated in FIGS. 2A and 2B, in some embodiments wound dressings 115 include a plurality of layers. For example, a wound dressing 115 can include one or more outer layers 210 configured to protect and isolate the wound dressing layer(s) from microbes, external dirt and debris, dryness, wetness or other external factors. An outer layer can be fabricated from materials such as firm plastics or mesh materials. An outer layer can include a surface larger than the surface of the wound dressing layer, and can include adhesives on that surface configured to adhere the entire wound dressing to a body surface. A wound dressing 115 can include one or more layers of wound dressing 220 materials, such as gauze, films, foams, or sponges. A wound dressing 115 can include one or more layers of hydrogels, colloid gels, and medicinal agents impregnated within one or more layers of the wound dressing 220 or on a surface of the wound dressing 220 configured to face a wound.

A surface 230 of an appurtenance 120 can be configured to conform to the surface of the outer layer 210 of a wound dressing 115. For example, the surface can be of a size and shape that substantially conforms with the surface of the wound dressing 115. A surface 230 of an appurtenance 120 can include barbs, hooks, pins, prongs or other extensions configured to stick into the outer surface of the wound dressing 115. A surface 230 of an appurtenance 120 can include one or more adhesives of a type to attach the appurtenance 120 to the wound dressing 115. A surface 230 of an appurtenance 120 can be packaged with a removable cover over an adhesive layer.

FIG. 2B illustrates the appurtenance 120 and the wound dressing 115 of FIG. 2A after the appurtenance 120 is affixed to the wound dressing 125. As illustrated in FIG. 2B, a projection 200 of an appurtenance 120 can be configured to pierce through the outer layer 210 and into a wound dressing layer 220. A projection 200 of an appurtenance 120 can be of a size and shape to project from the outer surface of the wound dressing 115 to within layers of the wound dressing 115. A projection 200 can be of a size and shape to extend into an interior region of the wound dressing 115. A projection 200 can be of a size and shape to project within an interior region of the wound dressing 115. As shown in FIG. 2B, a projection 200 can be of a size and shape to project underneath one or more superficial structures of the wound dressing 115 (such as an outer layer 210) when the wound dressing 115 is in use. A projection 200 can be of a size and shape to project through a width of the wound dressing 115 when the appurtenance 120 is attached to the wound dressing 125. Also as illustrated in FIG. 2B, a projection 200 extending within the layers of the wound dressing 125 can be positioned so that fluids, depicted as dotted arrows, may enter a hollow within the projection 200 through capillary action through an opening in the projection 200. A projection 200 can include a substantially hollow structure. A projection 200 can include a substantially hollow structure with at least one opening in the projection 200 allowing the flow of fluid into the interior of the hollow projection 200. A projection 200 can include at least one sensor substantially within the projection.

An appurtenance 120 to a wound dressing 115 can include one or more projections 200 configured to be positioned into the wound dressing 115, a processor, and at least one transmitter operably attached to the processor. The appurtenance 120 can include one or more sensors operably attached to the processor. A projection 200 can include one or more sensors operably attached to the processor. A projection 200 can include one or more fluid conduits between an interior of the wound dressing 115 and the appurtenance 120. A fluid conduit refers to a conduit for fluid, such as a conduit of a size and shape to permit fluid flow through the conduit. A fluid conduit may actively promote flow through the fluid conduit, for example having interior dimensions that promote fluid flow through capillary action. A fluid conduit can be permissive for flow, with interior dimensions of sufficient size to allow fluid to flow through the fluid conduit. The at least one transmitter included in the appurtenance 120 can include a radio-frequency identification (RFID) transmitter. The at least one transmitter included in the appurtenance 120 can include a near field communication (NFC) device. The appurtenance 120 can include a transmission unit. The transmission unit can include a transmitter and a receiver. The transmission unit can include an RFID unit. The transmission unit can include a near field communication (NFC) device. The transmission unit can include at least one antenna. The transmission unit can include at least two antennas. The appurtenance 120 can include at least one indicator operably attached to the transmission unit. For example, the appurtenance 120 can include an LED operably attached to the transmission unit, configured to illuminate when the transmission unit is in operation.

The appurtenance 120 can include non-volatile memory. The appurtenance 120 can include volatile memory. The appurtenance 120 can include circuitry operably connected to the components of the appurtenance 120. The appurtenance 120 can include at least one antenna. The appurtenance 120 can include a receiver. The appurtenance 120 can include at least one sensor configured to be responsive to changes in capacitance. The appurtenance 120 can include at least one indicator.

A variety of sensors can be utilized in different embodiments of the appurtenances, depending on factors such as the intended use of the appurtenance, size, weight, cost, biocompatibility, safety and ease of disposal. "Sensors," as used herein, can be of a variety of types depending on the embodiment. One or more sensors can include at least one sensor responsive to changes in capacitance, or a measure of the ability of a configuration of materials to store electric charge. A general review of biosensors which detect changes in the dielectric properties of an electrode surface can be found in Berggren et al., "Capacitive Biosensors," *Electroanalysis* vol. 13, no. 3, 173-180, (2001), which is incorporated herein by reference. For example, one or more sensors can include a micromechanical biosensor with a fixed-fixed beam attached to an interdigitated capacitor (see, for example, Lim et al., "A Micromechanical Biosensor with Interdigitated Capacitor Readout," *Proceedings of the 2011 IEEE/ICME International Conference on Complex Medical Engineering*, May 22-25, Harbin, China, which is incorporated herein by reference). Sensors may also include nanowire nanosensors, for example as described in Cui et al., "Nanowire Nanosensors for Highly Sensitive and Selective Detection of Biological and Chemical Species," *Science*, vol. 293, 1289-1292 (2001), which is incorporated herein by reference. Sensors can include those utilizing antibodies secured to a graphene substrate. See Tehrani et al., "Detection of Monoclonal Antibodies using Chemically Modified Graphite Substances," *IEEE Sensors 2010 Conference Proceedings*, 428-431, (2010), which is incorporated herein by reference. In some embodiments, sensors include aptamer-modified graphene field-effect transistors, see Ohno et al., "Graphene Field-Effect Transistors for Label-Free Biological Sensors," *IEEE Sensors 2010 Conference Proceedings*, 903-906, (2010), which is incorporated herein by reference. A sensor in an appurtenance may interact with a sensor present in a wound dressing, for example as described in U.S. Pat. No. 6,283,938 to McConnell, titled "Medicating Bandage and Controllable Permeable Membrane," which is incorporated herein by reference. A sensor can include a field effect transistor (FET), such as described in U.S. Pat. No. 7,507,675 to Zuilhof et al., titled "Device Manufacturing Method and Device," which is incorporated herein by reference. A sensor can include a nano-cantilever device, such as described in U.S. Pat. No. 7,612,424 to Espinosa and Ke, titled "Nanoelectromechanical Bistable Cantilever Device," which is incorporated herein by reference.

The projections 200 can be functionally the same, or they can be different. Projections at different levels and amounts into a wound dressing can be oriented, for example, to form conduits for fluid flow between different regions of a wound dressing and/or a wound bed region and sensor(s) of the appurtenance. Projections can include the same type of sensors, or be connected to the same type of sensors, or they can include different types of sensors, or be connected to different types of sensors. For example, in some embodiments sensors detecting pH changes in a wound dressing can be more desirable in a central location of the appurtenance and sensors detecting wetness can be more desirable at an edge region of the appurtenance. In this example, pH changes can indicate potential infection in the central wound region, while edge wetness can indicate that the wound dressing is saturated and should be replaced. Sensors for pH suitable for some embodiments are known. See, for example, the "flexible, iridium oxide pH sensor for wound dressing material" project from the University of Texas at Arlington, the information sheet for which, with UTA reference number 08-21, is herein incorporated by reference.

Some embodiments of an appurtenance 120 include a selectively activated switch. A "selectively actuated switch," as used herein, refers to a switch capable of allowing a transmission unit to transmit a signal in response to a sensor. An appurtenance can include, for example, at least one sensor configured to respond to a substance within an interior region of a wound dressing and communicate a response to a selectively activated switch. A selectively actuated switch may, for example, be coupled to a transmission unit that includes an RFID device. See, for example, U.S. Pat. No. 7,411,505 titled "Switch Status and RFID Tag," which is incorporated herein by reference. A selectively activated switch can be a binary switch, or a switch with substantially two settings (i.e. "on" and "off"). A selectively actuated switch can be configured to be irreversible, or to irreversibly go from one state to a second state. A selectively actuated switch can be configured to be responsive to a change in capacitance. The selectively activated switch may, for example, be operably connected to at least one sensor. The selectively activated switch may, for example, be operably connected to the transmission unit. The selectively activated switch may, for example, be configured to alter the function of the transmission unit in response to a signal from a sensor. The selectively activated switch may, for example, be a switch configured to respond to changes in capacitance. The selectively activated switch may, for example, be a binary switch (i.e. with only off/on capability). The selectively activated switch may, for example, be a fluid conduit configured to permit the flow of fluid from the interior region of the wound dressing through the projection and into a location adjacent to the transmission unit. A selectively activated switch can include, for example, a substantially hollow structure. A selectively activated switch including a conduit can be configured to modulate the activity of an antenna in the transmission unit of the appurtenance 120 through fluid flow into contact with the antenna.

FIG. 2B also illustrates that in some embodiments a cover 240 is attached to the surface of the appurtenance 120 as well as to the surface of the wound dressing, such as to an outer layer of the wound dressing 210. An appurtenance 120 can include a substantially planar cover, the cover including an adhesive on a surface conforming to a surface of a wound dressing, the substantially planar cover configured to cover a location where the projection extends into the wound dressing. A cover 240 can be fabricated, for example, from a flexible plastic or mesh material. A cover 240 can be fabricated, for example, from an inflexible plastic or mesh material and configured in a size and shape to conform with the surfaces of the appurtenance 120 as well as to the surface of the wound dressing 115. A cover 240 can include adhesive on a surface facing the appurtenance and the wound dressing, the adhesive configured to attach the cover to the appurtenance and to the wound dressing. A cover 240 can be configured to stabilize the position of the appurtenance 120 relative to the wound dressing 115 when the appurtenance is affixed to the wound dressing 125 (e.g. as in FIG. 2B). A cover 240 can be configured to secure the appurtenance 120 relative to the wound dressing 115 when the appurtenance is affixed to the wound dressing 125 (e.g. as in FIG. 2B). A cover 240 can be configured to seal the juncture between the appurtenance 120 and the wound dressing 115, for example from dirt, debris, wetness or microbes that may enter the interior of the wound dressing if the juncture is not sealed. A cover 240 can be configured to seal any potential gaps between the projection 200 of the appurtenance 120 and the wound dressing 115, for example to seal any potential gaps from dirt, debris, wetness or microbes that may enter the interior of the wound dressing if the gap is not sealed.

In some embodiments, an appurtenance 120 to a wound dressing 115 is substantially sterilized prior to use. For example, the appurtenance 120 can be treated with one or more chemical disinfectants or UV surface radiation for a period of time sufficient to substantially sterilize the appurtenance 120 prior to use. For example, the appurtenance 120 can be treated with one or more antimicrobial gasses, for example ethylene oxide (ETO), prior to use. For example, the appurtenance 120 can be treated with a chemical sterilizing agent, such as hydrogen peroxide in liquid or vapor form, prior to use. For example, the appurtenance 120 can be treated with steam as an anti-infective prior to use. In some embodiments, an appurtenance 120 to a wound dressing 115 includes a sterile wrapper. For example, an appurtenance 120 to a wound dressing 115 can be stored and/or transported within a sterile wrapper, such as a firm paper wrapper or a plastic film. A sterile wrapper configured for storage and/or transport of an appurtenance can be treated to minimize contamination, for example coated with one or more anti-microbial agents.

Figure 3:
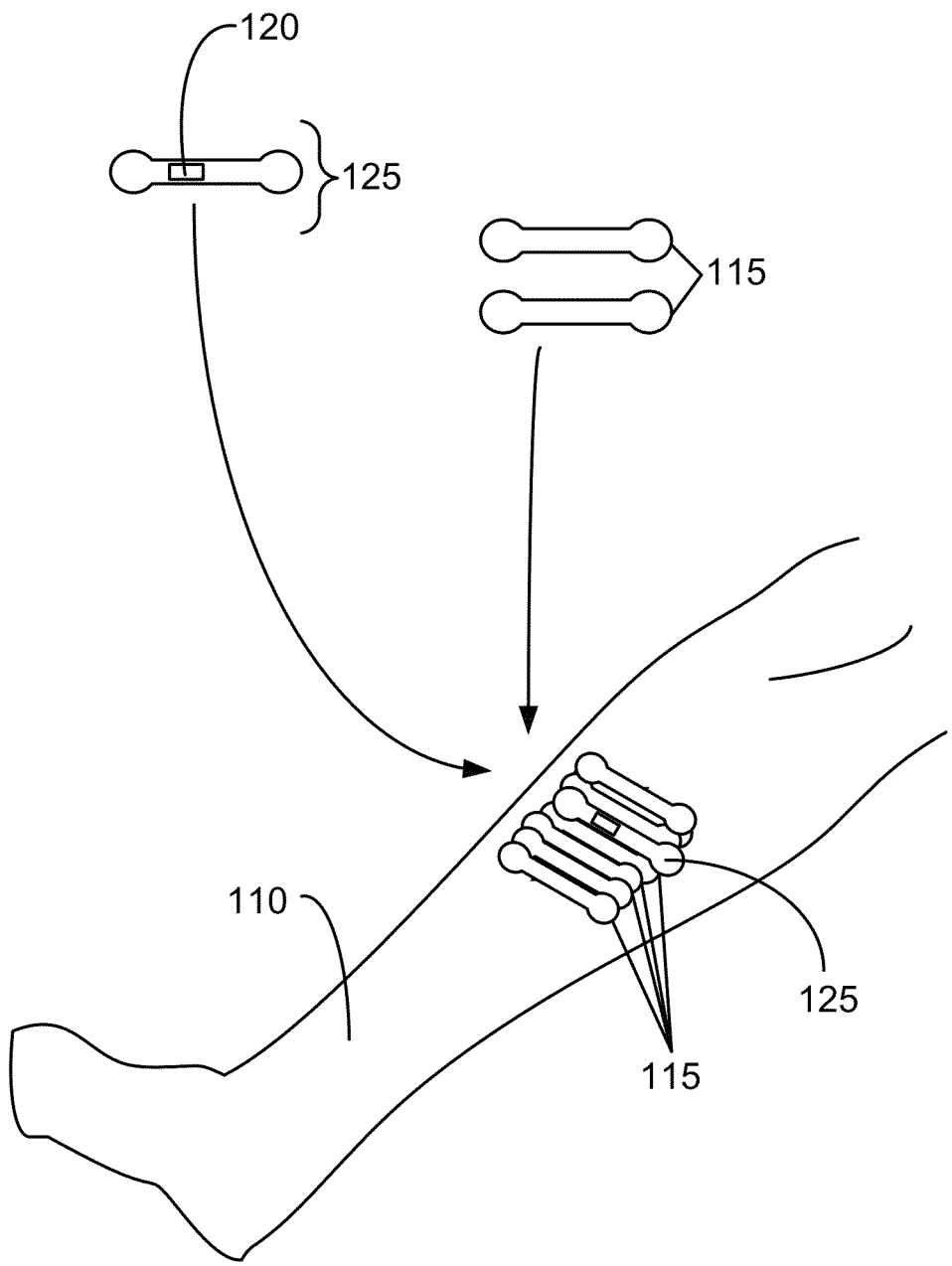
FIG. 3 is a schematic of an appurtenance to a wound dressing in use with a wound.

FIG. 3 illustrates additional aspects of some embodiments of appurtenances to wound dressings. In some situations, a medical caregiver may choose a wound dressing that is not a single unit, but a group of distinct units that together in situ on a body part form a complete, composite wound dressing. For example, a medical caregiver may choose a composite wound dressing made up from a group of butterfly dressings (e.g. SteriStrip™ adhesive strips, available from Nexcare™). In some embodiments, a medical caregiver may choose a compression bandaging system as part of a wound dressing. For example, a medical caregiver may choose a multi-layer compression bandaging system such as the Profore™ System or the Proguide™ System. In some embodiments, a medical caregiver may choose a negative pressure wound therapy system, such as the Renasys™ system or the Pico™ system, or the V.A.C.™ system. As illustrated in FIG. 3, a composite wound dressing can include a plurality of wound dressings 115 as well as at least one wound dressing with an affixed appurtenance combination unit 125. When the composite wound dressing is placed in position on a body part 110, such as a leg, the wound dressing with an affixed appurtenance combination unit 125 can be included with the grouping of wound dressings 115.

Figure 4:
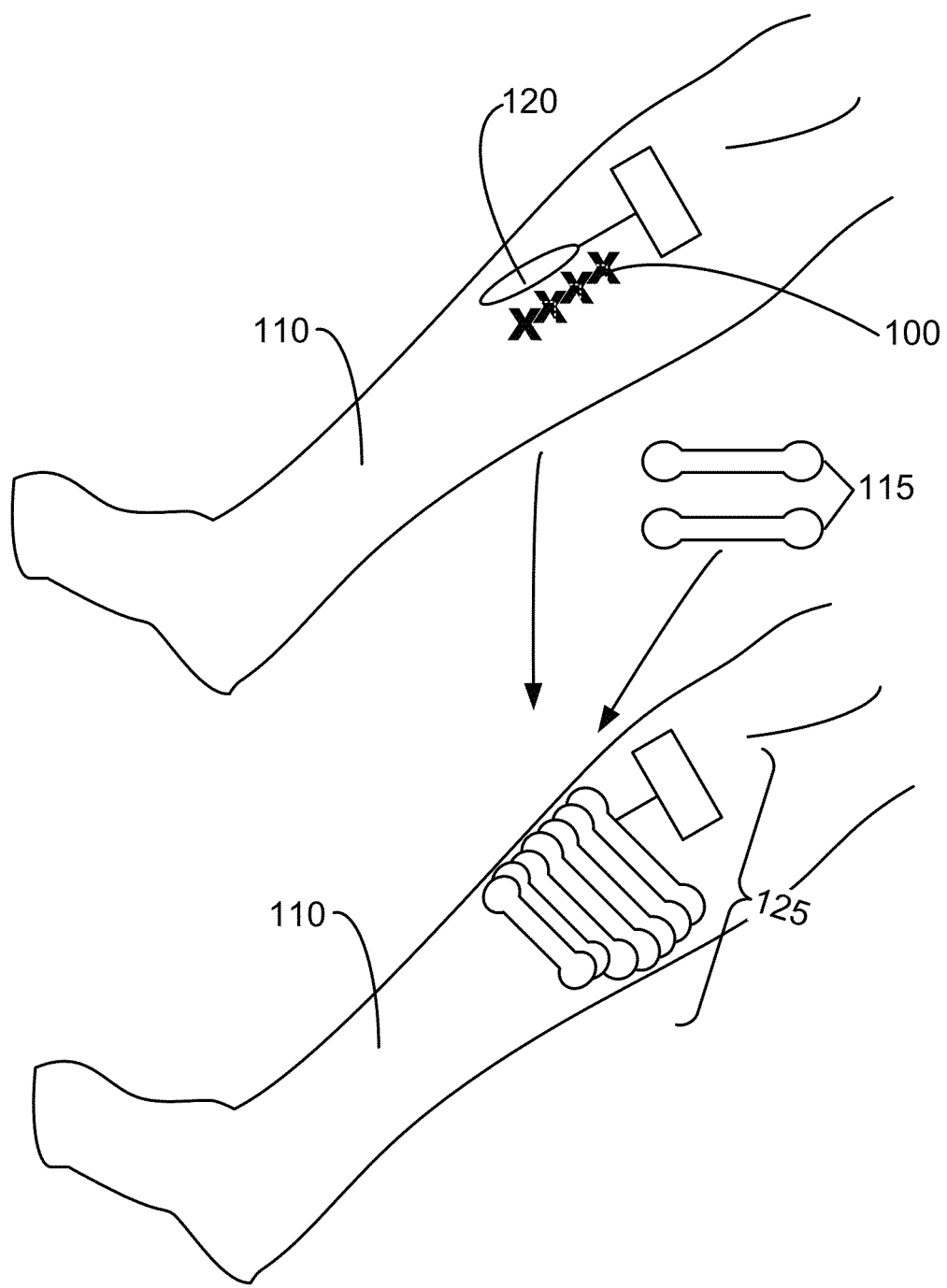
FIG. 4 is a schematic of an appurtenance to a wound dressing in use with a wound.

FIG. 4 illustrates additional aspects of some embodiments of appurtenances to wound dressings similar to that depicted in FIG. 3. In some situations, a medical caregiver may choose a wound dressing that is not a single unit, but a group of distinct units that together in situ on a body part form a complete, composite wound dressing. For example, a medical caregiver may choose a composite wound dressing made up from a group of butterfly dressings (e.g. SteriStrip™ adhesive strips). As illustrated in FIG. 4, an appurtenance 120 can be positioned on a body part 110, such as a leg, in a region adjacent to a wound 100. A series of wound dressings 115 can be positioned around and over at least a portion of the appurtenance 120 and affixed to the appurtenance 120 to form a composite wound dressing with an affixed appurtenance combination unit 125. For example, the appurtenance 120 can be interleaved with the individual units of wound dressings 115 and affixed to at least one wound dressing to form a composite wound dressing with an affixed appurtenance combination unit 125.

Figure 5:
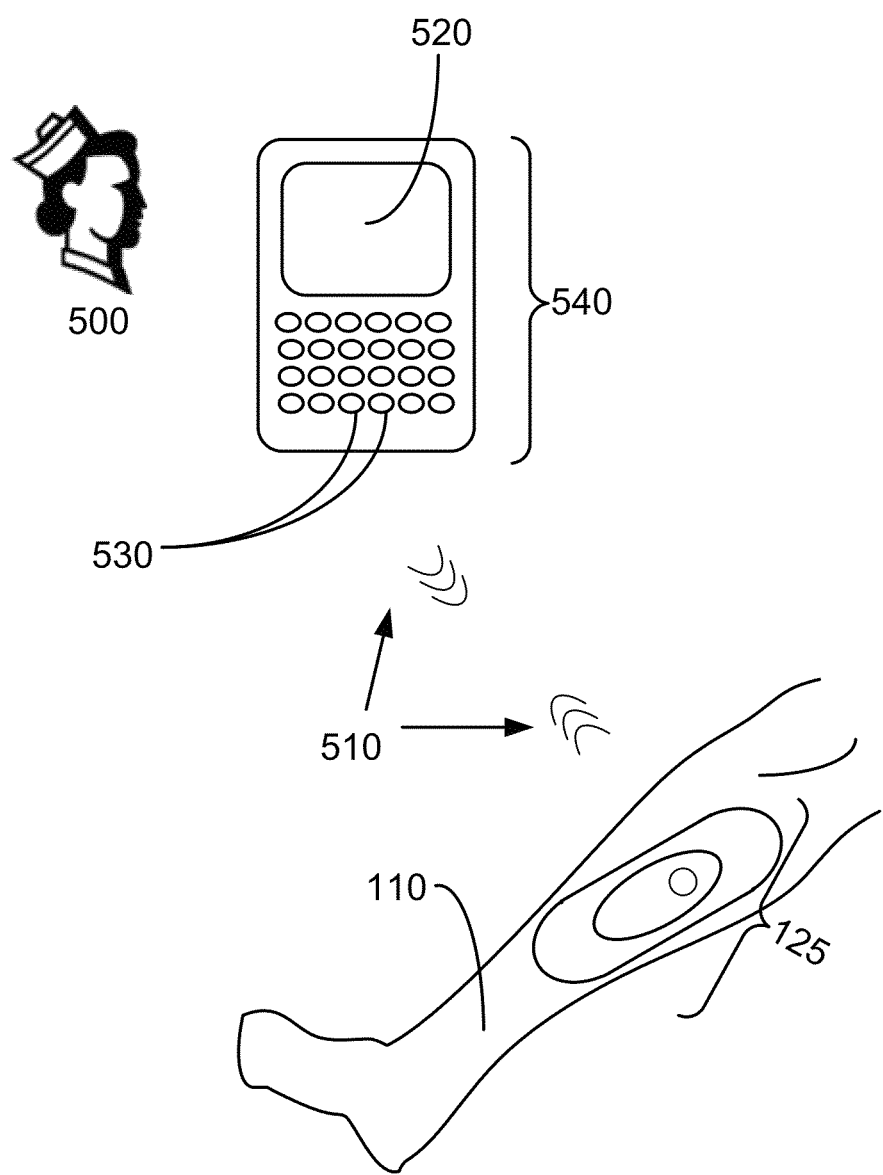
FIG. 5 is a schematic of an appurtenance to a wound dressing in communication with a local unit.

FIG. 5 illustrates aspects of a system including a wound dressing with an affixed appurtenance combination unit 125. As shown in FIG. 5, a wound dressing with an affixed appurtenance combination unit 125 is placed over a wound on a body part 110 of a patient. For example, the body part 110 may have been subject to a surgery, and therefore to have an acute wound. For example, the body part 110 can include an ulcer, and therefore have a chronic wound. The wound dressing with an affixed appurtenance combination unit 125 receives signals 510 from a local unit 540 and transmits signals 510 to the local unit 540. For example, the wound dressing with an affixed appurtenance combination unit 125 can include a passive RFID configured to transmit signals 510 after receiving signals 510 from a proximal RFID reader device in the local unit 540. The appurtenance includes one or more projections configured to be positioned into the wound dressing, a processor, and at least one transmitter operably attached to the processor (see, e.g. FIG. 2). The local unit 540 includes a receiver for the at least one transmitter, at least one processor operably attached to the receiver, and at least one communication unit operably attached to the processor (see, e.g. FIG. 6 and associated text).

A local unit 540 can include a handheld device. For example, the local unit 540 can include a distinct handheld device. For example, the local unit 540 can be included as part of a larger handheld unit, for example a tablet, a laptop, a cell phone, a personal communication device, or similar types of devices. A local unit 540 can be integrated with an institutional furnishing, such as a hospital bed, a medical stand, a bedside table or a surgical cart. A local unit 540 can be of a size, a shape and a configuration for portable handheld use. A local unit 540 can be configured to be attached to a mobile unit, such as the end of a hospital bed, a medical stand, a bedside table, a wheelchair, or similar device. For example, a local unit can be integrated with a medical cart, as described in U.S. Pat. No. 7,667,606 to Packert et al., titled "RF Enabled Surgical Cart and Use of Same in Operating Room Environment," which is incorporated herein by reference. A local unit 540 can be configured to be integrated into a furnishing. For example, a local unit 540 can be integrated into a hospital bed, a bedside hospital monitor, a bedside table, a medical chair, a medical table, or similar furnishing. A local unit 540 can include a display unit 520. In some embodiments, there can be a secondary device configured to relay signals to the local unit 540, for example as described in U.S. Pat. No. 7,986,235 to Posamentier titled "RFID Receive-Only System," which is incorporated herein by reference. A local unit 540 can include a communication unit configured to send signals to a central assembly (see, e.g. FIGS. 7 and 8). The communication unit of a local unit 540 can include at least one of: a visual display, a sound generator, a vibrating unit, and one or more light displays. A local unit 540 can include at least one user interface, such as a screen, monitor, touchscreen or voice recognition element. A local unit 540 can include an auditory signal generator. A local unit 540 can include an input device 530, for example a keyboard. Although the local unit 540 illustrated in FIG. 5 includes a keyboard as an input device 530, in some embodiments the input device 530 can include other types of input devices, for example a touchscreen, stylus, keypad, or voice recognition system. A local unit 540 can include a power source. For example, a local unit 540 can include a solar cell, a battery or connect to a building power supply through a wire connection. A user 500, such as a medical caregiver, operates the local unit 540.

A user 500 can include a medical caregiver, such as a nurse or doctor, or a patient, patient family member or other individual monitoring the wound dressing. Although user 500 is shown/described herein as a single illustrated figure, those skilled in the art will appreciate that user 500 can be representative of a human user, a robotic user (e.g., computational entity), and/or substantially any combination thereof (e.g., a user can be assisted by one or more robotic agents) unless context dictates otherwise. Those skilled in the art will appreciate that, in general, the same can be said of "sender" and/or other entity-oriented terms as such terms are used herein unless context dictates otherwise. A user 500 may utilize a local unit 540 through a user interface, for example one or more buttons, a keyboard, a touchscreen, a voice recognition device, a stylus, or other means.

A local unit 540 can include a communication device including at least one transmitter. A local unit 540 can include a radio-frequency identification (RFID) receiver. A local unit 540 can include a near field communication (NFC) device. A local unit 540 can be configured to send and receive signals from a plurality of appurtenances. For example, a local unit 540 can be configured to send and receive signals from multiple appurtenances affixed to wound dressings on a single individual. For example, a local unit 540 can be configured to send and receive signals from multiple appurtenances affixed to wound dressings on multiple individuals in a defined area, such as a single room or region of a room. A local unit 540 can be configured to send signals to one or more wound dressings with attached appurtenances 125 automatically. For example, local unit 540 can be configured to send signals to one or more wound dressings with attached appurtenances 125 at least one of: every 30 minutes; every hour; every 2 hours; or every 3 hours. A local unit 540 can be configured to send signals to one or more wound dressings with attached appurtenances 125 on a schedule selected by the user 500. For example, local unit 540 can be configured to send signals to one or more wound dressings with attached appurtenances 125 on at least one of: an hourly schedule; a schedule of every 30 minutes for 4 hours, followed by hourly signals; or a schedule provided by the user through the user interface (e.g. the keyboard 530). A local unit 540 can be configured to send signals to one or more wound dressings with attached appurtenances 125 on a preset schedule which is selected by the user 500. For example, local unit 540 can be configured to send signals to one or more wound dressings with attached appurtenances 125 on at least one of: a schedule preset to monitor a wound after surgery; a schedule preset to monitor a chronic wound; an hourly schedule; a schedule of every 2 hours; a schedule of hourly during the day and every 2 hours at night; or other preset schedules.

The signals 510 sent from the local unit 540 to the wound dressing with attached appurtenance unit 125 can be radio frequency signals in a particular wavelength, or range of wavelengths. For example, the signals can be in the UHF range, such as a UHF sub-range commonly used in a particular geographic region. See, for example the "Worldwide RFID UHF Map" by Intelleflex Corporation (©2009), which is incorporated herein by reference. For example, the signals can be in a range of 902-928 MHz. For example, the signals can be in a range specified by an industry standard. For example, the signals can be in the approximately 13.56 megahertz (MHz) range, or within the ISO 14443 standard parameters. For example, the signals can be in the IEEE 802.11x standard or the Bluetooth standard range. See, for example, U.S. Pat. No. 7,215,976 to Brideglall, titled "RFID Device, System and Method of Operation Including a Hybrid Backscatter-based RFID Protocol Compatible with RFID, Bluetooth and/or IEEE 802.11x Infrastructure," which is incorporated herein by reference. For example, the signals can be in the approximately 131 kilohertz (KHz) range, for example as part of a RuBee™ (IEEE standard 1902.1) system (equipment sold, for example, by Visible Assets™, Inc). See for example: the description of RuBee™ systems from the Visible Assets™ webpage; Stevens et al., "RuBee (IEEE 1902.1)—The Physics Behind, Real-Time, High Security Wireless Asset Visibility Networks in Harsh Environments," a white paper from Visible Assets™; and in US Patent Application No. 2007/0171076 to Stevens and Waterhouse, titled "Low-frequency Radio Tag Encapsulating System," each of which are incorporated herein by reference.

Similarly, the signals 510 sent from the wound dressing with attached appurtenance unit 125 to the local unit 540 can be one of the types described above in relation to signals 510 sent from the local unit 540. In some embodiments, the wound dressing with attached appurtenance unit 125 includes a backscatter or reflective transmission device, and so the signals 510 sent from the wound dressing with attached appurtenance unit 125 to the local unit 540 can be backscatter or reflective signals. For example, as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference herein.

The signals 510 transmitted from the local unit 540 or transmitted from the wound dressing with attached appurtenance unit 125 can be sent in a fixed direction from the signal source. The wound dressing with attached appurtenance unit 125 and the local unit 540 may each include markings or other visible aspects directing a user how as to orient the wound dressing with attached appurtenance unit 125 and the local unit 540 relative to each other for signal directionality.

In many embodiments, it is envisioned that the signal strength of a signal 510 transmitted from either the local unit 540 or transmitted from the wound dressing with attached appurtenance unit 125 will be such that the signal 510 will not travel a significant distance. The local unit 540 and the wound dressing with attached appurtenance unit 125 may, therefore, need to be placed in reasonably close proximity for signals 510 to travel between the devices. For example, the signal 510 transmitted from either the local unit 540 or transmitted from the wound dressing with attached appurtenance unit 125 can be such that the receiver of such signals should be within the same room. For example, the signal 510 transmitted from either the local unit 540 or transmitted from the wound dressing with attached appurtenance unit 125 can be such that the receiver of such signals should be within 10 feet. For example, the signal 510 transmitted from either the local unit 540 or transmitted from the wound dressing with attached appurtenance unit 125 can be such that the receiver of such signals should be within 3 feet.

Figure 6:
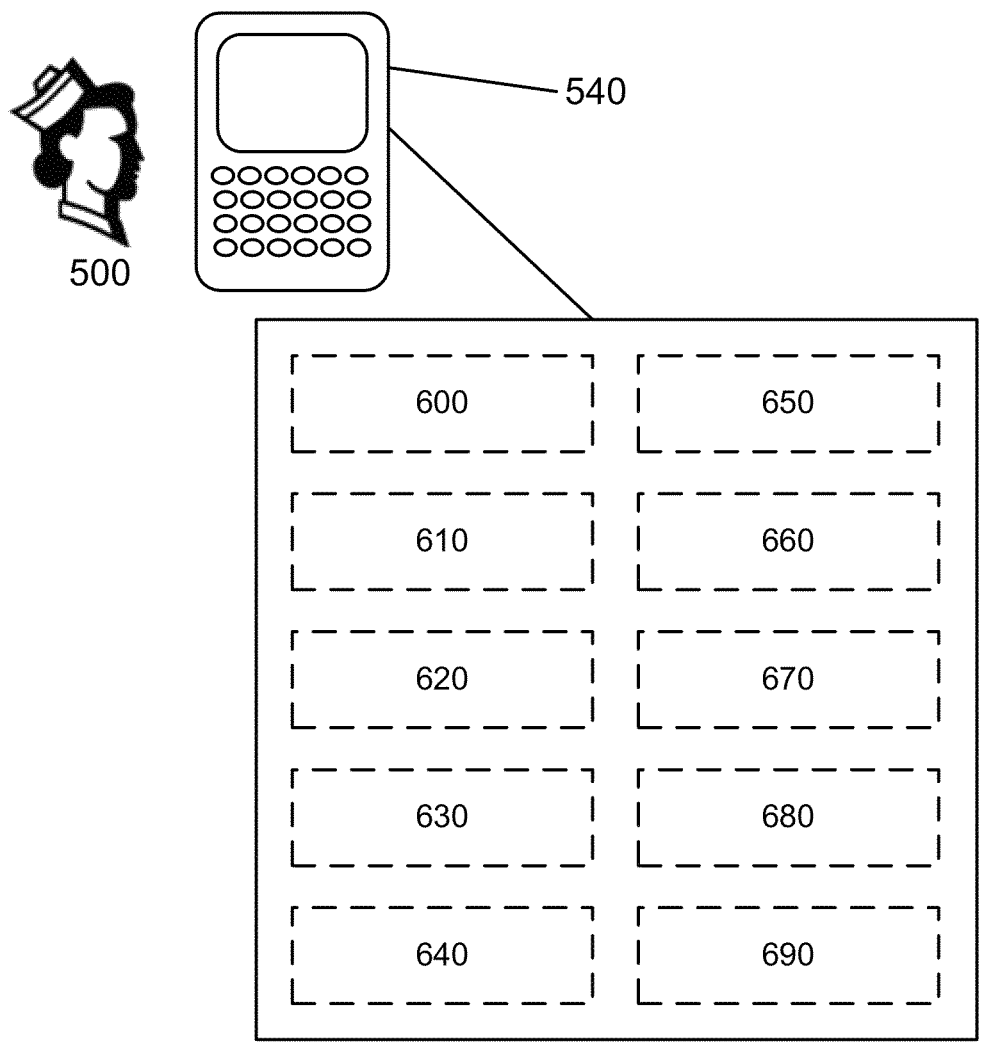
FIG. 6 is a schematic of an appurtenance to a wound dressing in communication with a local unit.

FIG. 6 illustrates aspects of a system including a wound dressing with an affixed appurtenance unit 125. As illustrated in FIG. 6, a wound dressing with an affixed appurtenance unit 125 is positioned over a wound on a body part 110 of a patient. The wound dressing with an affixed appurtenance unit 125 sends and receives signals 510 from a local unit 540. The local unit 540 can be utilized by a user 500.

FIG. 6 illustrates aspects of the local unit 540. The local unit 540 includes a housing, with connected user interface and input components (e.g. a display and keyboard). The local unit 540 can include a processor 600. The local unit 540 can include memory 610. The memory 610 can include, for example, volatile and/or non-volatile memory. The local unit 540 can include at least one antenna 620. The local unit 540 can include circuitry 630, operably connected to the other components of the local unit. The local unit 540 can include one or more transmitters 640. The local unit 540 can include one or more receivers 650. The local unit 540 can include one or more power sources 660, such as a battery, a solar cell, or a plug-in socket. The local unit 540 can include logic 670. The local unit 540 can include other components 680, 690 as appropriate to a specific embodiment. The local unit 540 can include, for example, an application specific intelligent microsensor as described in U.S. Pat. No. 6,889,165 to Lind et al., titled "Application Specific Intelligent Microsensors," which is incorporated herein by reference herein.

FIG. 7 shows aspects of a system including a wound dressing with an affixed appurtenance unit 125. As shown in FIG. 7, a wound dressing with an affixed appurtenance unit 125 is attached to a body part 110 of a patient over a wound. The wound dressing with an affixed appurtenance unit 125 sends and receives signals 510 from a local unit 540. The local unit 540 can be utilized by a user 500.

Also as shown in FIG. 7, the local unit 540 may send and receive signals 710 from a central assembly 705. The local unit 540 may send and receive signals 710 with a wireless connection, as shown in FIG. 7, or the local unit 540 may send and receive signals 710 through a wire connection. A central assembly 705 includes at least one user interface device (e.g. a keyboard, touchscreen, display, etc.) which can be utilized by a system user 700. A system user 700 can include a medical caregiver, such as a nurse or doctor, or a patient caregiver, or other individual monitoring the wound dressing. Although system user 700 is shown/described herein as a single illustrated figure, those skilled in the art will appreciate that system user 700 can be representative of a human user, a robotic user (e.g., computational entity), and/or substantially any combination thereof (e.g., a user can be assisted by one or more robotic agents) unless context dictates otherwise. Those skilled in the art will appreciate that, in general, the same can be said of "sender" and/or other entity-oriented terms as such terms are used herein unless context dictates otherwise.

FIG. 7 illustrates aspects of some embodiments of a central assembly 705. A central assembly 705 can include a processor, a receiver configured to receive signals from the at least one communication unit, and at least one user interface. The central assembly 705 can include, for example, at least one transmitter 720. The central assembly 705 can include a transmitter configured to send signals to the local unit 540. The central assembly 705 can include a transmitter configured to send signals to one or more mobile devices. For example, the central assembly 705 can include a transmitter configured to send signals to one or more cell phones, pagers, PDA devices, or mobile computing devices. The central assembly 705 can include, for example, at least one receiver 725. The central assembly 705 can include, for example, at least one antenna 730. The central assembly 705 can be configured to receive signals from a plurality of local units 540. For example, a central assembly 705 can be configured to receive signals from all of the local units in a hospital, nursing home, care facility, or a section thereof. The central assembly 705 can be configured to send signals to a plurality of local units 540. For example, a central assembly 705 can be configured to send signals to all of the local units in a hospital, nursing home, care facility, or a section thereof. The central assembly 705 can include, for example, memory, which can include volatile and/or non-volatile memory. The central assembly 705 can include, for example, circuitry 740. The circuitry 740 can be operably connected to other components of the central assembly 705. The central assembly 705 can include, for example, a power source 745. A power source 745 can include, for example, at least one battery, a plug-in connection, a wireless power source, or a solar cell. The central assembly 705 can include, for example, a processor 750. The central assembly 705 can include, for example, logic 755. The central assembly 705 can include, for example, additional components 760, 765. The central assembly 705 can include at least one display. The central assembly 705 can include at least one indicator, such as a visible or auditory indicator.

A central assembly 705 can be located primarily or mainly in one or a limited number of machines, for example one or more computer servers. A central assembly 705 can be configured to interact with a computer system. A central assembly 705 may interface with, or include, a 2G-RFID-Based E-Healthcare system. See, for example, Chen et al., "A 2G-RFID-Based E-Healthcare System," *IEEE Wireless Communications*, February 2010, pages 37-43, which is incorporated herein by reference. A central assembly 705 may interface with, or include, a digital management system, for example as discussed in: Fisher, "Indoor Positioning and Digital Management Emerging Surveillance Regimes in Hospitals" in T. Monahan (Ed), Surveillance and Security: Technological Politics and Power in Everyday Life (pp. 77-88), New York: Routledge (2006); and Fisher and Monahan, "Tracking the Social Dimensions of RFID Systems in Hospitals," *International Journal of Medical Informatics* 77 (2008) 176-183, which are each incorporated herein by reference. A central assembly 705 may interface with, or include, a drug tracking system, as described, for example, in "RFID Systems for Pharmaceutical Distributors to Meet the New FDA Regulations on Drugs," white paper from Abhisam Software, (2006), which is incorporated herein by reference.

Figure 8:
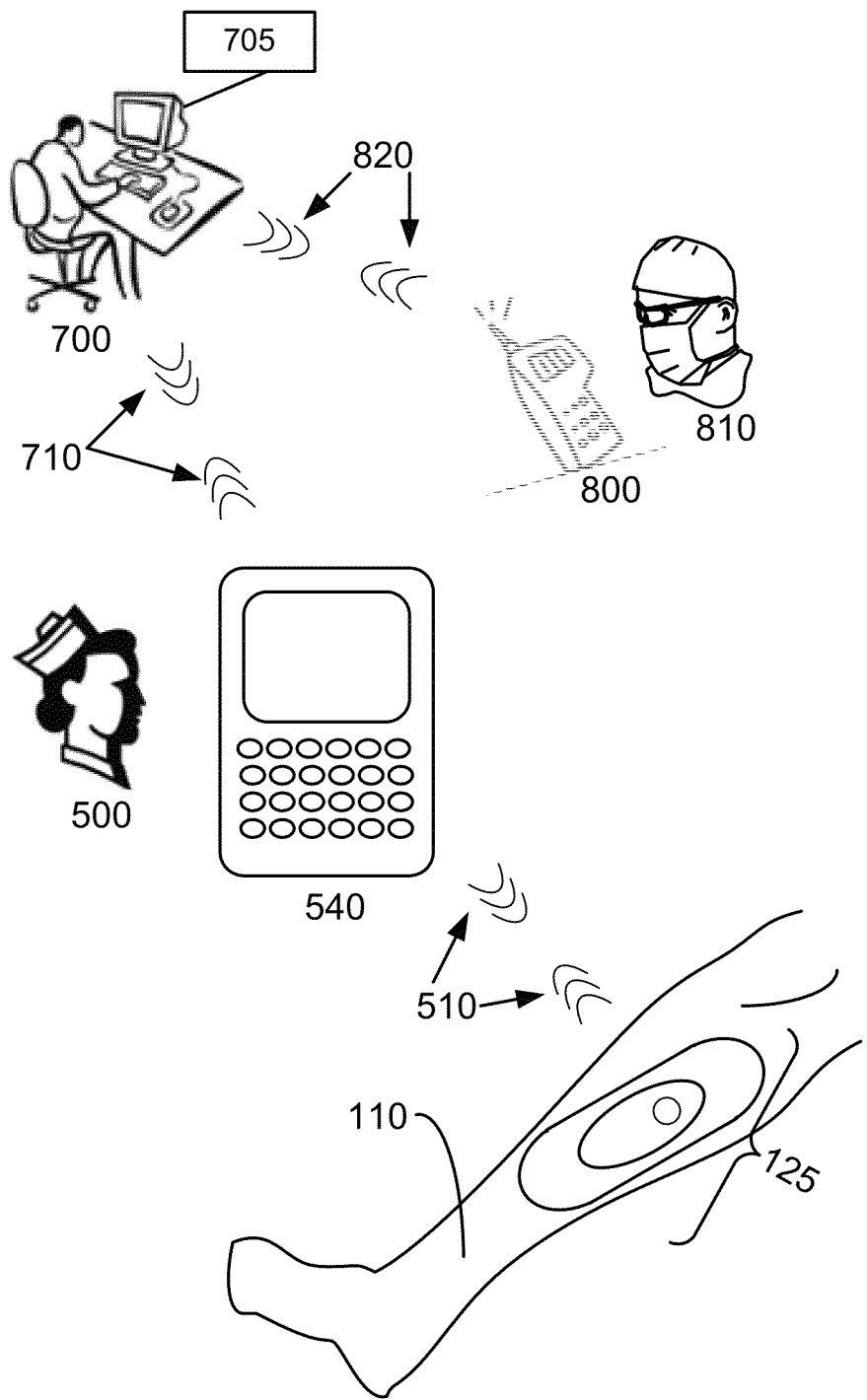
FIG. 8 is a schematic of an appurtenance to a wound dressing in communication with a local unit, a central assembly and a remote device.

FIG. 8 illustrates aspects of a system including a wound dressing with an affixed appurtenance unit 125. As shown in FIG. 8, a wound dressing with an affixed appurtenance unit 125 is placed over a wound on a body part 110 of a patient. The wound dressing with an affixed appurtenance unit 125 receives signals 510 from a local unit 540 and transmits signals 510 to the local unit 540. The local unit 540 can be utilized by a user 500.

Also as shown in FIG. 8, the local unit 540 may send and receive signals 710 from a central assembly 705. A system user 700 interacts with a user interface device operably attached to the central assembly 705. The central assembly 705 sends signals 820 to and receives signals 820 from a remote device 800. Although the signals 820 illustrated in FIG. 8 are wireless signals 820, in some embodiments the signals 820 can be transmitted through a wire connection. The remote device 800 can be, for example, a dedicated remote device 800. The remote device 800 can be, for example, integrated with another device, such as a laptop, cell phone, tablet computing device, pager, PDA, or personal computing device. The remote device 800 can be configured to initiate a warning indicator when it receives a signal 820 from the central assembly 705 regarding the wound dressing with an affixed appurtenance unit 125. For example, the remote device 800 can be configured to initiate a warning light, display, auditory message, auditory tone, or vibration when it receives a signal 820 from the central assembly 705 regarding the wound dressing with an affixed appurtenance unit 125. The remote device 800 is configured for use by a remote user 810. A remote user 810 can include a medical caregiver, such as a nurse or doctor, or a patient caregiver, or other individual monitoring the wound dressing. Although remote user 810 is shown/described herein as a single illustrated figure, those skilled in the art will appreciate that remote user 810 can be representative of a human user, a robotic user (e.g., computational entity), and/or substantially any combination thereof (e.g., a user can be assisted by one or more robotic agents) unless context dictates otherwise. Those skilled in the art will appreciate that, in general, the same can be said of "sender" and/or other entity-oriented terms as such terms are used herein unless context dictates otherwise. The remote user 810 may initiate the remote device 800 to transmit a signal 820 to the central assembly 705, for example a signal 820 indicating that a message has been received regarding the wound dressing with an affixed appurtenance unit 125.

Figure 9:
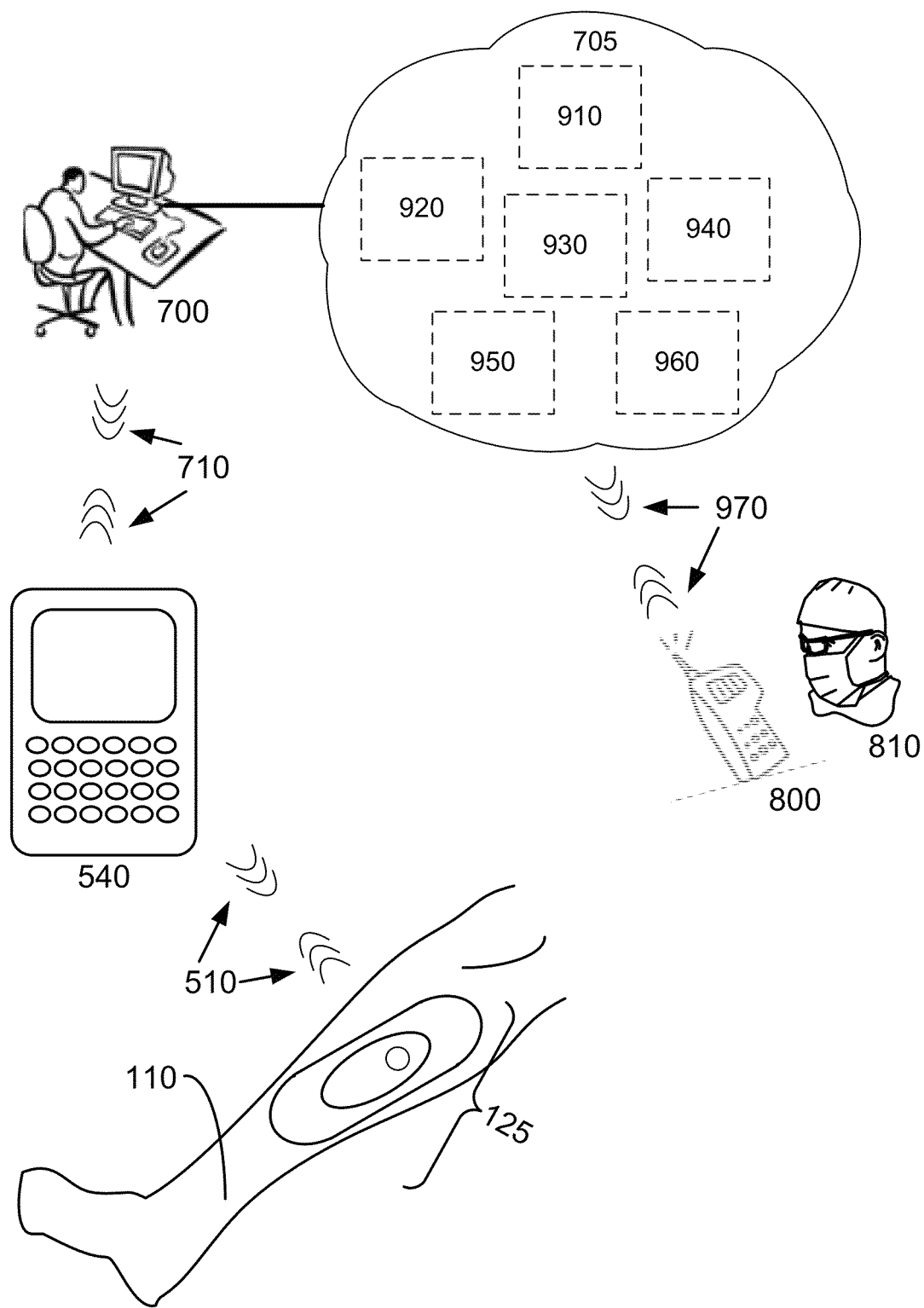
FIG. 9 is a schematic of an appurtenance to a wound dressing in communication with a local unit, a central assembly and a remote device.

FIG. 9 illustrates aspects of a system including a wound dressing with an affixed appurtenance unit 125. As illustrated in FIG. 9, a wound dressing with an affixed appurtenance unit 125 is placed over a wound on a body part 110 of a patient. The wound dressing with an affixed appurtenance unit 125 sends and receives signals 510 from a local unit 540. The local unit 540 sends and receives signals 710 from a central assembly 705. The central assembly 705 illustrated in FIG. 9 is in a "cloud" format, with a significant portion of its components distributed on a computer network. The central assembly 705 is configured to communicate with one or more interface devices 700, for example an individual computer.

Depending on the embodiment, a cloud-based central assembly 705 can include a plurality of components as illustrated in FIG. 9. For example, a central assembly 705 can include logic 910. For example, a central assembly 705 can include circuitry 920. The circuitry 920 can be operably connected to other components of the central assembly 705. For example, a central assembly 705 can include memory 930. For example, a central assembly 705 can include one or more power sources 940. For example, a central assembly 705 can include at least one processor 950. For example, a central assembly 705 can include other components 960.

Also as illustrated in FIG. 9, a central assembly 705 may communicate with a remote device 800 through signals 970. Signals 970 can be sent and received by an aspect of the central assembly 705. Signals 970 can be sent and received by the remote device 800. Although the signals 970 illustrated in FIG. 9 are wireless signals, in some embodiments the central assembly 705 and a remote device 800 may communicate through a wired connection. The remote device 800 can be, for example, a pager, cell phone, laptop, PDA, tablet, smart phone or other device. The remote device 800 can be operated by a remote system user 810. Some embodiments include a plurality of remote devices 800, which can be operated by a plurality of remote system users 810.

Figure 10:
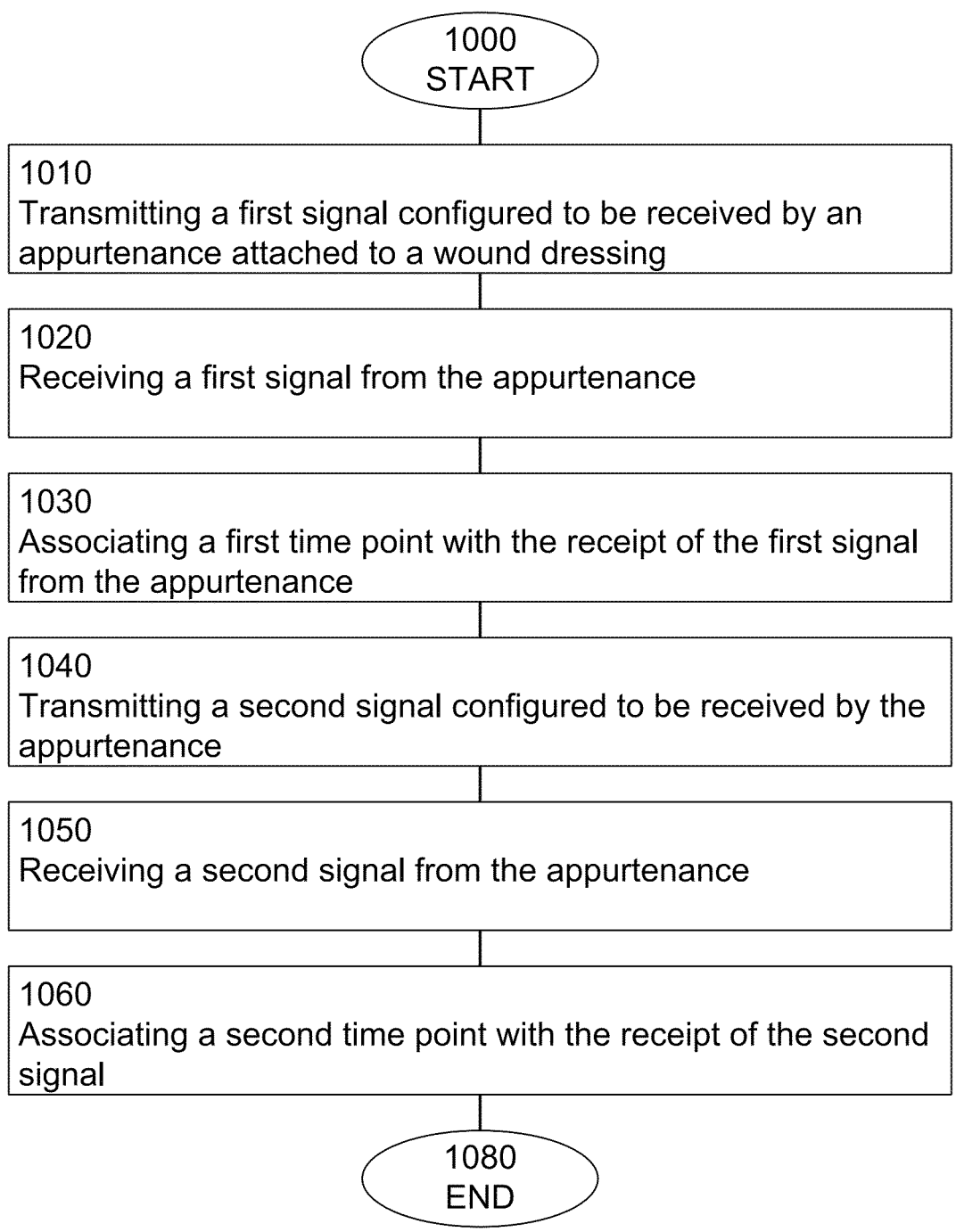
FIG. 10 is a flowchart of a method.

FIG. 10 illustrates aspects of a method utilizing the appurtenances described herein. As shown in FIG. 10, a method of monitoring an appurtenance attached to a wound dressing includes steps. Block 1000 illustrates the start of the method. Block 1010 shows transmitting a first signal configured to be received by an appurtenance attached to a wound dressing. For example, a first signal can be sent from a transmitter unit integral to a local unit. For example, a first signal can be configured in a direction or in a wavelength configured to be received by an appurtenance attached to a wound dressing. Block 1020 depicts receiving a first signal from the appurtenance. For example, the appurtenance can include a passive RFID device and the first signal received from the appurtenance can be the reflected signal from the transmitted first signal configured to be received by the appurtenance. For example, the appurtenance can include circuitry that transmits a signal in response to the receipt of the transmitted first signal. Block 1030 illustrates associating a first time point with the receipt of the first signal from the appurtenance. For example, a first time point can include a clock time point. For example, a first time point can include setting a time counting device to a "start" or "time zero" setting. Block 1040 shows transmitting a second signal configured to be received by the appurtenance. For example, a transmitted second signal can be of the same wavelength as the first transmitted signal. For example, a transmitted second signal can be directed in essentially the same direction as the first transmitted signal. Block 1050 depicts receiving a second signal from the appurtenance. For example, the appurtenance can include a passive RFID device and the second signal received from the appurtenance can be the reflected signal from the transmitted second signal configured to be received by the appurtenance. For example, the appurtenance can include circuitry that transmits a signal in response to the receipt of the transmitted second signal. Block 1060 illustrates associating a second time point with the receipt of the second signal. For example, a second time point can include a clock time point. For example, a second time point can include the elapsed time detected by a time counting device since another time point, such as a "start" or "time zero" setting. Block 1080 shows the end of the method.

A "transmitter unit," as used herein, can be of a variety of units that are configured to send and receive signals, such as signals carried as electromagnetic waves. In embodiments where the appurtenance includes a substrate, the transmission unit can be attached to a surface of the substrate, the transmission unit including circuitry and at least one antenna, the transmission unit configured to transmit a signal. A transmitter unit generally includes at least one antenna and associated circuitry. A transmitter unit can include a transmitter and a receiver. A transmitter unit can include volatile and/or non-volatile memory. A transmitter unit can include a processor. A transmitter unit can include an energy source, such as a battery. In some embodiments of an appurtenance, it is desirable to include a self-compensating antenna, such as described in U.S. Pat. No. 7,055,754 to Forester, titled "Self-Compensating Antennas for Substrates having Differing Dielectric Constant Values," which is incorporated herein by reference. A transmitter unit can be operably connected to a processor. A transmitter unit can be operably connected to a sensor. A transmitter unit can be configured to transmit a signal in response to an interrogation signal. A transmitter unit can include an energy harvesting unit, such as a unit configured to obtain energy from electromagnetic waves. A transmitter unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference herein. A transmitter unit can include an oscillator and encoder configured to generate a programmable pulse position-modulated signal in the radio frequency range. See, for example, U.S. Pat. No. 4,384,288 to Walton, titled "Portable Radio Frequency Emitting Identifier, " which is incorporated herein by reference. A transmitter unit can include a radio frequency identification device (RFID). A transmitter unit can be configured to be a transmitter of signals in the UHF range. A transmitter unit including an RFID device can be configured to transmit signals in the UHF standard range utilized in a global region, as illustrated in the "Worldwide RFID UHF Map" by Intelleflex Corporation (©2009), which is incorporated herein by reference. A transmitter unit can include a radio frequency identification device (RFID), which can be a passive RFID device, a semi-passive RFID device, or an active RFID device, depending on the embodiment. See, for example, Chawla and Ha, "An Overview of Passive RFID," *IEEE Applications and Practice,* 11-17 (September 2007), which is incorporated herein by reference herein. A transmitter unit can include a battery-assisted passive RFID device, such as sold by Alien Technology®, Morgan Hill, Calif., such as described in the brochure from Alien Technology® titled "Battery Assisted Passive Tags" and incorporated herein by reference herein. A transmitter unit can include and optical transmitter unit. A transmitter unit can be configured to transmit at approximately 13.56 megahertz (MHz), or within the ISO 14443 standard parameters. See Patauner et al., "High Speed RFID/NFC at the Frequency of 13.56 MHz," presented at the *First International EURASIP Workshop on RFID Technology*, pages 1-4, 24-25 Sep. 2007, Vienna Austria, which is incorporated herein by reference herein. A transmitter unit can include at least two antennas. A transmitter unit can include a self-compensating antenna system. An antenna can include dielectric material configured to electrically interact with one or more antennas. See, for example, U.S. Pat. No. 7,055,754 to Forester, titled "Self-Compensating Antennas for Substrates Having Differing Dielectric Constant Values," which is incorporated herein by reference. A transmitter unit can include a hybrid backscatter system configured to function in an RFID, IEEE 802.11x standard and Bluetooth system. See, for example, U.S. Pat. No. 7,215,976 to Brideglall, titled "RFID Device, System and Method of Operation Including a Hybrid backscatter-based RFID Protocol Compatible with RFID, Bluetooth and/or IEEE 802.11x Infrastructure," which is incorporated herein by reference. A transmitter unit can be configured to transmit at approximately 131 kilohertz (KHz), for example as part of a RuBee™ (IEEE standard 1902.1) system (sold, for example, by Visible Assets™, Inc). See for example: the description of RuBee™ systems from the Visible Assets™ webpage; Stevens et al., "RuBee (IEEE 1902.1)—The Physics Behind, Real-Time, High Security Wireless Asset Visibility Networks in Harsh Environments," a white paper from Visible Assets™; and in US Patent Application No. 2007/0171076 to Stevens and Waterhouse, titled "Low-frequency Radio Tag Encapsulating System," each of which are incorporated herein by reference. A transmitter unit can include a near field communication (NFC) device. A transmitter unit can include a Wireless Identification and Sensing Platform (WISP) device, manufactured by Intel Corporation, such as described in the "WISP: Wireless Identification and Sensing Platform" webpage (downloaded on Oct. 28, 2011) incorporated herein by reference. A transmitter unit can be operably coupled to a sensor, such as a sensor that detects changes in capacitance (see, e.g. Sample et al., "A Capacitive Touch Interface for Passive RFID Tags," 2009 *IEEE International Conference on RFID*, 103-109 (2009), which is incorporated herein by reference). A transmitter unit can be operably coupled to a sensor, such as described in: Ruhanen et al., "Sensor-enabled RFID Tag and Handbook," from *Building Radio Frequency Identification for the Global Environment* (2008); Sample et al., "Design of an RFID-Based Battery-Free Programmable Sensing Platform," *IEEE Transactions on Instrumentation and Measurement*, vol. 57, no. 11, 2608-2615 (2008); Yeager et al., "Wirelessly-Charged UHF Tags for Sensor Data Collection," 2008 IEEE International Conference on RFID, Apr. 16-17, 2008, pages 320-327; U.S. Pat. Nos. 5,904,671 and 6,348,640 to Navot and Botton, each titled "Tampon Wetness Detection System;" U.S. Pat. No. 7,446,660 to Posamentier titled "Passive Environmental RFID Transceiver;" and U.S. Pat. No. 5,704,352 to Tremblay and Buckles, titled "Implantable Passive Bio-Sensor," which are each incorporated herein by reference. A transmission unit can be operably coupled to a data storage unit, for example as described in U.S. Pat. No. 7,825,776 to Smith and Haehnel, titled "Device Configuration with RFID," and US Patent Application No. 2009/0243813 to Smith at al., titled "Wireless Programming of Non-Volatile Memory with Near-Field UHF Coupling," which are each incorporated herein by reference.

In some embodiments, the transmitter unit can include an acoustic transmitter. For example, a transmitter unit can include a piezoelectric speaker. A variety of suitable piezoelectric speakers are available, including from Murata Manufacturing Co., Ltd., with North American corporate headquarters in Smyrna, Ga. (see, e.g. the Murata catalog titled "Piezoelectric Sounds Components" labeled P37E and dated Jan. 28, 2010, which is incorporated herein by reference). Some embodiments can include acoustic transmitter units such as those manufactured by Advanced Telemetry Systems (headquartered in Isanti, Minn.) for the Pacific Northwest National Laboratory (see, e.g. JSATS Acoustic Transmitter information sheet from the Pacific Northwest National Laboratory, updated March 2010, which is incorporated herein by reference). In some embodiments, an appurtenance can include a piezoelectric speaker configured as part of an acoustic transmitter and also to act as a signaling device (e.g. to generate a beeping noise in response to a signal from the processor).

In some embodiments, the transmitter unit can include an ultrasonic transmitter. In some embodiments, the transmitter unit can include an ultrasonic transducer. Multiple examples of ultrasonic transmitters and transducers are commercially available, often marketed under the term "ultrasonic sensors" as it is used in the industry (see, e.g. the Murata catalog titled "Ultrasonic Sensor" labeled 515E and dated Oct. 31, 2008, which is incorporated herein by reference). The transmitter unit can be configured as part of an ultrasonic ranging system. See: Wang, "A Design Method of Ultrasonic Ranging System with High Accuracy," *Journal of Computational Information Systems*, 7: 7 pages 2444-2451 (2011), which is incorporated herein by reference. The transmitter unit can be configured to communicate with an ultrasonic communication system. See: Chen and Wu, "Ultrasonic System with Infrared Communication Technology," *Journal of Computers*, vol. 6, no. 11, pages 2468-2475 (2011), which is incorporated herein by reference.

In some embodiments, the transmitter unit can include an optical transmitter. For example, an optical transmitter unit can include one or more white light emitting diodes (LEDs). For example, an optical transmitter unit can include an infrared laser. In some embodiments, optical transmitter units can be desirable to minimize interference from nearby electrical equipment, such as medical equipment. See: Kavehrad, "Sustainable Energy-Efficient Wireless Applications Using Light," *IEEE Communications Magazine*, vol. 48, no. 12, pages 66-73, (2010); and Fadlullah and Kavehrad, "Indoor High-Bandwidth Optical Wireless Links for Sensor Networks" *Journal of Lightwave Technology*, vol. 28, no. 21, pages 3086-3094 (2010), which are incorporated herein by reference.

Figure 11:
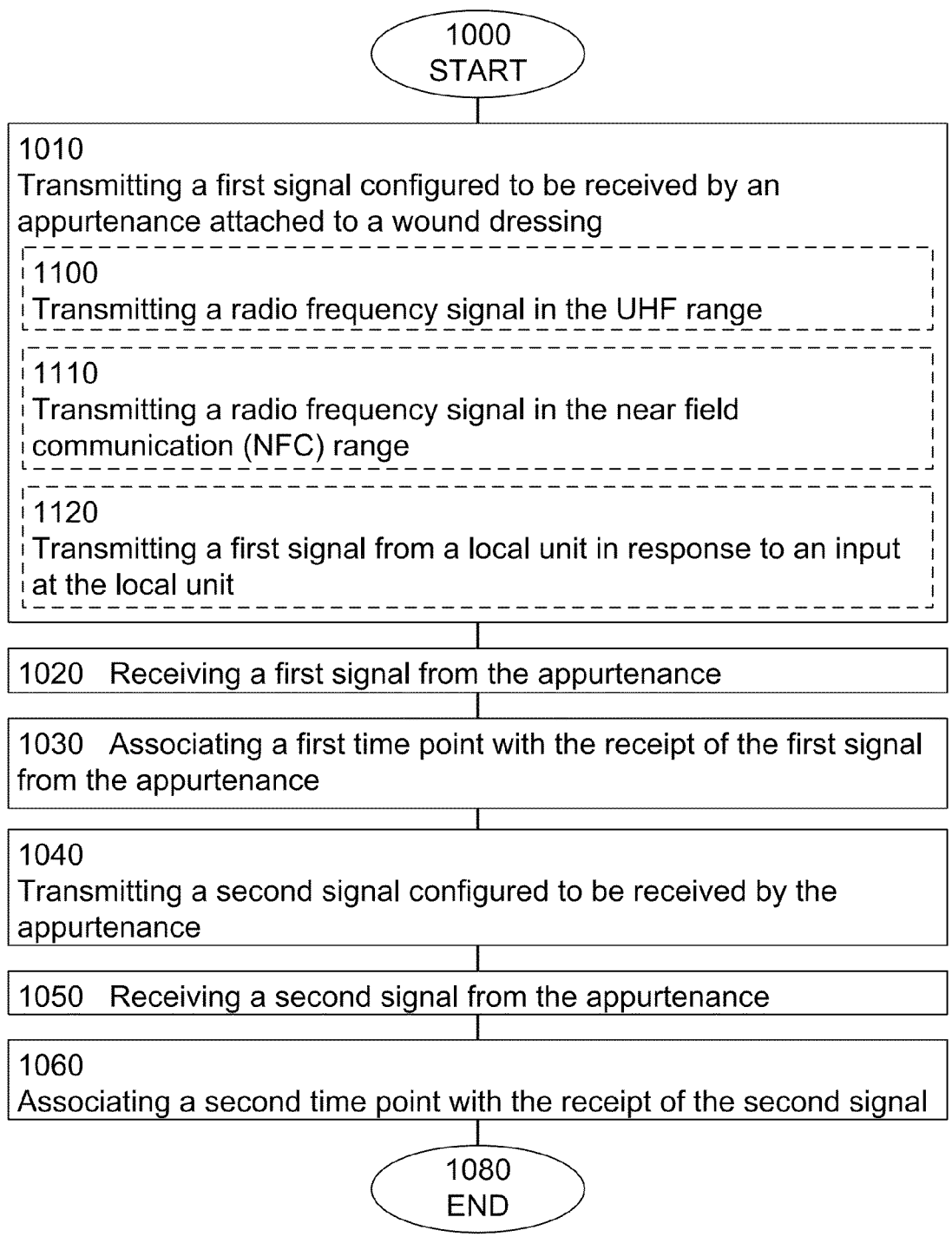
FIG. 11 is a flowchart illustrating aspects of a method such as shown in FIG. 10.

FIG. 11 illustrates aspects of the method depicted in FIG. 10. FIG. 11 illustrates that in some embodiments, block 1010 can include one or more of optional blocks 1100, 1110, and 1120. For example, transmitting a first signal configured to be received by an appurtenance attached to a wound dressing, as shown in block 1010, can include transmitting a radio frequency signal in the UHF range, as illustrated in block 1100. Block 1100 illustrates transmitting a radio frequency signal in the UHF range. The UHF range signal can include, for example, a transmitted signal in the 902-928 MHz range. FIG. 11 also illustrates that block 1010 can include optional block 1110. Block 1110 depicts transmitting a radio frequency signal in the near field communication (NFC) range.

For example, transmitting a radio frequency signal in the NFC range can include transmitting a signal in the ISO/IEC 14443 standard range. For example, transmitting a radio frequency signal in the NFC range can include transmitting a signal in an approximate range of 13.56 MHz. FIG. 11 also shows that block 1010 can include optional block 1120. Block 1120 depicts transmitting a first signal from a local unit in response to an input at the local unit. For example, transmitting a first signal from a local unit can be in response to a user pushing a button on the local unit. For example, transmitting a first signal from a local unit can be in response to a user touching a touchscreen on the local unit.

Figure 12:
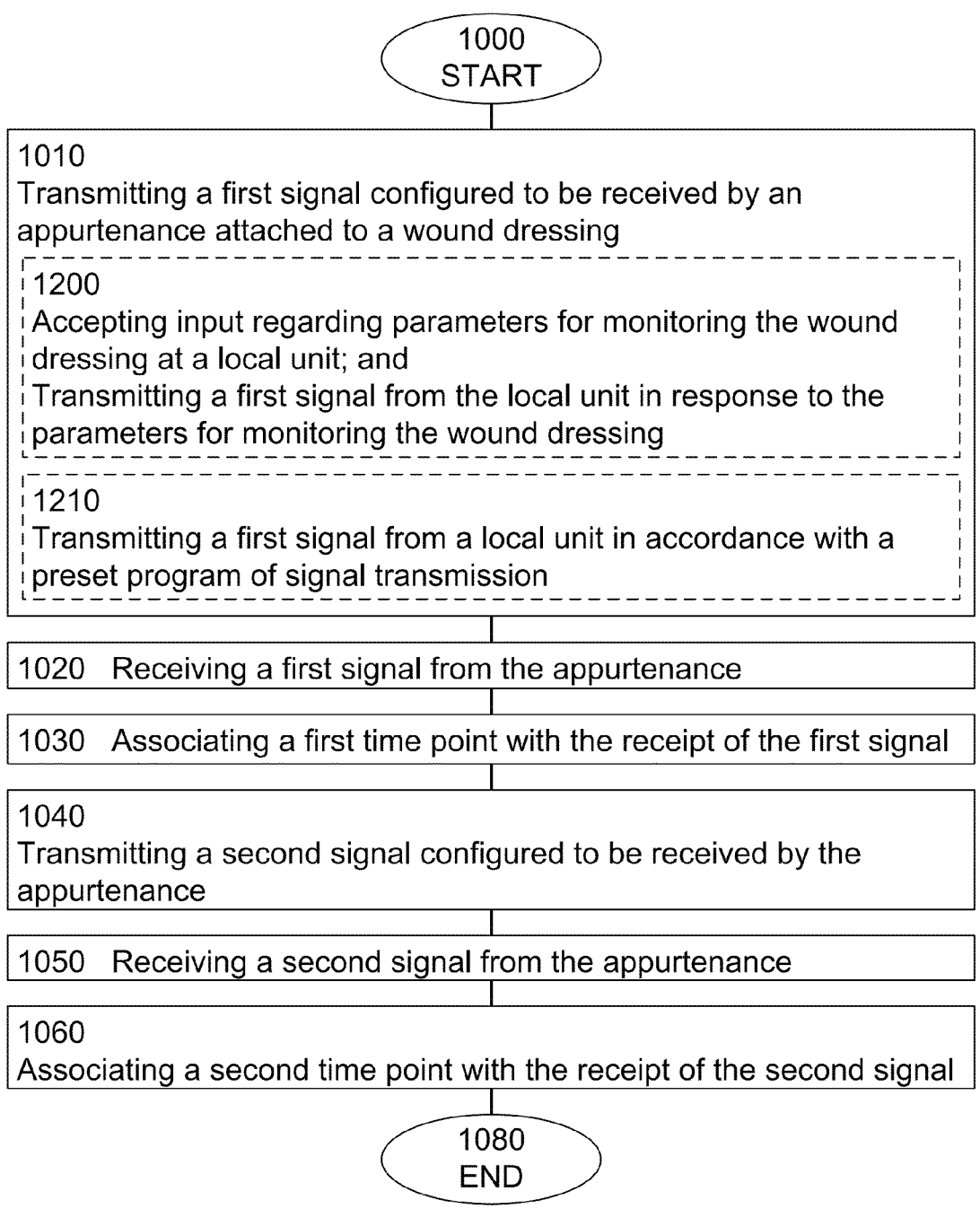
FIG. 12 is a flowchart showing aspects of a method such as displayed in FIG. 10.

FIG. 12 shows aspects of the method depicted in FIG. 10. FIG. 12 depicts that in some embodiments, block 1010 can include one or more of optional blocks 1200 and 1210. Block 1200 illustrates accepting input regarding parameters for monitoring the wound dressing at a local unit; and transmitting a first signal from the local unit in response to the parameters for monitoring the wound dressing. For example, a local unit may accept input from a user that the wound dressing should be monitored every hour, and the first signal transmitted from the local unit at the end of the first hour. Block 1210 depicts transmitting a first signal from a local unit in accordance with a preset program of signal transmission. For example, a local unit can be preset to send a signal every 10 minutes, and the first signal can be transmitted 10 minutes after the local unit is turned on.

Figure 13:
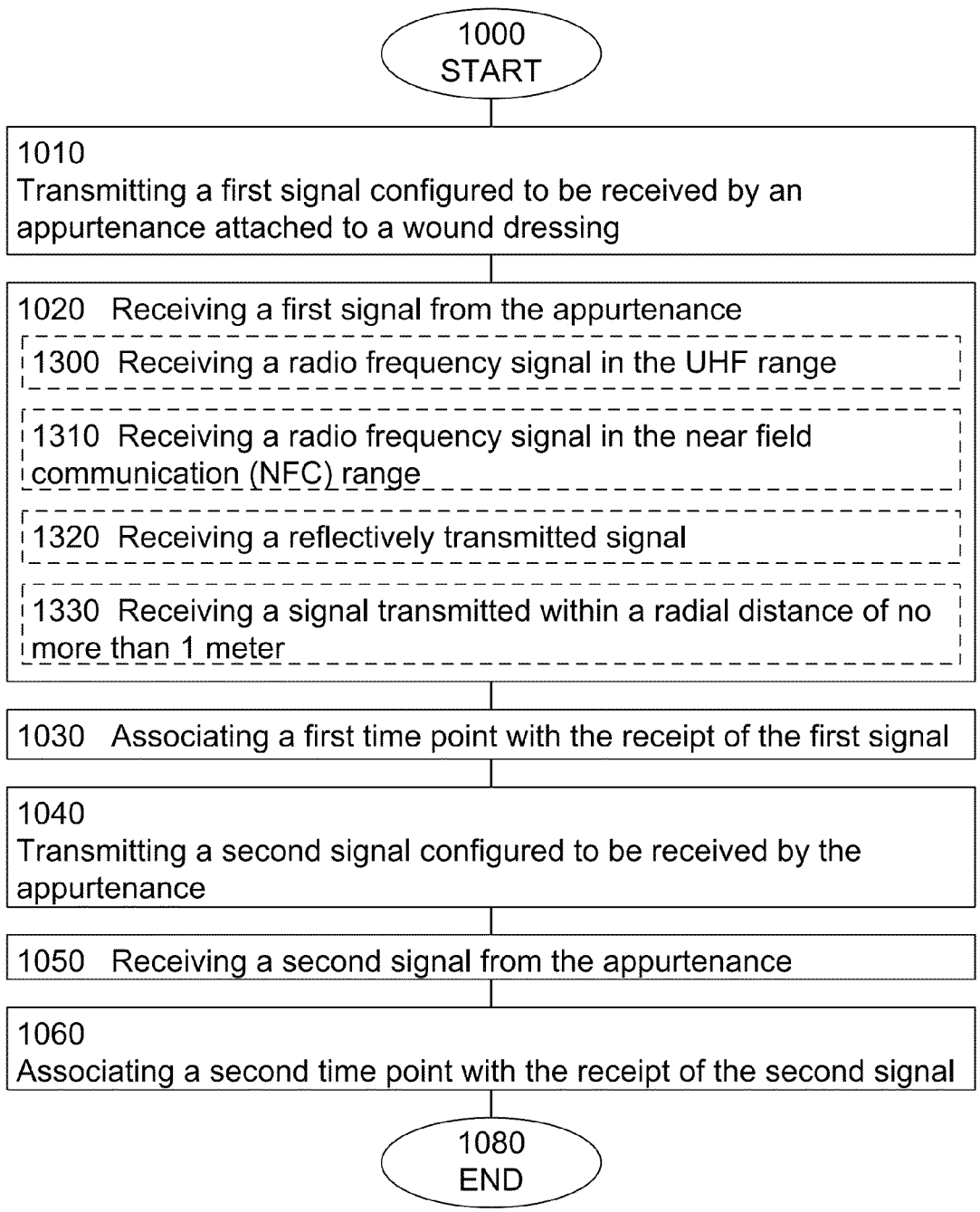
FIG. 13 is a flowchart illustrating aspects of a method such as shown in FIG. 10.

FIG. 13 illustrates aspects of the method depicted in FIG. 10. FIG. 13 shows that in some embodiments, block 1020 can include one or more of optional blocks 1300, 1310, 1320 and 1330. Block 1020 depicts receiving a first signal from the appurtenance. FIG. 13 illustrates that block 1020 can include block 1300, showing receiving a radio frequency signal in the UHF range. Block 1020 can include block 1310, depicting receiving a radio frequency signal in the near field communication (NFC) range. Block 1020 can include block 1320, showing receiving a reflectively transmitted signal. For example, the appurtenance can include an RFID device. Block 1020 can include block 1330, depicting receiving a signal transmitted within a radial distance of no more than 1 meter. For example, several of the transmission technologies described herein are of effective limited range, such as within a radial distance of no more than 1 meter, or not more than 2 meters, or no more than 3 meters.

Figure 14:
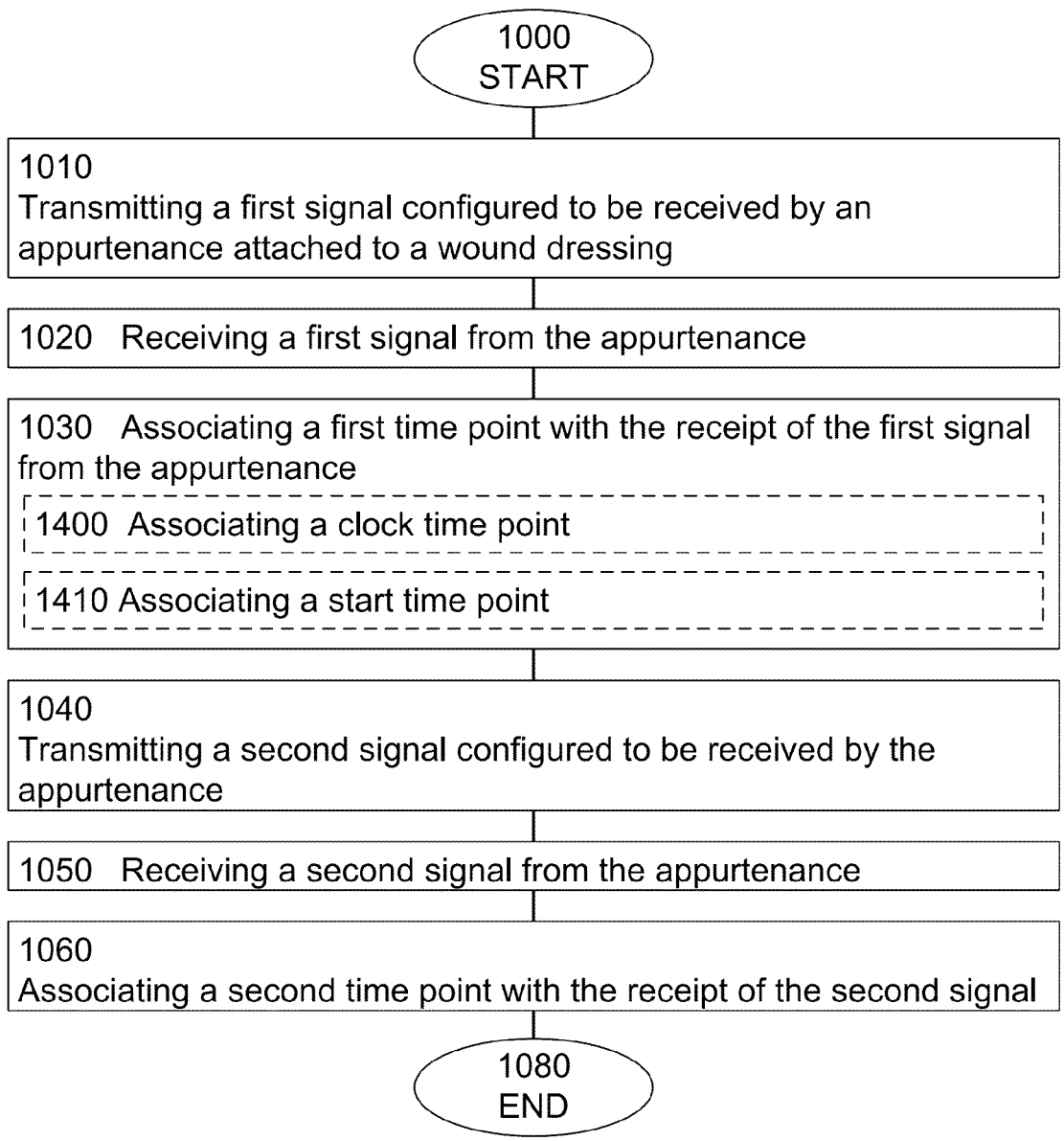
FIG. 14 is a flowchart showing aspects of a method such as illustrated in FIG. 10.

FIG. 14 depicts aspects of the method depicted in FIG. 10. FIG. 13 shows that in some embodiments, block 1030 can include one or more of optional blocks 1400 and 1410. Block 1030 illustrates associating a first time point with the receipt of the first signal from the appurtenance. Block 1030 can include block 1400, illustrating associating a clock time point. For example, associating a clock time point can include associating a specific time and date, such as 14:56 on Dec. 20, 2011. For example, associating a clock time point can include associating an elapsed clock time point, such as 1 hour since the system was activated relative to a given appurtenance. Block 1030 can include block 1410, showing associating a start time point.

Figure 15:
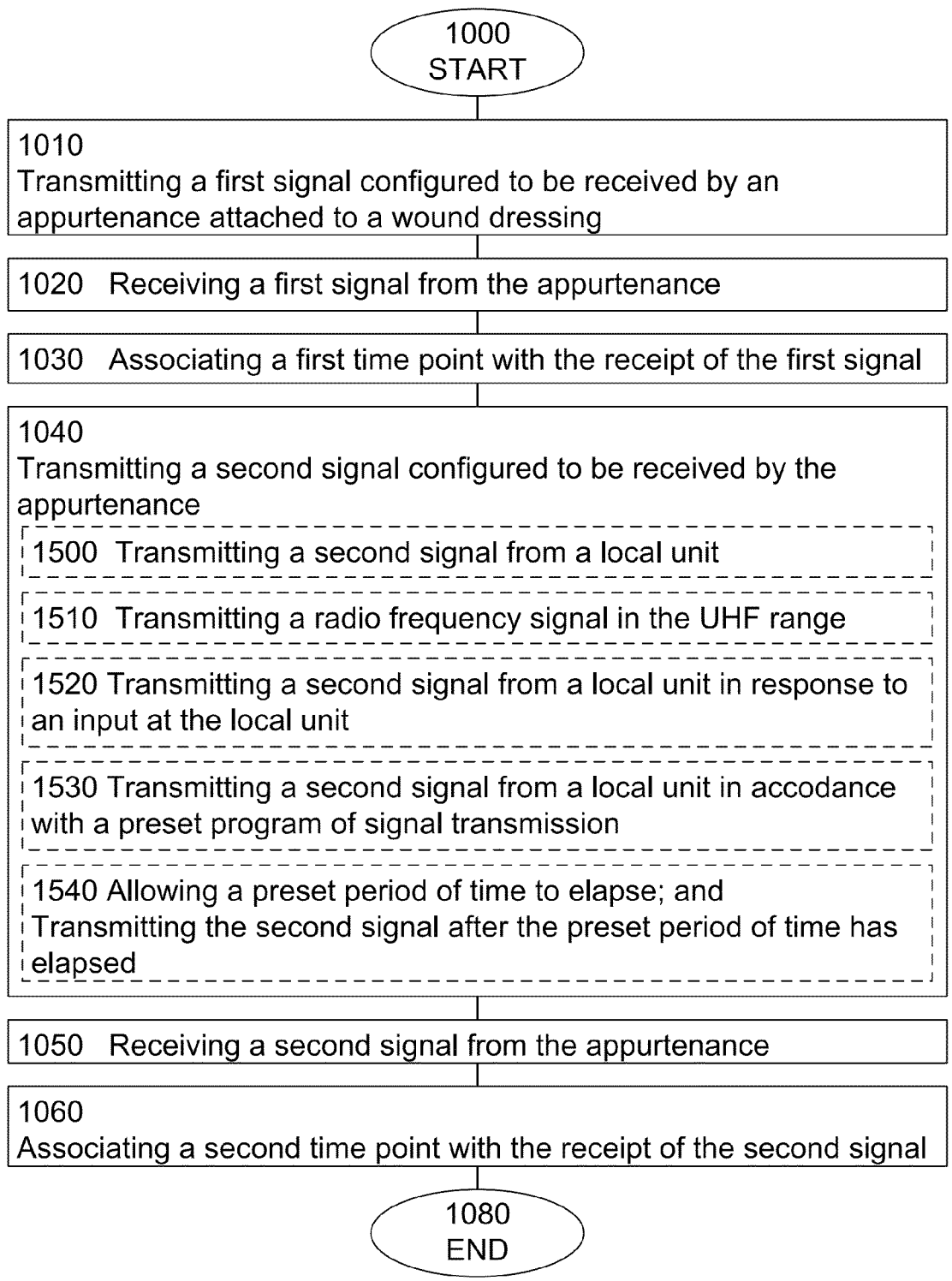
FIG. 15 is a flowchart illustrating aspects of a method such as shown in FIG. 10.

FIG. 15 shows aspects of the method depicted in FIG. 10. FIG. 15 shows that in some embodiments, block 1040 can include one or more of optional blocks 1500, 1510, 1520, 1530 and 1540. Block 1040 shows transmitting a second signal configured to be received by the appurtenance. Block 1500 illustrates transmitting a second signal from a local unit. Block 1510 shows transmitting a radio frequency signal in the UHF range. Block 1520 depicts transmitting a second signal from a local unit in response to an input at the local unit. For example, transmitting a second signal can be in response to a user entering a command on the keyboard of a local unit. Block 1530 shows transmitting a second signal from a local unit in accordance with a preset program of signal transmission. For example, a local unit may have a preset program for transmitting a signal configured to be received by the appurtenance every 10 minutes. Block 1540 illustrates allowing a preset period of time to elapse; and transmitting the second signal after the preset period of time has elapsed. For example, a preset period of time can be every half-hour, and so the second signal can be transmitted after a half hour has elapsed since the last transmission.

Figure 16:
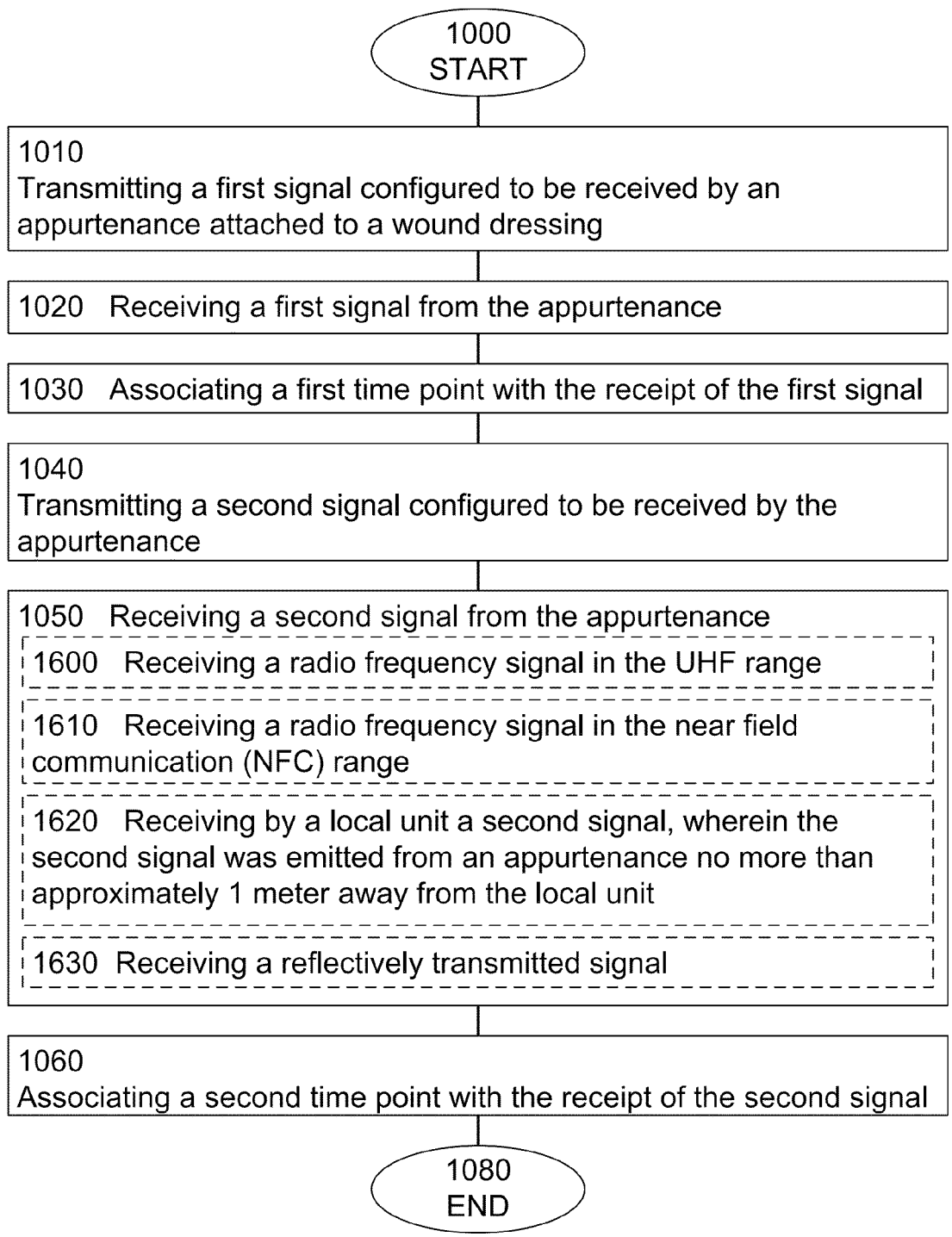
FIG. 16 is a flowchart displaying aspects of a method such as illustrated in FIG. 10.

FIG. 16 shows aspects of the method depicted in FIG. 10. FIG. 16 shows that in some embodiments, block 1050 can include one or more of optional blocks 1600, 1610, 1620 and 1630. Block 1050 depicts receiving a second signal from the appurtenance. Block 1050 can include optional block 1600. Block 1600 illustrates receiving a radio frequency signal in the UHF range. Block 1610 depicts receiving a radio frequency signal in the near field communication (NFC) range. Block 1620 shows receiving by a local unit a second signal, wherein the second signal was emitted from an appurtenance no more than approximately 1 meter away from the local unit. Block 1630 illustrates receiving a reflectively transmitted signal.

Figure 17:
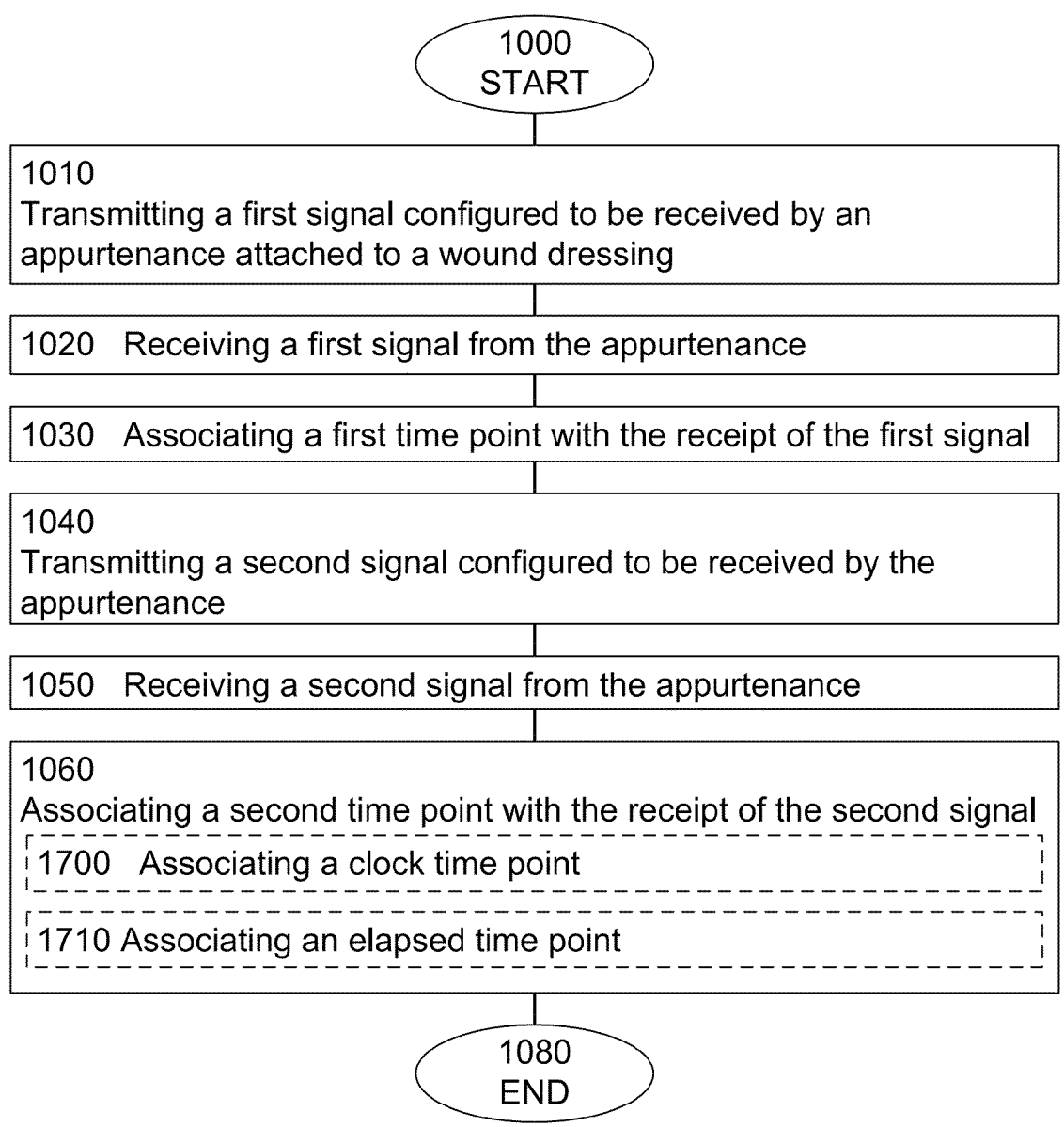
FIG. 17 is a flowchart illustrating aspects of a method such as shown in FIG. 10.

FIG. 17 illustrates aspects of the method depicted in FIG. 10. FIG. 17 depicts that in some embodiments, block 1060 can include one or more of optional blocks 1700 and 1710. Block 1060 illustrates associating a second time point with the receipt of the second signal. Block 1700 illustrates associating a clock time point. For example, a clock time point, such as 17:50, can be associated with the receipt of the second signal. Block 1710 shows associating an elapsed time point. For example, an amount of elapsed time since the receipt of the first signal can be associated with the receipt of the second signal.

Figure 18:
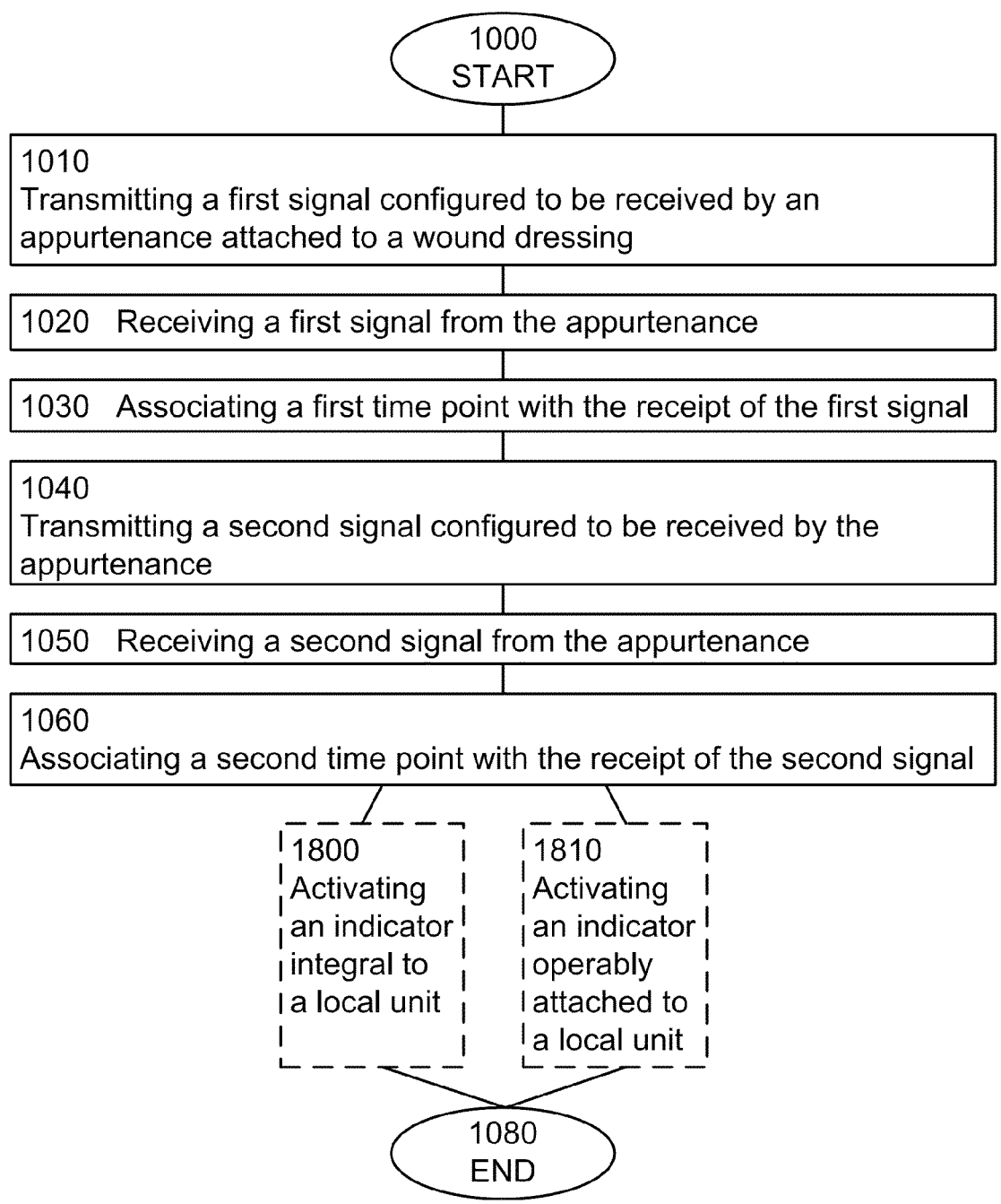
FIG. 18 is a flowchart showing aspects of a method such as displayed in FIG. 10.

FIG. 18 depicts further aspects of the method shown in FIG. 10. FIG. 18 shows that in some embodiments, the flowchart illustrated in FIG. 10 can include one or more optional blocks 1800 and 1810. Block 1800 shows activating an indicator integral to a local unit. For example, an LED indicator integral to a local unit can be illuminated. For example, a vibration emitter integral to a local unit can be activated. Block 1810 depicts activating an indicator operably attached to a local unit. For example, an LED indicator operably attached to a local unit can be illuminated. For example, a vibration emitter operably attached to a local unit can be activated.

Figure 19:
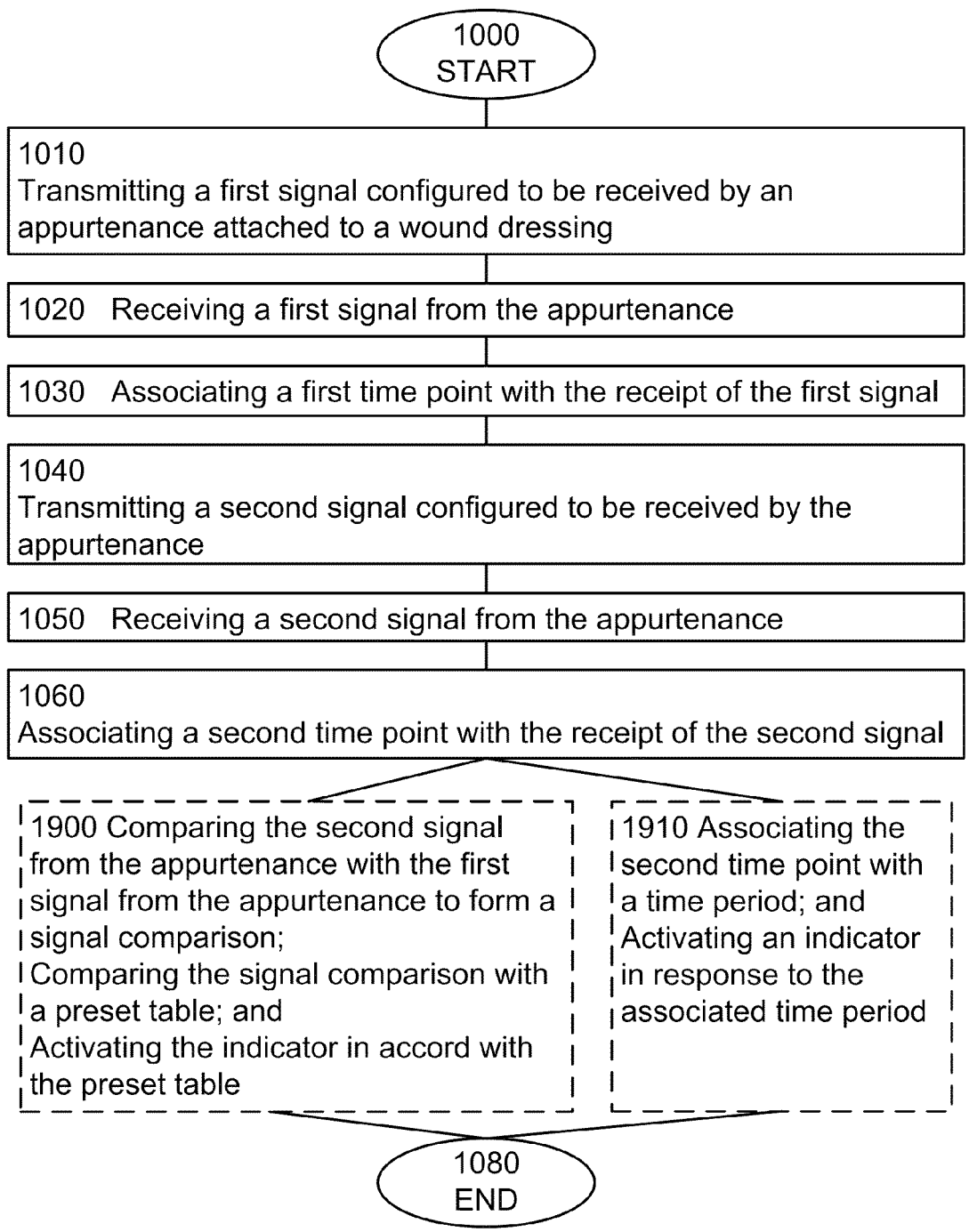
FIG. 19 is a flowchart illustrating aspects of a method such as shown in FIG. 10.

FIG. 19 depicts further aspects of the method shown in FIG. 10. FIG. 19 shows that in some embodiments, the flowchart illustrated in FIG. 10 can include one or more optional blocks 1900 and 1910. Block 1900 illustrates comparing the second signal from the appurtenance with the first signal from the appurtenance to form a signal comparison; comparing the signal comparison with a preset table; and activating an indicator in accord with the preset table. For example, a preset table can be a "look-up" table. For example, a preset table can include a range of preset signal comparison values predetermined to be sufficiently significant to notify a caregiver through activating an indicator on the local unit. Block 1910 shows associating the second time point with a time period; and activating an indicator in response to the associated time period. For example, a time period can be a predetermined time period between manual checks by a caregiver. For example, a time period can be a predetermined time period that a wound dressing with an affixed appurtenance should be in place before it is changed. For example, a time period can be one day, two days, or three days.

Figure 20:
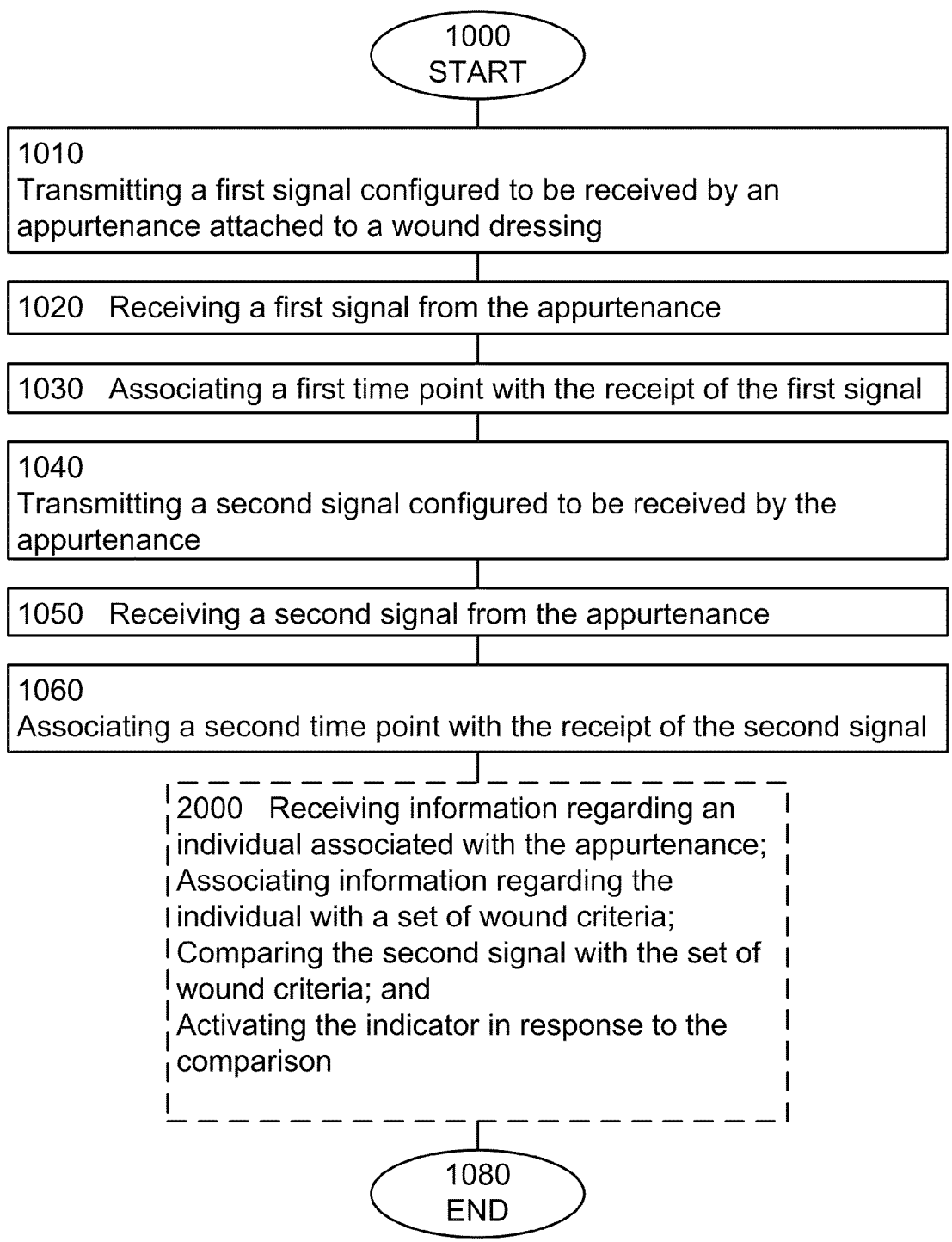
FIG. 20 is a flowchart illustrating aspects of a method such as shown in FIG. 10.

FIG. 20 shows further aspects of the method shown in FIG. 10. FIG. 20 illustrates that in some embodiments, the flowchart illustrated in FIG. 10 can include optional block 2000. Block 2000 shows receiving information regarding an individual associated with the appurtenance; associating information regarding the individual with a set of wound criteria; comparing the second signal with the set of wound criteria; and activating an indicator in response to the comparison. For example, the system may receive information that a particular individual is at risk for developing infection, and associate the risk of infection with an elevated temperature. If the second signal includes information indicating that the temperature of the wound dressing is elevated between the first and second signal, an indicator on the local unit can be activated. For example, the system may receive information that a particular individual has an acute wound from a surgical intervention, and associate the information with a risk of bleeding. If the second signal includes information indicating that the moisture content of the wound dressing is elevated between the first and second signal, an indicator on the local unit can be activated.

Figure 21:
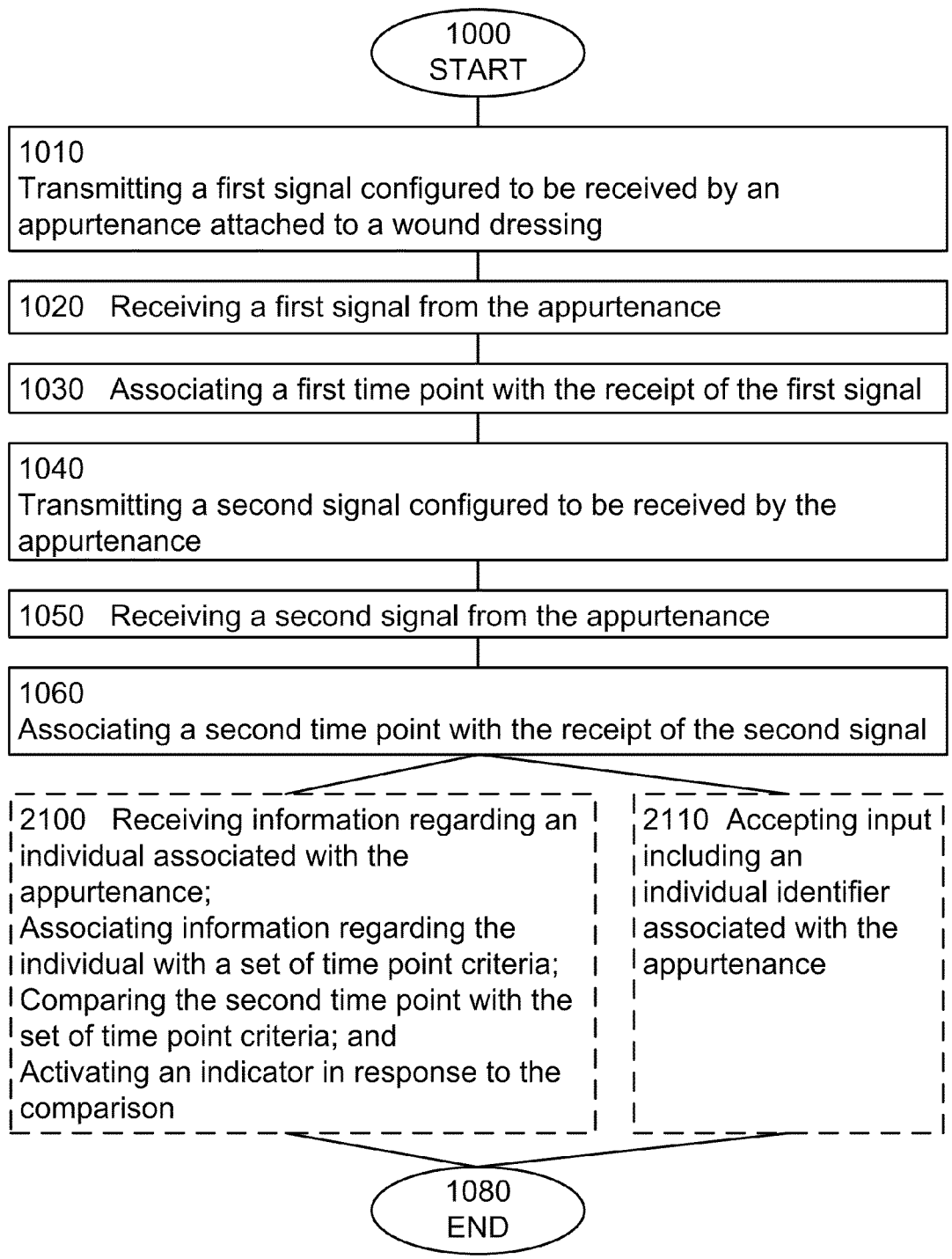
FIG. 21 is a flowchart showing aspects of a method such as displayed in FIG. 10.

FIG. 21 shows further aspects of the method shown in FIG. 10. FIG. 21 illustrates that in some embodiments, the flowchart illustrated in FIG. 10 can include one or more of optional blocks 2100 and 2110. Block 2100 shows receiving information regarding an individual associated with the appurtenance; associating information regarding the individual with a set of time point criteria; comparing the second time point with the set of time point criteria; and activating an indicator in response to the comparison. For example, a system may receive information that an individual's wound dressing includes an epithelial growth factor, and associate that information with the criteria that wound dressings including an epithelial growth factor should be changed every 48 hours. The system may compare the second time point with this set of time point criteria, and activate the indicator when 48 hours has elapsed. Block 2110 shows accepting input including an individual identifier associated with the appurtenance. For example, the system may accept input typed into the local unit by a user identifying the patient, the region of the body covered by the wound dressing, the type of wound dressing, or the caregiver who applied the wound dressing with the affixed appurtenance to the individual. For example, the system may accept input obtained by the local unit transmitting an RFID signal to a patient identification bracelet including an RFID tag and receiving the corresponding reflectively-transmitted signal including a specific identification code from the identification bracelet including an RFID tag worn by the patient.

Figure 22:
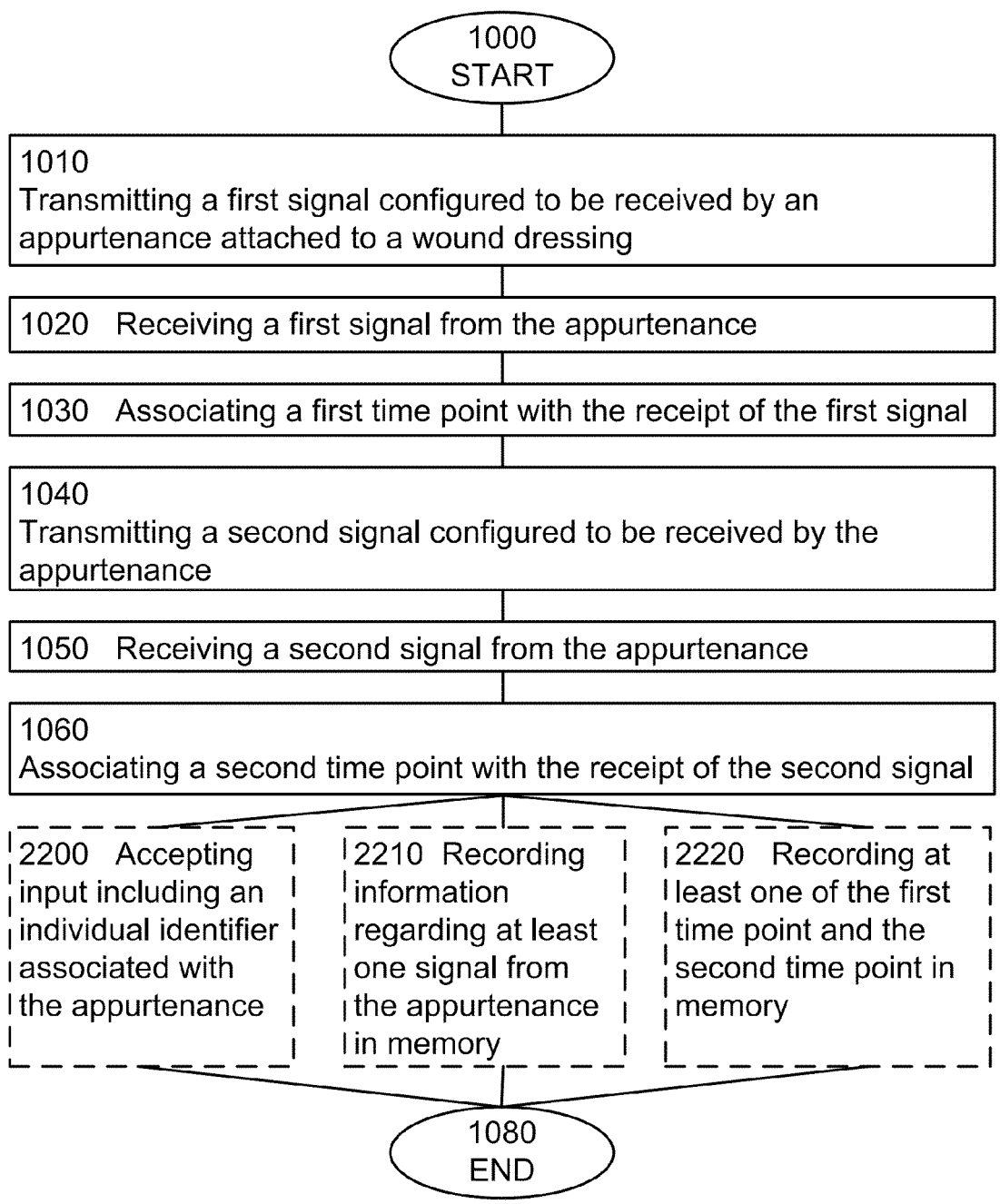
FIG. 22 is a flowchart illustrating aspects of a method such as shown in FIG. 10.

FIG. 22 illustrates aspects of the method shown in FIG. 10. FIG. 22 shows that in some embodiments, the flowchart illustrated in FIG. 10 can include one or more of optional blocks 2200, 2210 and 2220. Block 2200 illustrates accepting input including an individual identifier associated with the appurtenance. For example, the appurtenance can include a preset individual identifier for that specific appurtenance. For example, a system user may give an appurtenance an individual identifier when the appurtenance is affixed to a wound dressing. Block 2210 shows recording information regarding at least one signal from the appurtenance in memory. For example, the time a signal is received can be recorded in memory at a local unit. For example, information contained in a signal can be recorded in memory at a local unit. Block 2220 shows recording at least one of the first time point and the second time point in memory. For example, the first time point can be recorded in non-volatile memory at the local unit. For example, the second time point can be recorded in non-volatile memory at the local unit.

Figure 23:
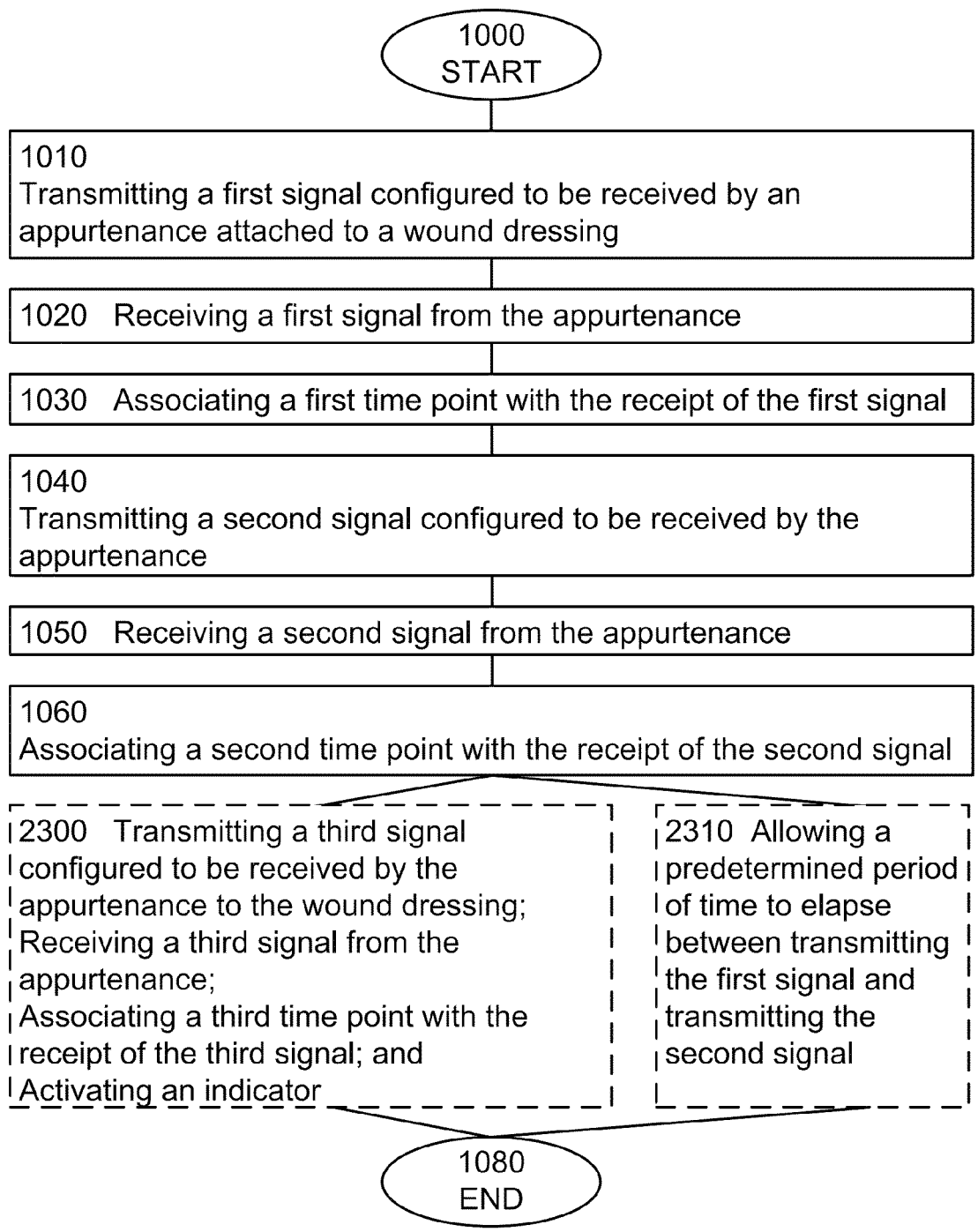
FIG. 23 is a flowchart illustrating aspects of a method such as shown in FIG. 10.

FIG. 23 shows aspects of the method shown in FIG. 10. FIG. 23 illustrates that in some embodiments, the flowchart depicted in FIG. 10 can include one or more of optional blocks 2300 and 2310. Block 2300 shows transmitting a third signal configured to be received by the appurtenance to the wound dressing; receiving a third signal from the appurtenance; associating a third time point with the receipt of the third signal; and activating an indicator. For example, a system may monitor an appurtenance affixed to a wound dressing for a longer period than allotted by two signals, and therefore at least a third signal can be required. Block 2310 shows allowing a predetermined period of time to elapse between transmitting the first signal and transmitting the second signal. For example, a local unit may allow 30 minutes to elapse between transmitting the first signal and transmitting the second signal. For example, a local unit may allow 1 hour to elapse between transmitting the first signal and transmitting the second signal.

Figure 24:
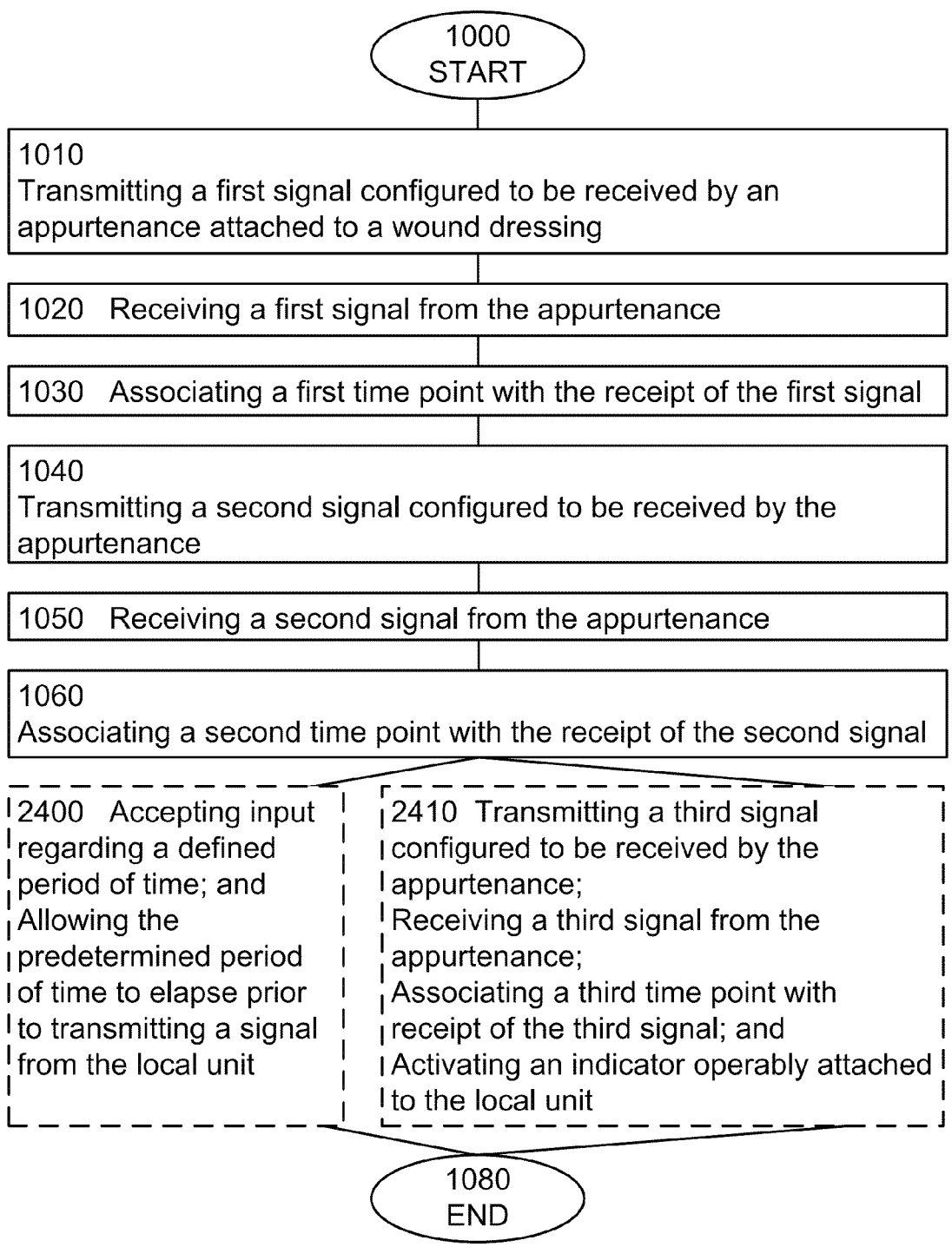
FIG. 24 is a flowchart showing aspects of a method such as displayed in FIG. 10.

FIG. 24 illustrates aspects of the method shown in FIG. 10. FIG. 24 shows that in some embodiments, the flowchart depicted in FIG. 10 can include one or more of optional blocks 2400 and 2410. Block 2400 depicts accepting input regarding a defined period of time; and allowing the defined period of time to elapse prior to transmitting a signal from the local unit. For example, the local unit can be pre-programmed to send a signal after 30 minutes. For example, the local unit can be pre-programmed to send a signal every hour. For example, the local unit can be pre-programmed to send a signal after 15 minutes has elapsed. Block 2410 illustrates transmitting a third signal configured to be received by the appurtenance; receiving a third signal from the appurtenance; associating a third time point with the receipt of the third signal; and activating an indicator operably attached to the local unit.

Figure 25:
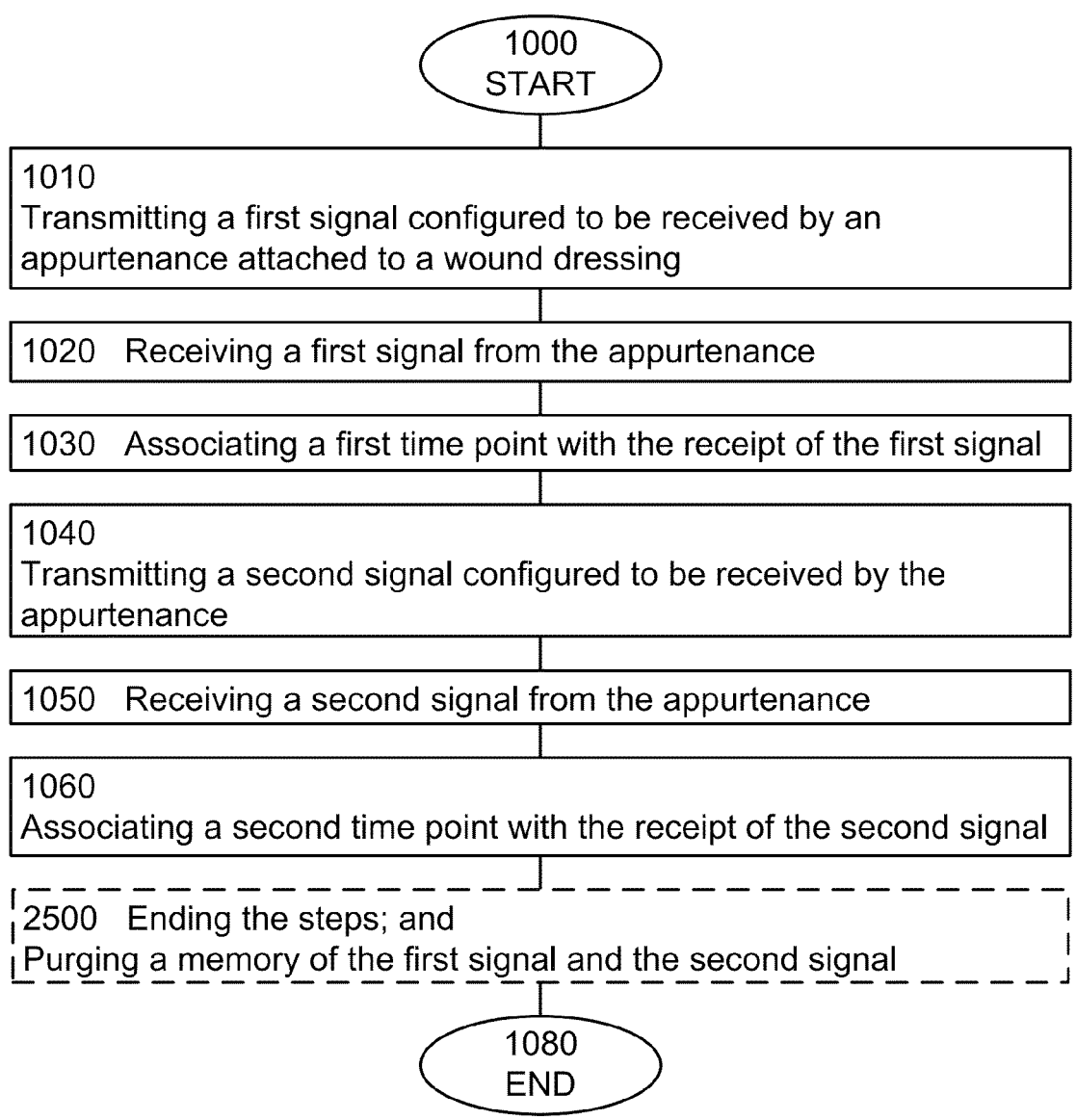
FIG. 25 is a flowchart illustrating aspects of a method such as shown in FIG. 10.

FIG. 25 depicts aspects of the method shown in FIG. 10. FIG. 25 shows that in some embodiments, the flowchart depicted in FIG. 10 can include optional block 2500. Block 2500 illustrates ending the steps; and purging a memory of the first signal and the second signal. For example, a local unit may receive input to end the monitoring of a particular wound dressing-appurtenance unit, which can be removed for disposal, and the local unit purged of the memory of the first signal and the second signal.

Figure 26:
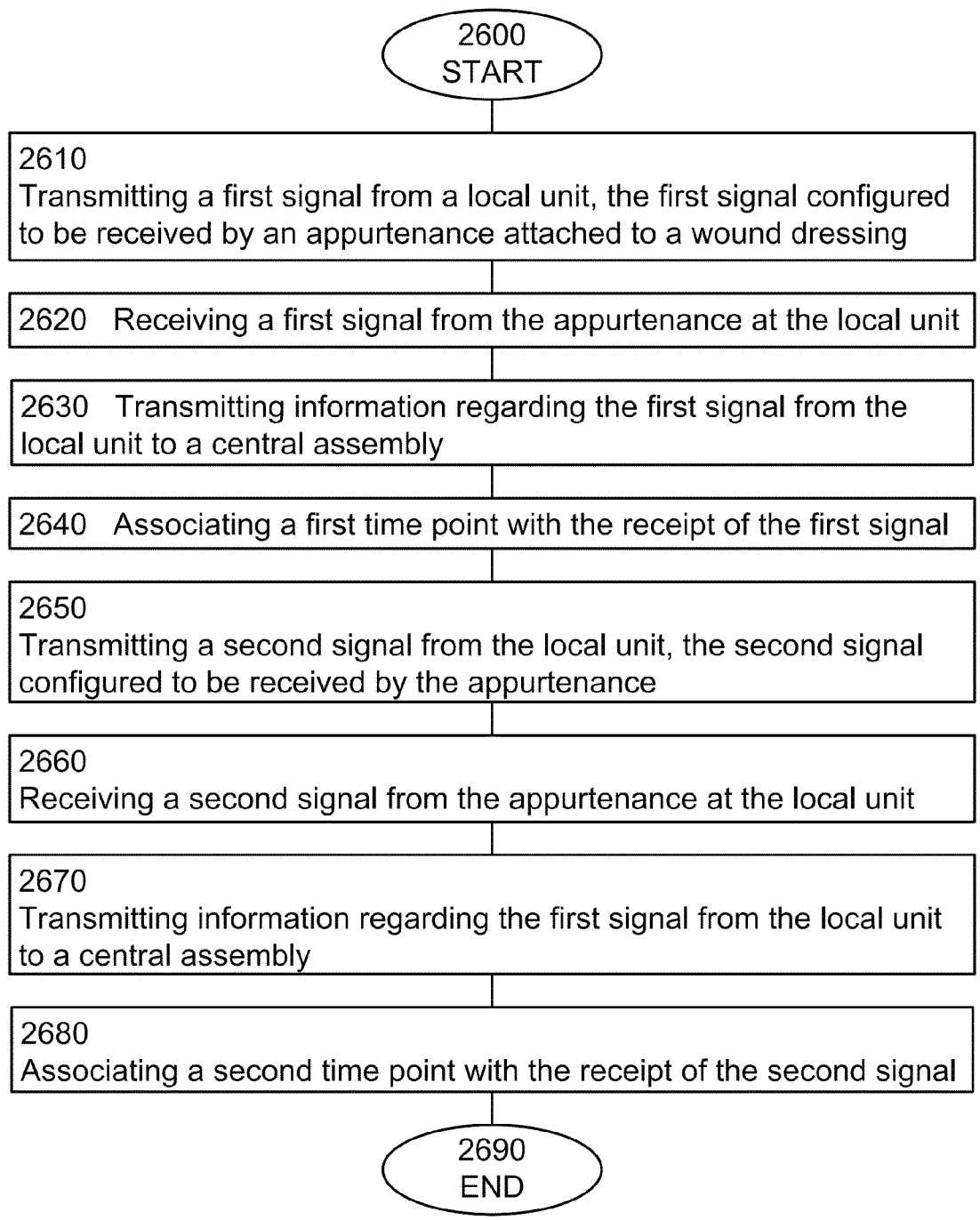
FIG. 26 is a flowchart of a method.

FIG. 26 illustrates aspects of a method of monitoring an appurtenance attached to a wound dressing. The method of monitoring an appurtenance attached to a wound dressing as depicted by the flowchart in FIG. 26 relates to a local unit. The flowchart illustrates that the method includes steps. Block 2600 shows the start of the method. Block 2610 depicts transmitting a first signal from a local unit, the first signal configured to be received by an appurtenance attached to a wound dressing. For example, a first signal can be transmitted from a local unit in a signal type configured to be received by an appurtenance, such as an appurtenance including a RFID unit that can be configured to receive a UHF signal in the range of 902-928 MHz. For example, a signal can be transmitted from a local unit in a direction and at a distance configured so that the signal can be received by an appurtenance. Block 2620 illustrates receiving a first signal from the appurtenance at the local unit. For example, a local unit may receive a first signal transmitted from the appurtenance. For example, a local unit may receive a first signal reflectively radiated from a RFID unit within the appurtenance. Block 2630 shows transmitting information regarding the first signal from the local unit to a central assembly. For example, a local unit may transmit to a central assembly information regarding when it sent the first signal. For example, a local unit may transmit to a central assembly information regarding the received first signal from the appurtenance. Block 2640 illustrates associating a first time point with the receipt of the first signal. For example, a local unit may associate a clock time point with the receipt of the first signal from the appurtenance. For example, a local unit may associate an elapsed time point with the receipt of the first signal from the appurtenance. Block 2650 depicts transmitting a second signal from the local unit, the second signal configured to be received by the appurtenance. For example, the second signal transmitted from the local unit can be of the same frequency as the first signal transmitted from the local unit. For example, the second signal transmitted from the local unit can be positioned in approximately the same direction as the first signal transmitted from the local unit. Block 2660 shows receiving a second signal from the appurtenance at the local unit. For example, a local unit may receive a second signal from the appurtenance of a substantially similar frequency as the first signal received from the appurtenance. Block 2670 depicts transmitting information regarding the first signal from the local unit to a central assembly. For example, a local unit may transmit the time and information regarding a first signal to a central assembly. For example, a local unit may transmit information regarding the appurtenance source to a central assembly. Block 2680 shows associating a second time point with the receipt of the second signal. For example, a local unit may associate a clock time point with the receipt of the second signal. For example, a local unit may associate an elapsed time point with the receipt of the second signal, such as the elapsed time since the first signal was received. Block 2690 illustrates the end of the method.

Figure 27:
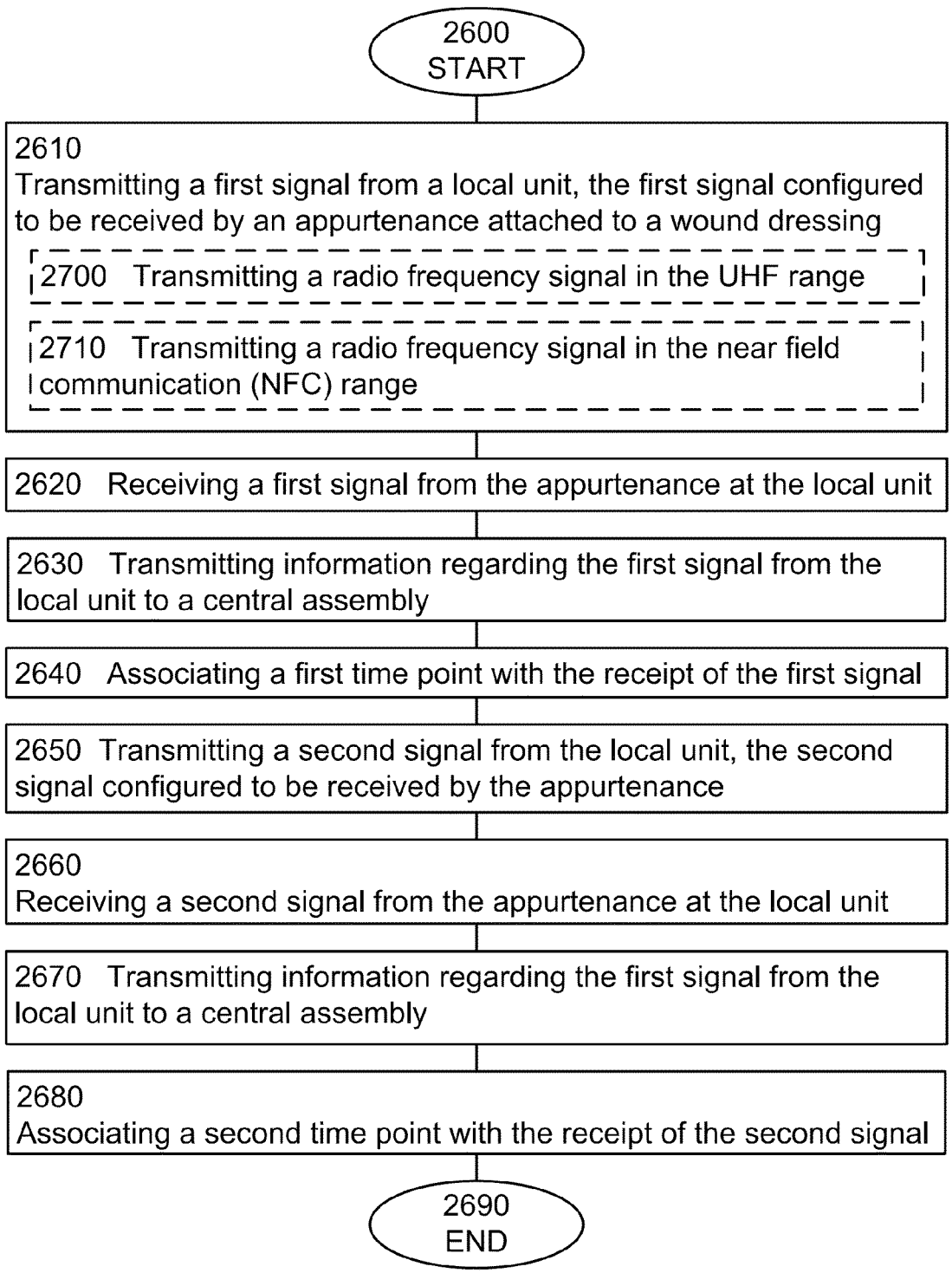
FIG. 27 is a flowchart illustrating aspects of a method such as shown in FIG. 26.

FIG. 27 shows aspects of the flowchart illustrated in FIG. 26. FIG. 27 shows that in some embodiments, the flowchart can include one or more of optional blocks 2700 and 2710. Block 2610, illustrating transmitting a first signal from a local unit, the first signal configured to be received by an appurtenance attached to a wound dressing, can include one or more of optional blocks 2700 and 2710. Block 2700 shows transmitting a radio frequency signal in the UHF range. For example, a signal can be transmitted in the 902-928 MHz range. Block 2710 shows transmitting a radio frequency signal in the near field communication (NFC) range. For example, transmitting a radio frequency signal in the NFC range can include transmitting a signal in the ISO/IEC 14443 standard range. For example, transmitting a radio frequency signal in the NFC range can include transmitting a signal in an approximate range of 13.56 MHz.

Figure 28:
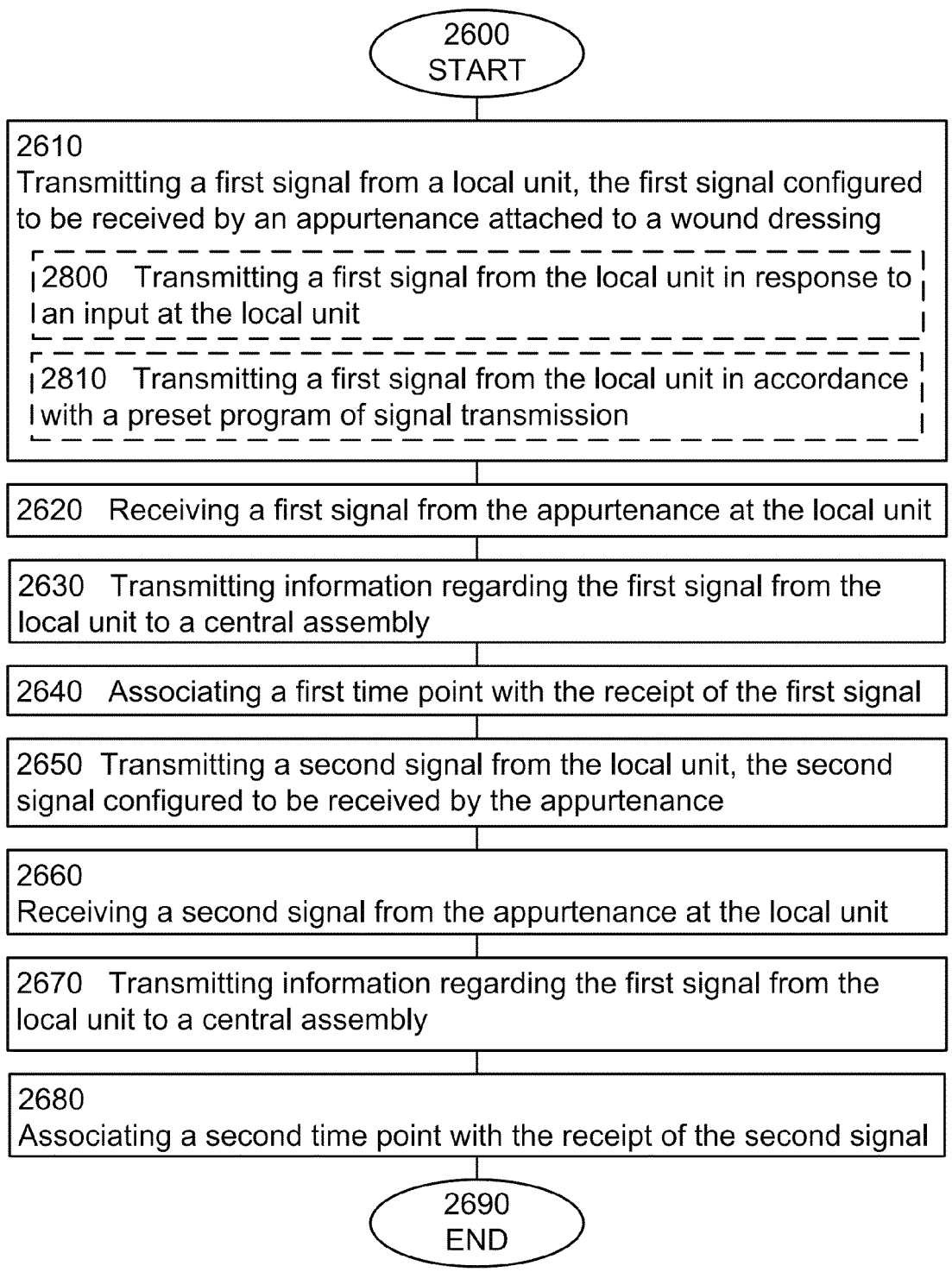
FIG. 28 is a flowchart showing aspects of a method such as displayed in FIG. 26.

FIG. 28 illustrates aspects of the flowchart shown in FIG. 26. FIG. 28 illustrates that, in some embodiments, block 2610 can include one or more of blocks 2800 and 2810. Block 2610 illustrates transmitting a first signal from a local unit, the first signal configured to be received by an appurtenance attached to a wound dressing. Block 2800 shows transmitting a first signal from the local unit in response to an input at the local unit. For example, a user may input a command, such as by pushing buttons integral to the local unit, which initiates transmitting a first signal from the local unit. Block 2810 illustrates transmitting a first signal from the local unit in accordance with a preset program of signal transmission. For example, a local unit can be set to send a signal every 30 minutes, and therefore to transmit the first signal 30 minutes after a preset program of signal transmission is initiated. For example, a local unit can be set to transmit the first signal directly after a preset program of signal transmission is initiated.

Figure 29:
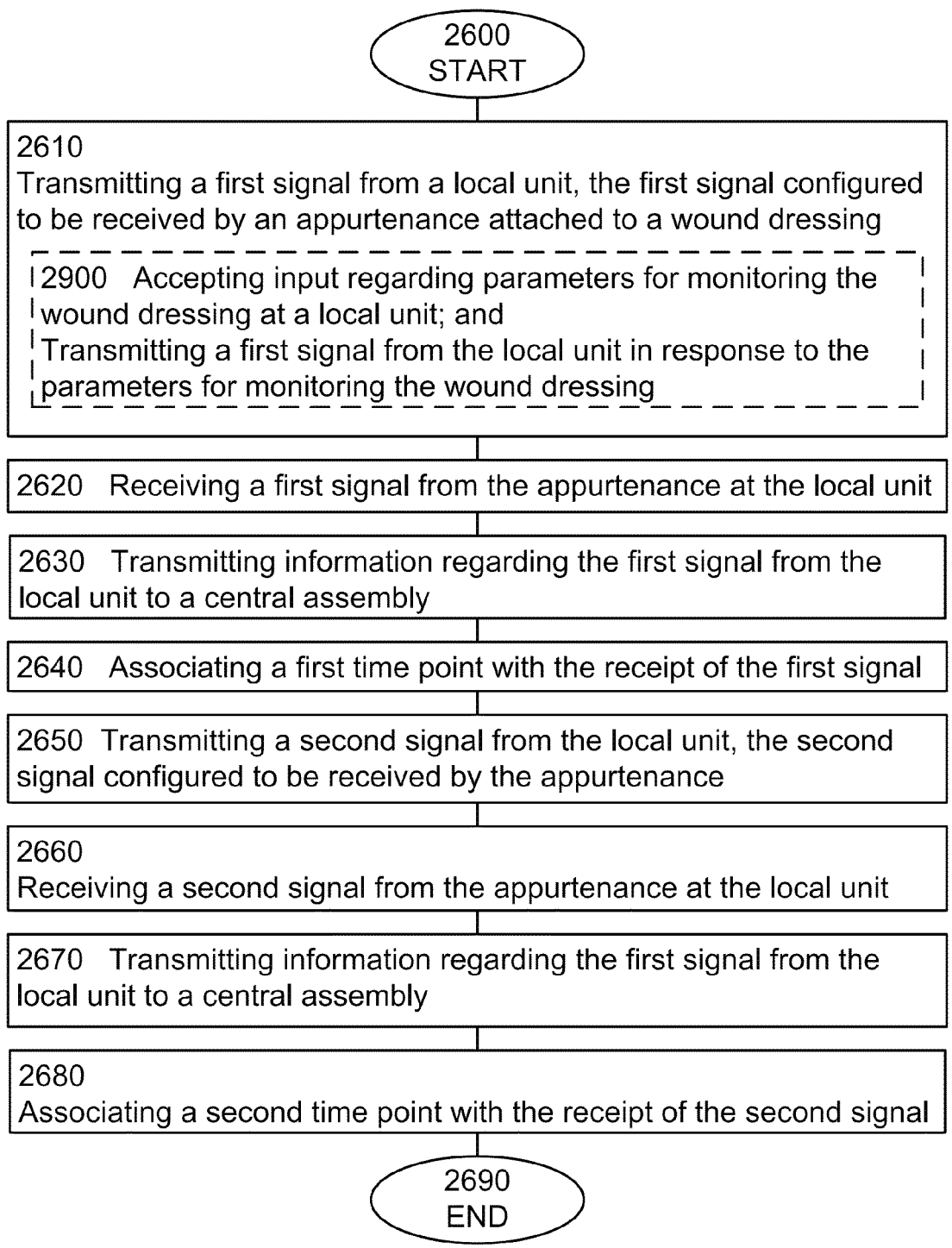
FIG. 29 is a flowchart illustrating aspects of a method such as shown in FIG. 26.

FIG. 29 shows aspects of the flowchart shown in FIG. 26. FIG. 29 depicts that, in some embodiments, block 2610 can include block 2900. Block 2610 illustrates transmitting a first signal from a local unit, the first signal configured to be received by an appurtenance attached to a wound dressing. Block 2900 shows: accepting input regarding parameters for monitoring the wound dressing at a local unit; and transmitting a first signal from the local unit in response to the parameters for monitoring the wound dressing. For example, a user may input parameters such as "monitor every 15 minutes" in to a local unit and the local unit may transmit a first signal 15 minutes after receiving this input. For example, a user may input parameters such as "use protocol A" in to a local unit and the local unit may transmit a first signal immediately after receiving this input in accord with the protocol.

Figure 30:
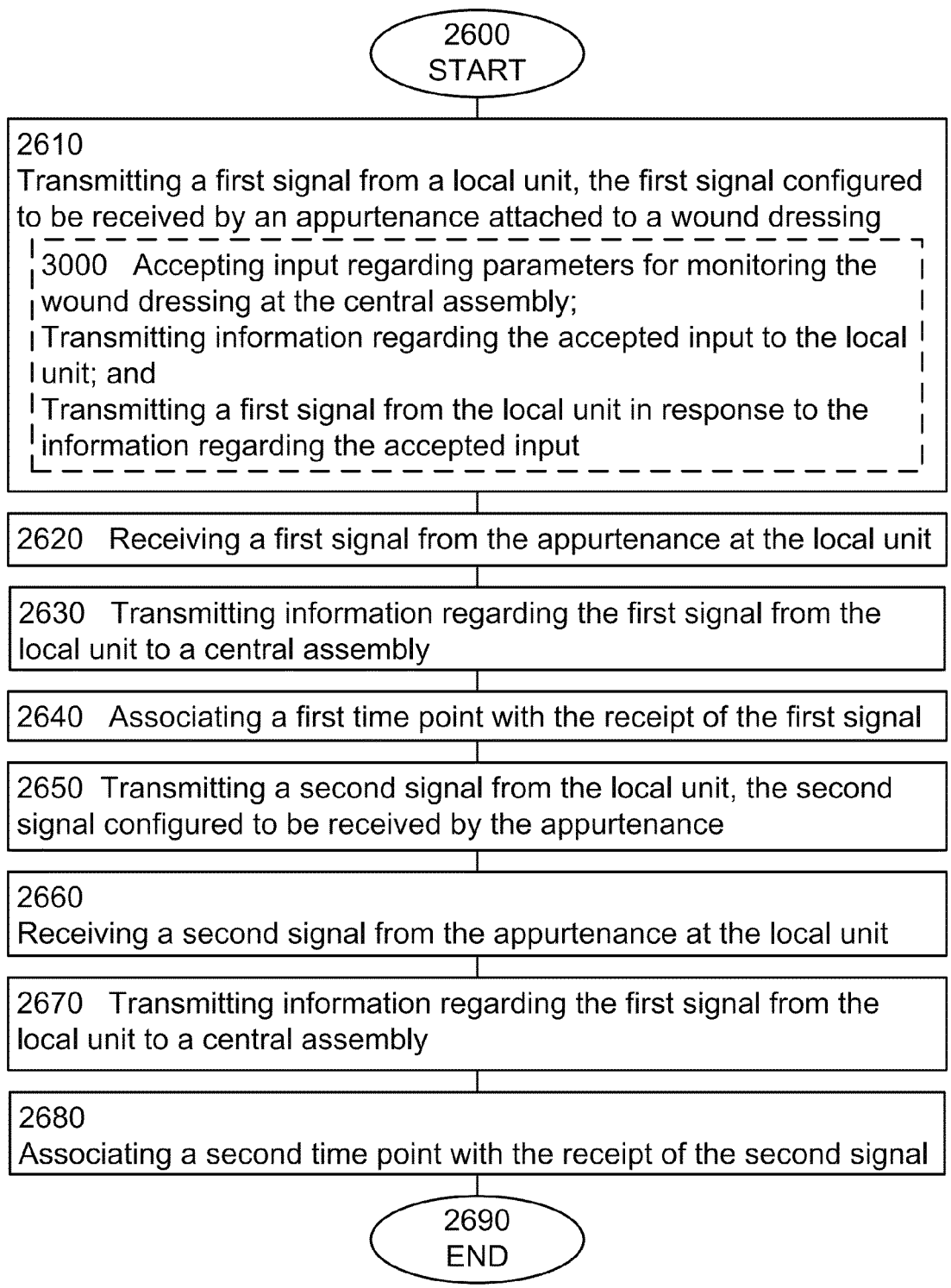
FIG. 30 is a flowchart showing aspects of a method such as illustrated in FIG. 26.

FIG. 30 shows aspects of the flowchart shown in FIG. 26. FIG. 30 depicts that, in some embodiments, block 2610 can include block 3000. Block 2610 illustrates transmitting a first signal from a local unit, the first signal configured to be received by an appurtenance attached to a wound dressing. Block 3000 illustrates: accepting input regarding parameters for monitoring the wound dressing at the central assembly; transmitting information regarding the accepted input to the local unit; and transmitting a first signal from the local unit in response to the information regarding the accepted input. For example, a user may input into the central assembly information regarding a wound type, and the central assembly may determine specific parameters for monitoring that type of wound dressing from a look up table, and transmit information regarding those specific parameters to a local unit. For example, a central assembly may accept input that a patient has a chronic ulcer, and associate that with monitoring the wound dressing every hour for 3 days based on a predetermined standard of care in a look-up table. The central assembly may then transmit instructions to a local unit including that the local unit should transmit a first signal after 1 hour. For example, a central assembly may accept input that a particular appurtenance-wound dressing unit should be signaled every 15 minutes, and the central assembly may then transmit instructions to a local unit including that the local unit should transmit a first signal 15 minutes after the appurtenance-wound dressing unit is placed in use.

Figure 31:
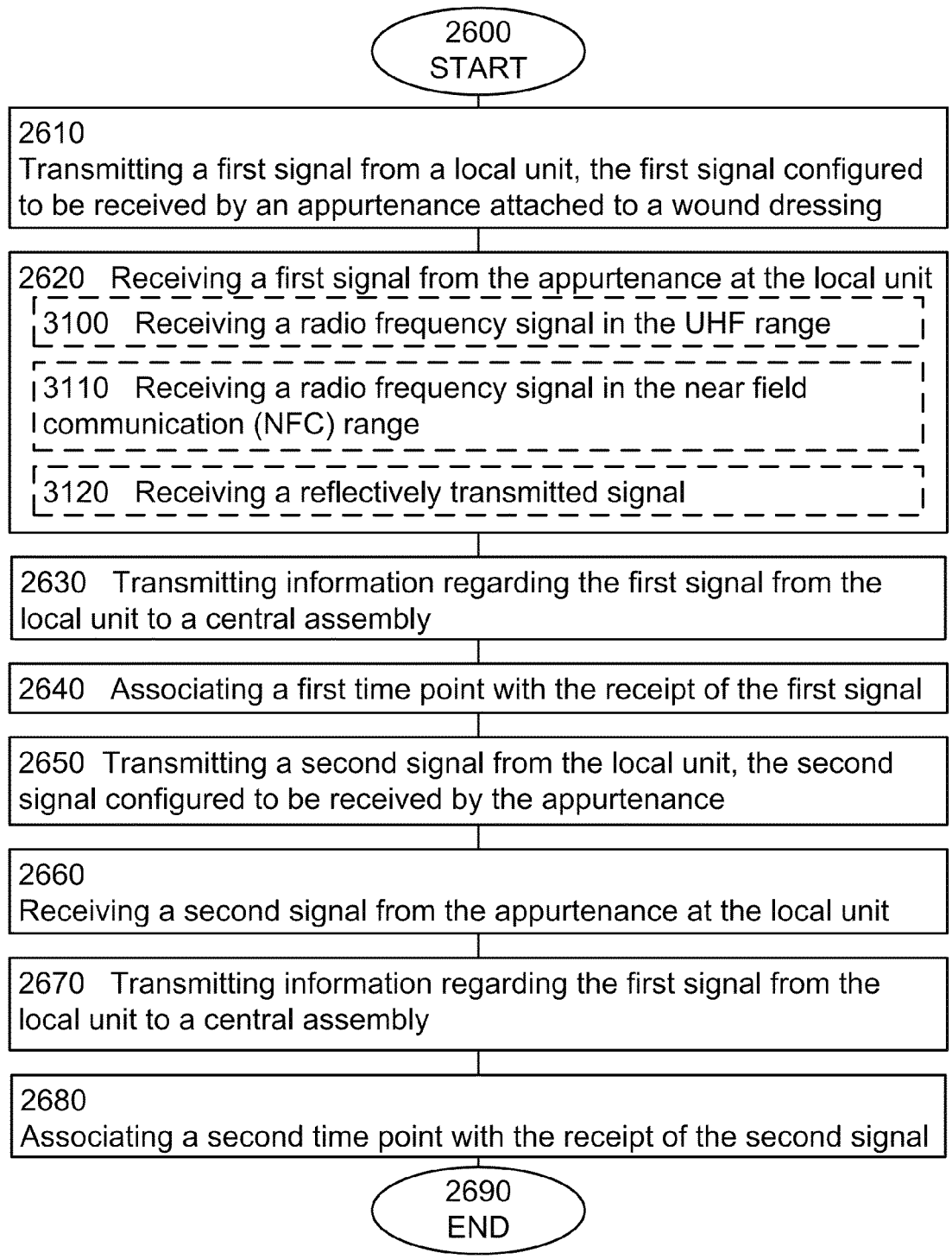
FIG. 31 is a flowchart illustrating aspects of a method such as shown in FIG. 26.

FIG. 31 illustrates aspects of the flowchart shown in FIG. 26. FIG. 31 shows that, in some embodiments, block 2620 can include at least one of optional blocks 3100, 3110 and 3120. Block 2620 shows receiving a first signal from the appurtenance at the local unit. Block 3100 illustrates receiving a radio frequency signal in the UHF range. For example, the local unit may receive a reflectively transmitted signal from an RFID unit integral to the appurtenance in the UHF range. Block 3110 illustrates receiving a radio frequency signal in the near field communication (NFC) range. For example, the appurtenance and the local unit can include integral NFC units. Block 3120 shows receiving a reflectively transmitted signal. For example, the local unit may receive a reflectively transmitted signal from an RFID unit integral to the appurtenance.

Figure 32:
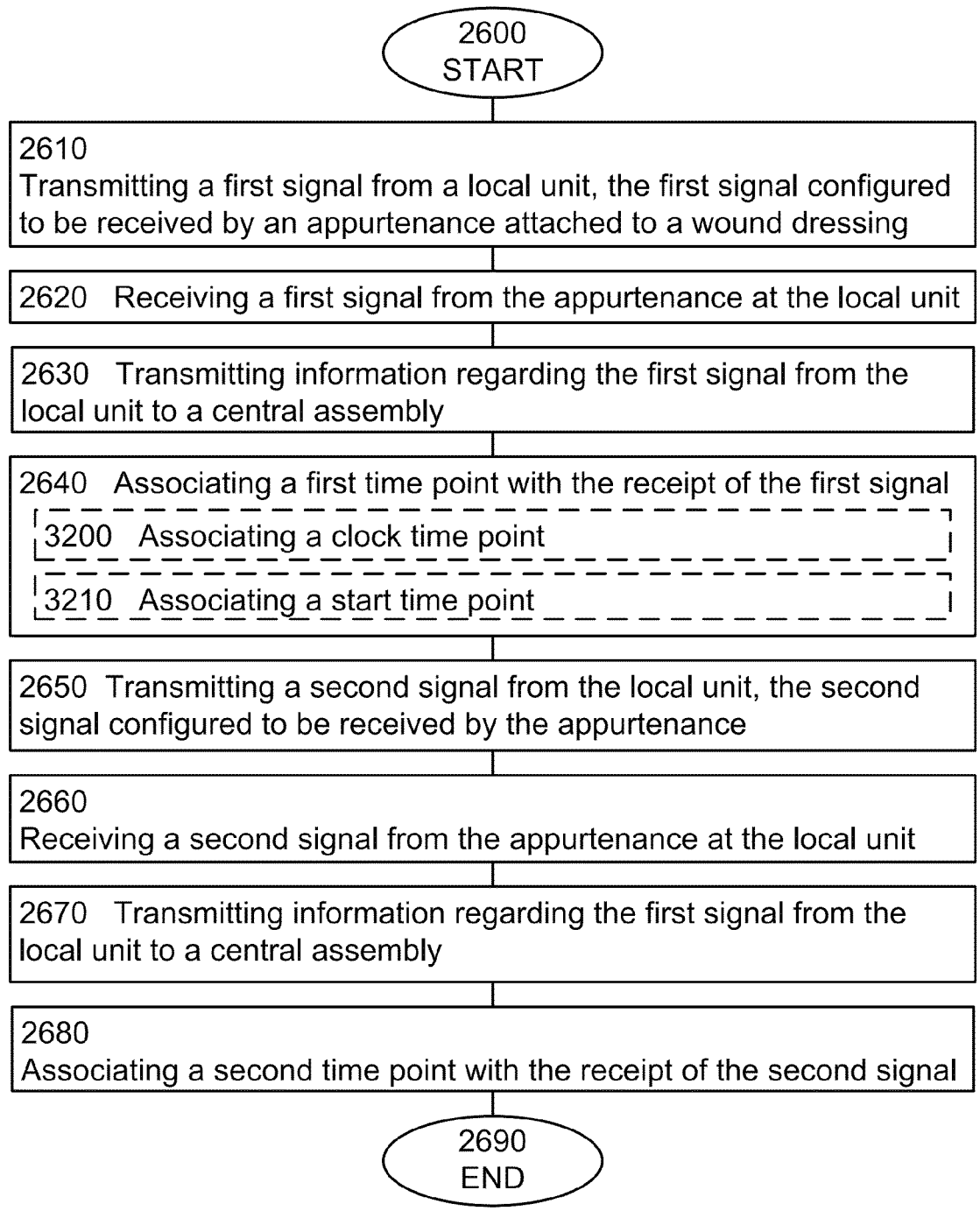
FIG. 32 is a flowchart displaying aspects of a method such as illustrated in FIG. 26.

FIG. 32 depicts aspects of the flowchart shown in FIG. 26. FIG. 32 shows that, in some embodiments, block 2640 can include at least one of optional blocks 3200 and 3210. Block 2640 shows associating a first time point with the receipt of the first signal. Block 3200 illustrates associating a clock time point. For example, associating "15:40 on May 22, 2010" with the receipt of the first signal. Block 3210 shows associating a start time point. For example, associating a time point "zero" or initiation of elapsed time detection.

Figure 33:
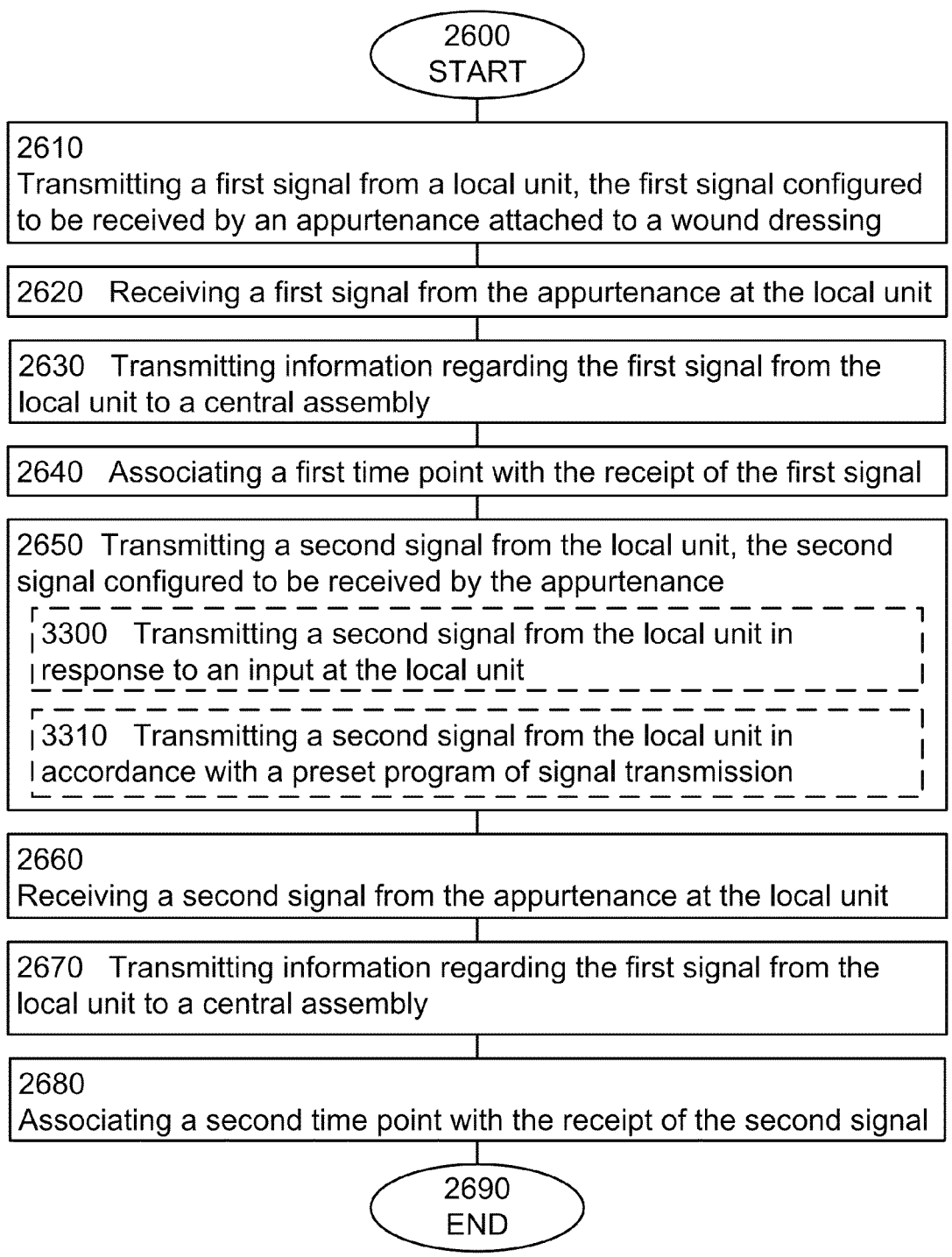
FIG. 33 is a flowchart illustrating aspects of a method such as shown in FIG. 26.

FIG. 33 shows aspects of the flowchart shown in FIG. 26. FIG. 33 shows that, in some embodiments, block 2650 can include at least one of optional blocks 3300 and 3310. Block 2650 depicts transmitting a second signal from the local unit, the second signal configured to be received by the appurtenance. Block 3300 shows transmitting a second signal from the local unit in response to an input at the local unit. For example, a user may press a button on the local unit to initiate transmission of the second signal. For example, a user may have preset a program of monitoring the appurtenance attached to the wound dressing, and therefore that there should be a second signal transmitted at a predefined time period after the first signal transmission. Block 3310 shows transmitting a second signal from the local unit in accordance with a preset program of signal transmission. For example, a local unit can be preset to transmit signals every 20 minutes while it is in operation.

Figure 34:
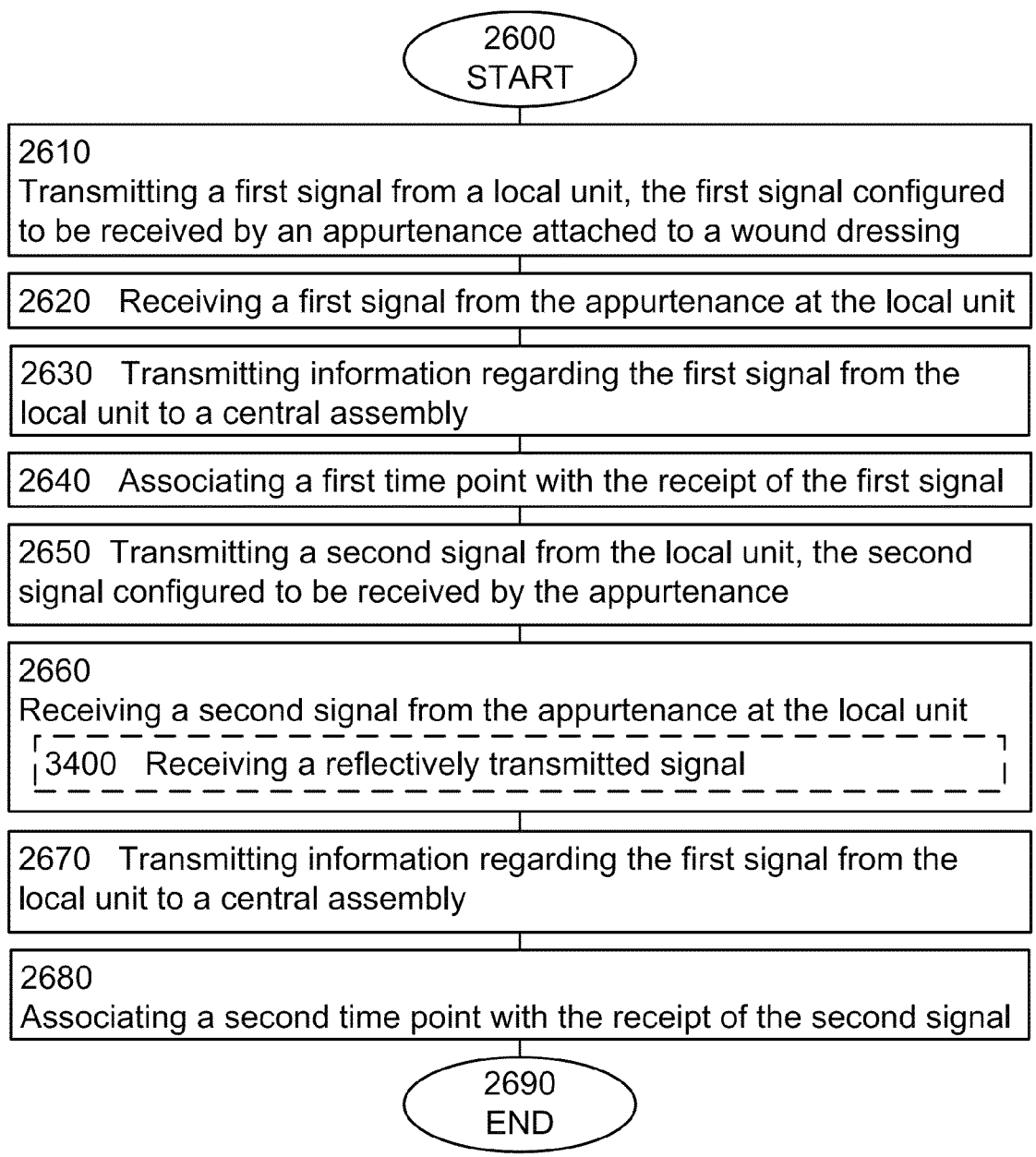
FIG. 34 is a flowchart showing aspects of a method such as displayed in FIG. 26.

FIG. 34 depicts aspects of the flowchart shown in FIG. 26. FIG. 34 shows that, in some embodiments, block 2660 can include optional block 3400. Block 2660 shows receiving a second signal from the appurtenance at the local unit. Block 3400 shows receiving a reflectively transmitted signal. For example, a local unit may receive a reflectively transmitted signal from an RFID unit integral to an appurtenance.

Figure 35:
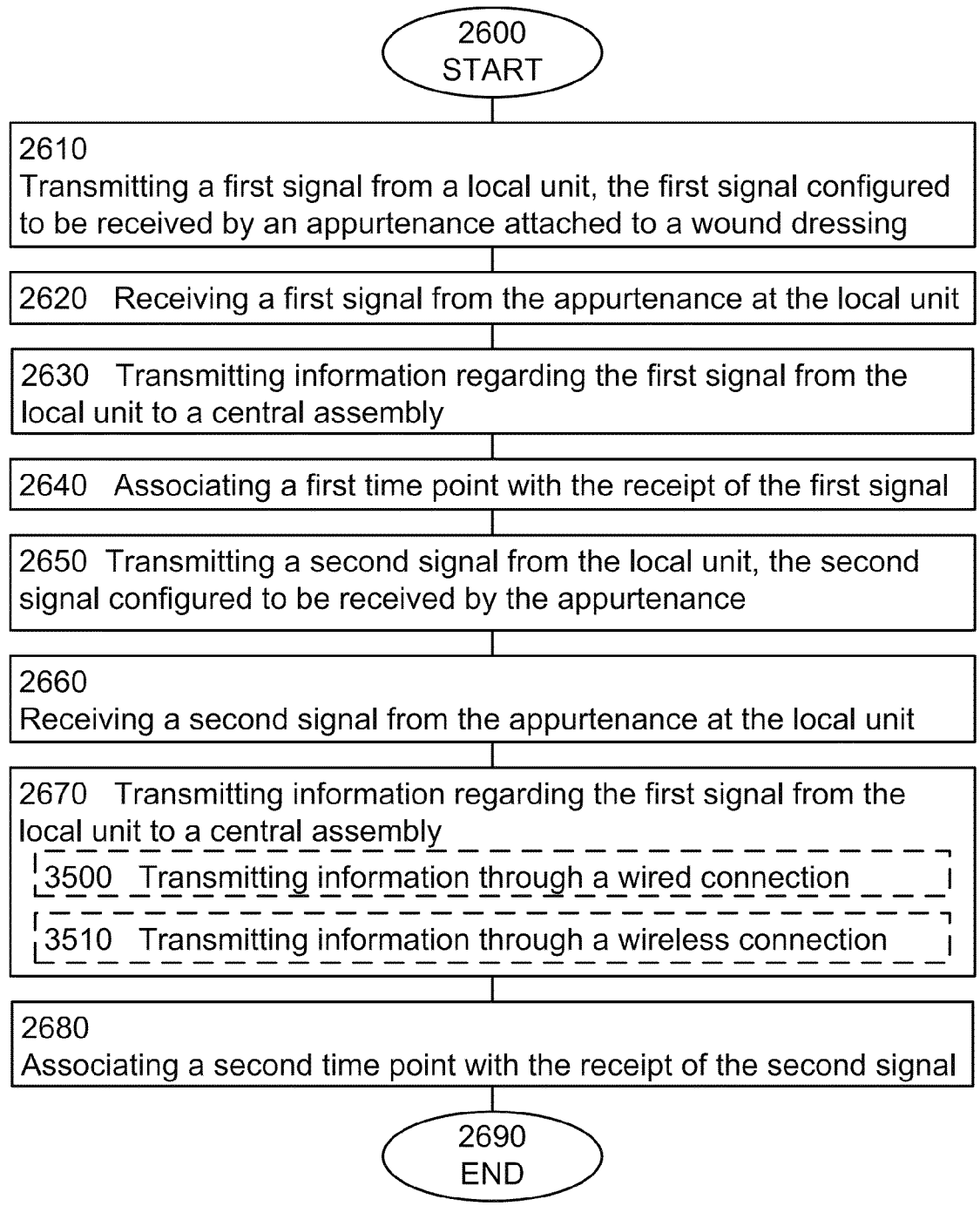
FIG. 35 is a flowchart illustrating aspects of a method such as shown in FIG. 26.

FIG. 35 shows aspects of the flowchart shown in FIG. 26. FIG. 35 shows that, in some embodiments, block 2670 can include one or more of optional blocks 3500 and 3510. Block 2670 depicts transmitting information regarding the first signal from the local unit to a central assembly. Block 3500 shows transmitting information through a wired connection. For example, the local unit can be able to send signals to the central assembly through a wired connection. Block 3510 illustrates transmitting information through a wireless connection. For example, the local unit may transmit information to the central assembly with wireless signals.

Figure 36:
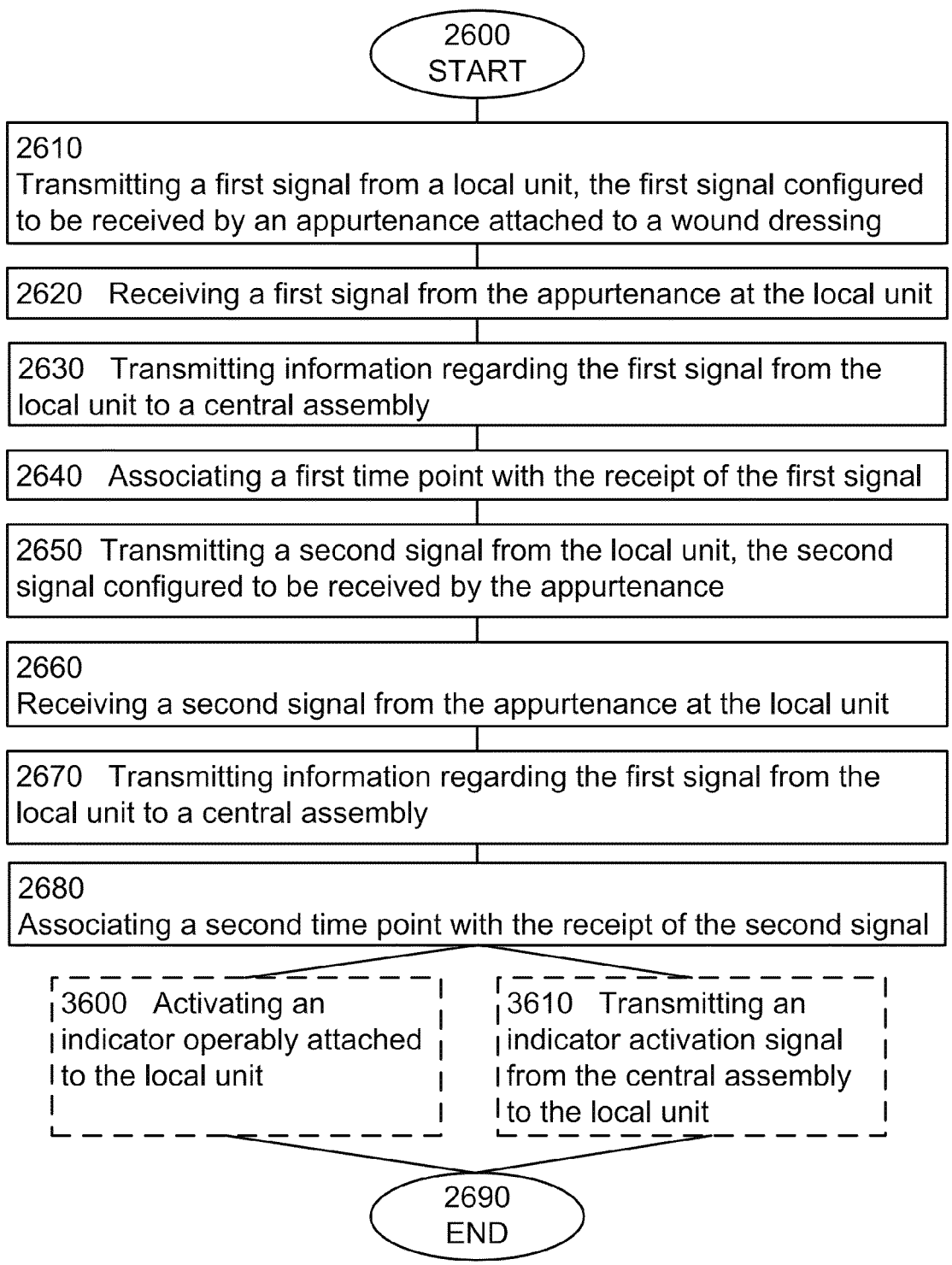
FIG. 36 is a flowchart showing aspects of a method such as illustrated in FIG. 26.

FIG. 36 illustrates aspects of the flowchart shown in FIG. 26. FIG. 36 shows that, in some embodiments, the flowchart can include one or more of optional blocks 3600 and 3610. Block 3600 shows activating an indicator operably attached to the local unit. For example, a LED, auditory signal generator, or vibration unit operably attached to the local unit can be activated. For example, the activation can be initiated by the processor in the local unit, in response to information conveyed in a signal from the appurtenance, such as activate the LED when no signal is detected for 10 minutes. For example, the activation can be initiated by the processor in the local unit, in response to a preset program, such as sound the alarm after 48 hours. Block 3610 shows transmitting an indicator activation signal from the central assembly to the local unit. For example, a central assembly may transmit an indicator activation signal to the local unit after a preset period of time, such as 36 hours, indicating that a caregiver should manually inspect or change the wound dressing.

Figure 37:
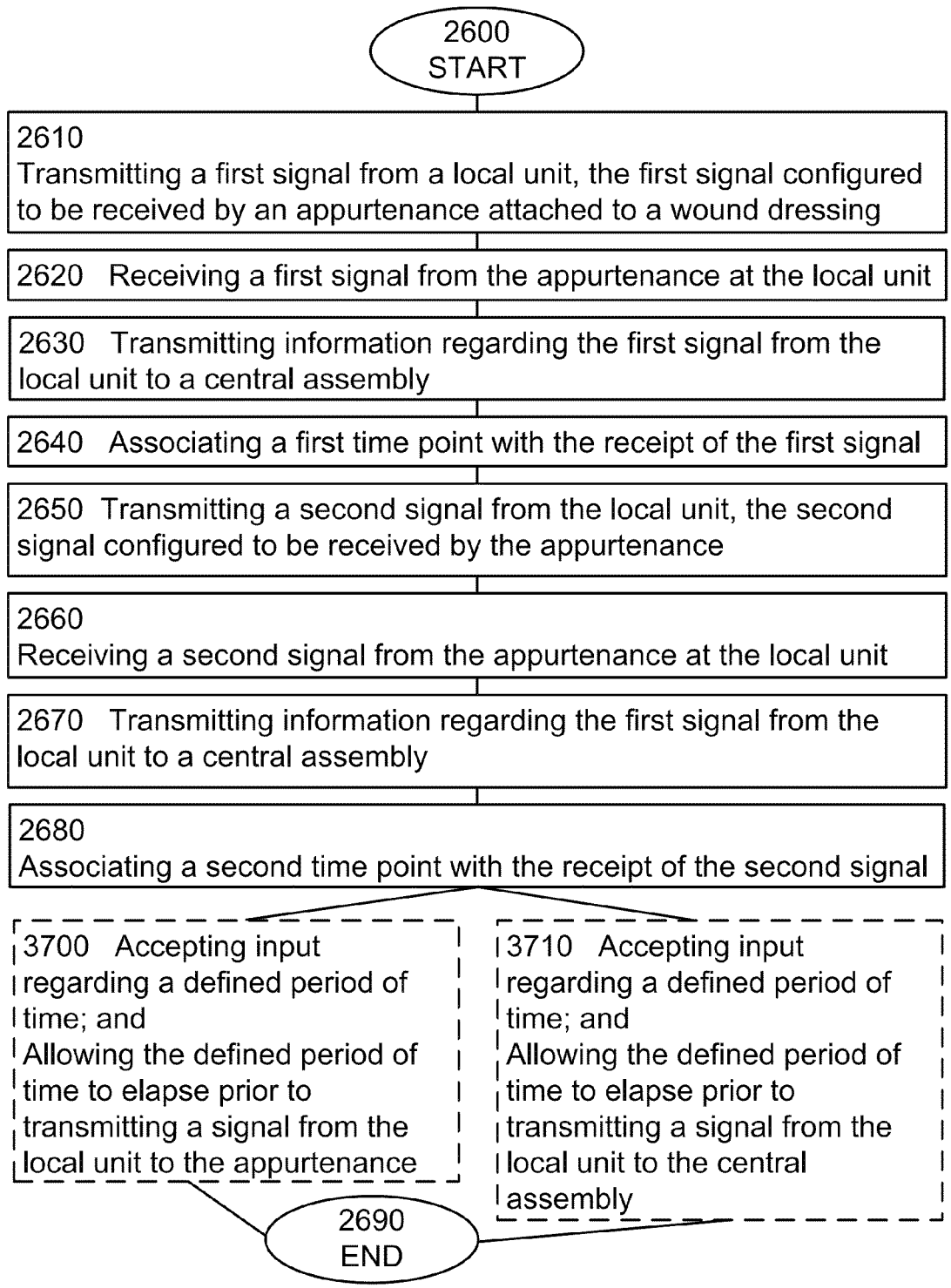
FIG. 37 is a flowchart illustrating aspects of a method such as shown in FIG. 26.

FIG. 37 shows aspects of the flowchart shown in FIG. 26. FIG. 37 shows that, in some embodiments, the flowchart can include one or more of optional blocks 3700 and 3710. Block 3700 illustrates accepting input regarding a defined period of time; and allowing the defined period of time to elapse prior to transmitting a signal from the local unit to the appurtenance. For example, a local unit may accept input on a touch-screen regarding a 15 minute interval between signals to the appurtenance, and the local unit may allow 15 minutes to elapse before the next signal to the appurtenance. Block 3710 shows accepting input regarding a defined period of time; allowing the defined period of time to elapse prior to transmitting a signal from the local unit to the central assembly. For example, a user may input information into a local unit through a keyboard indicating that the status of the appurtenance be reported to the central assembly every hour, and the local unit may allow an hour to pass before sending a signal to the central assembly including information regarding the status of the appurtenance.

Figure 38:
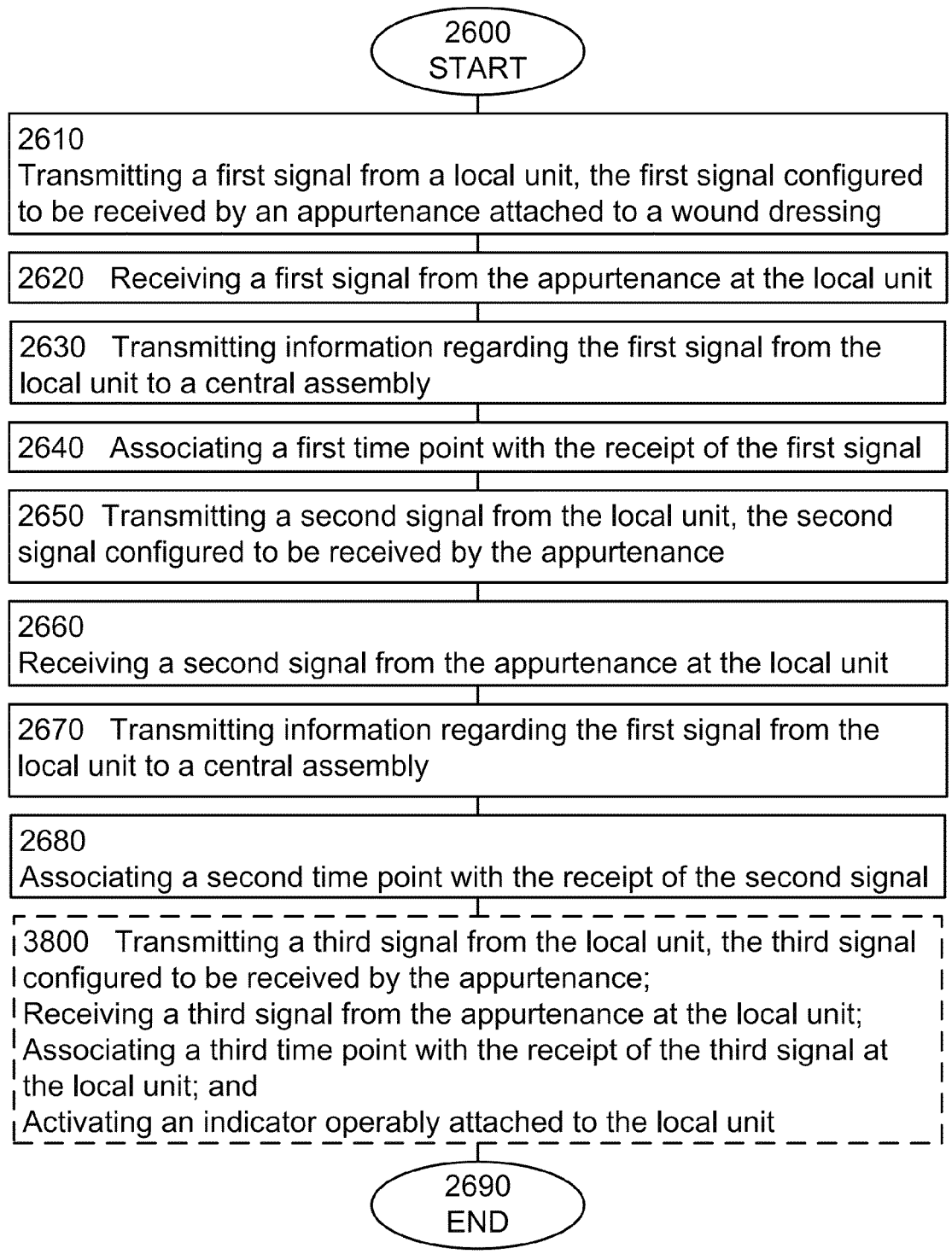

FIG. 38 shows aspects of the flowchart shown in FIG. 26. FIG. 38 shows that, in some embodiments, the flowchart can include optional block 3800. Block 3800 shows transmitting a third signal from the local unit, the third signal configured to be received by the appurtenance; receiving a third signal from the appurtenance at the local unit; associating a third time point with the receipt of the third signal at the local unit; and activating an indicator operably attached to the local unit. For example, the method steps illustrated in the flowchart of FIG. 26 and subsequent figures can be repeated a plurality of times to monitor an appurtenance affixed to a wound dressing.

FIG. 39 depicts a flowchart illustrating aspects of a method of monitoring an appurtenance attached to a wound dressing. The method illustrated in the flowchart of FIG. 39 includes a plurality of steps, as shown in the flowchart. The method illustrated in the flowchart of FIG. 39 can be carried out, for example, by a central assembly, such as a central hospital or clinic computer system. Block 3910 shows receiving a first transmission from a local unit, the first transmission including first information regarding an appurtenance attached to a wound dressing. For example, a first transmission from a local unit can be received by a central assembly, the first transmission including information such as regarding when an appurtenance was applied to the wound dressing, the patient to whom the wound dressing was applied, the status of the patient, and any specific monitoring instructions from the wound caregiver. Block 3915 illustrates associating a first time point with the receipt of the first transmission. For example, a clock time point, such as 19:25, can be associated with the receipt of the first transmission from the local unit by the central assembly. Block 3920 shows associating wound dressing parameters with the received first information regarding the appurtenance. For example, a first transmission can include a code identifying a wound type as "123A," and the central assembly may use a look-up table to associate that code with a wound dressing that should be monitored every hour and changed every 48 hours. Block 3925 illustrates determining, based on the associated wound dressing parameters and the received first information, a first status of the appurtenance. For example, if the received first information indicates that the appurtenance is functioning within normal parameters (i.e. sufficient signal strength, no warning indicators), a first status of the appurtenance can be "green" or "OK." For example, if the received first information indicates that the appurtenance is not functioning within normal parameters (i.e. insufficient signal strength, no signal or other indicators), a first status of the appurtenance can be "needs to be checked" or "red." Block 3930 depicts determining, based on the determined first status of the appurtenance, a first response. For example, if the determined first status is "green" or "OK" a first response can be to continue monitoring, or to send a "OK" signal to the local unit or the nursing station, or both. For example, if the determined first status is "needs to be checked" or "red," a signal indicating that the wound dressing needs to be physically checked can be sent to the local unit or to the nursing station, or both. Block 3935 shows saving into memory as a record of the appurtenance the first time point, the received first information and the associated wound dressing parameters. For example, a central assembly may save into non-volatile memory the received information regarding the appurtenance. For example, a central assembly may save into a patient's medical record information about an appurtenance attached to a specific wound dressing, such as the first time point, the received first information and the associated wound dressing parameters. Block 3940 illustrates receiving a second transmission from the local unit, the second transmission including second information regarding the appurtenance attached to the wound dressing. For example, the second information can include a time point, signal strength information, and information from one or more sensors of the appurtenance. Block 3945 illustrates associating a second time point with the receipt of the second transmission. For example, a clock time point or an elapsed time point since the receipt of the first transmission. Block 3950 shows associating the record of the appurtenance with the received second information regarding the appurtenance. For example, an appurtenance-specific identification number can be used to associate the record with the received second information regarding the appurtenance. Block 3955 shows determining, based on the associated record and the received second information, a second status of the appurtenance. For example, a predetermined set of criteria can be applied to determine a second status of the appurtenance, such as a loss of signal strength of a predetermined amount, or an elapsed period of time. For example, a determined second status can include "green," or "no problem noted." For example, a determined second status can include "red," or "notify caregiver to inspect wound dressing." Block 3960 shows determining, based on the determined second status of the appurtenance, a second response. For example, if the determined second status includes "green," or "no problem noted," a second response can be to send a "status OK" signal to the local unit or to a nursing station, or both. For example, if the determined second status includes "red," or "notify caregiver to inspect wound dressing," a second response can be to transmit an "alert" message to the local unit or to a nursing station, or both. Block 3965 shows saving into memory with the record of the appurtenance the second time point and the received second information. In the interests of space on the Figure, a start and stop of the method are not illustrated in FIG. 39.

Figure 40:
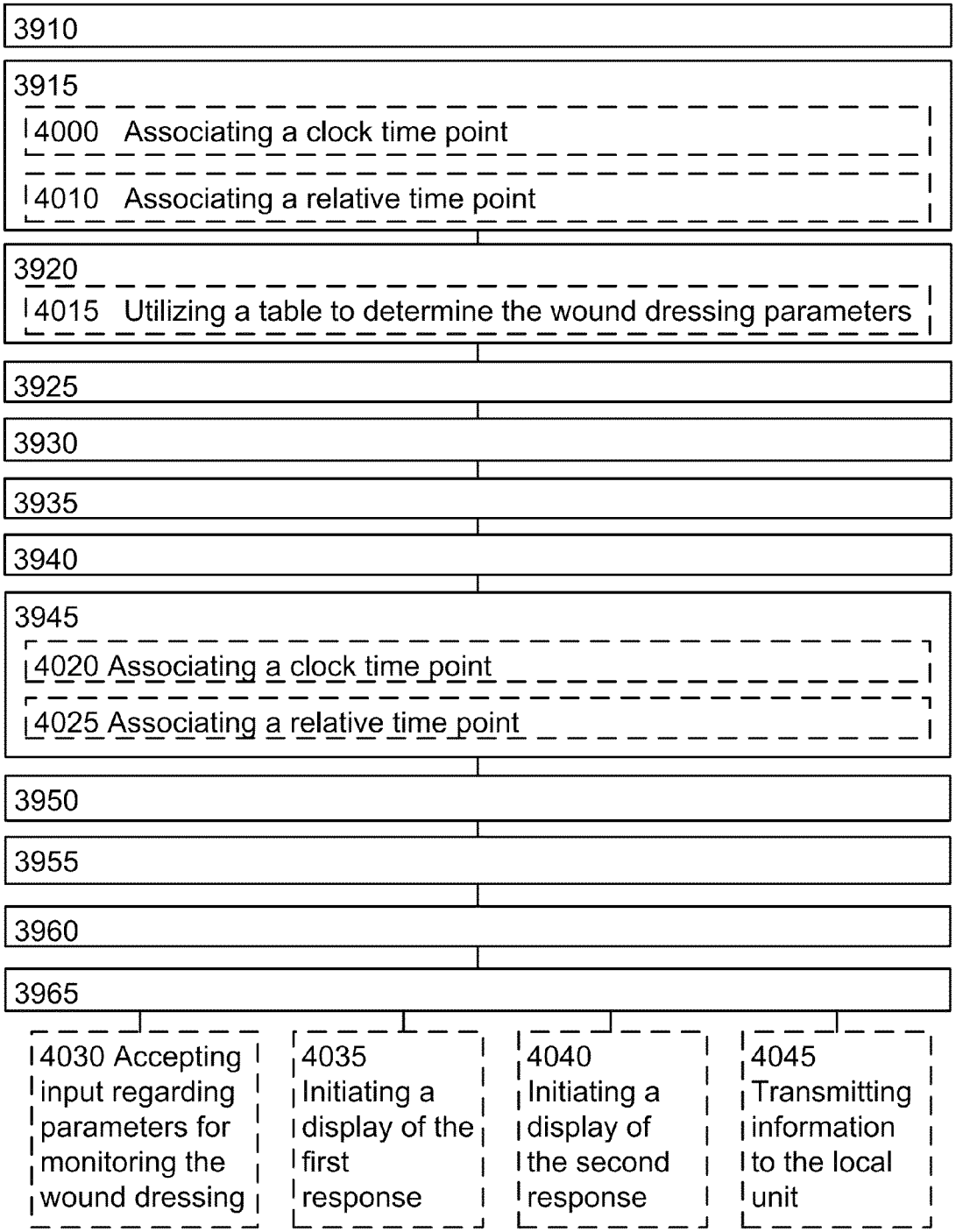
FIG. 40 is a flowchart illustrating aspects of a method such as shown in FIG. 39.

FIG. 40 shows aspects of the flowchart shown in FIG. 39. FIG. 40 illustrates that, in some embodiments, block 3915 can include one or more of optional blocks 4000 and 4010. FIG. 40 depicts that, in some embodiments, block 3920 can include optional block 4015. FIG. 40 illustrates that, in some embodiments, block 3945 can include one or more of optional blocks 4020 and 4025. FIG. 40 shows that, in some embodiments, the flowchart can include one or more of optional blocks 4030, 4035, 4040 or 4045. In the interests of space in FIG. 40, some of the text of FIG. 39 has been omitted but it should be considered that the blocks continue to represent the same aspects of the flowchart. Block 3915 illustrates associating a first time point with the receipt of the first transmission. Block 3915 can include one or more of optional blocks 4000 and 4010. Block 4000 shows associating a clock time point. For example, a day and time can be associated with the receipt of the first transmission. Block 4010 illustrates associating a relative time point. For example, the elapsed time since the appurtenance was activated can be associated with the receipt of the first transmission. For example, the elapsed time since a surgery was performed (i.e. for an acute wound) can be associated with the receipt of the first transmission. Block 3920 shows associating wound dressing parameters with the received first information regarding the appurtenance. Block 3920 can include optional block 4015. Block 4015 depicts utilizing a table to determine the wound dressing parameters. For example, the processor of a central assembly may utilize a look-up table, or a set of parameters associated with specific wound codes. FIG. 40 illustrates that block 3945 can include one or more of optional blocks 4020 and 4025. Block 3945 illustrates associating a second time point with the receipt of the second transmission. Block 4020 shows associating a clock time point. Block 4025 depicts associating a relative time point. FIG. 40 illustrates that, in some embodiments, the flowchart can include one or more of optional blocks 4030, 4035, 4040 or 4045. Block 4030 illustrates accepting input regarding parameters for monitoring the wound dressing. For example, input identifying the type of wound dressing, and therefore its expected maximum length of use, can be accepted. For example, a specific parameter can be accepted, such as "check every 20 minutes." Block 4035 shows initiating a display of the first response. For example, a central assembly may transmit a signal to a nursing station to initiate a display on a monitor regarding the suggested first response. For example, a central assembly may transmit a signal to a local unit to initiate a LED indicator light indicating the suggested first response (i.e. red light for "check" and green light for "OK"). Block 4040 illustrates initiating a display of the second response. For example, a central assembly may transmit a signal to a nursing station to initiate a display on a monitor regarding the suggested second response. For example, a central assembly may transmit a signal to a local unit to initiate a LED indicator light indicating the suggested second response (i.e. red light for "check" and green light for "OK"). Block 4045 shows transmitting information to the local unit. For example, information can be transmitted from the central assembly to the local unit.

Figure 41:
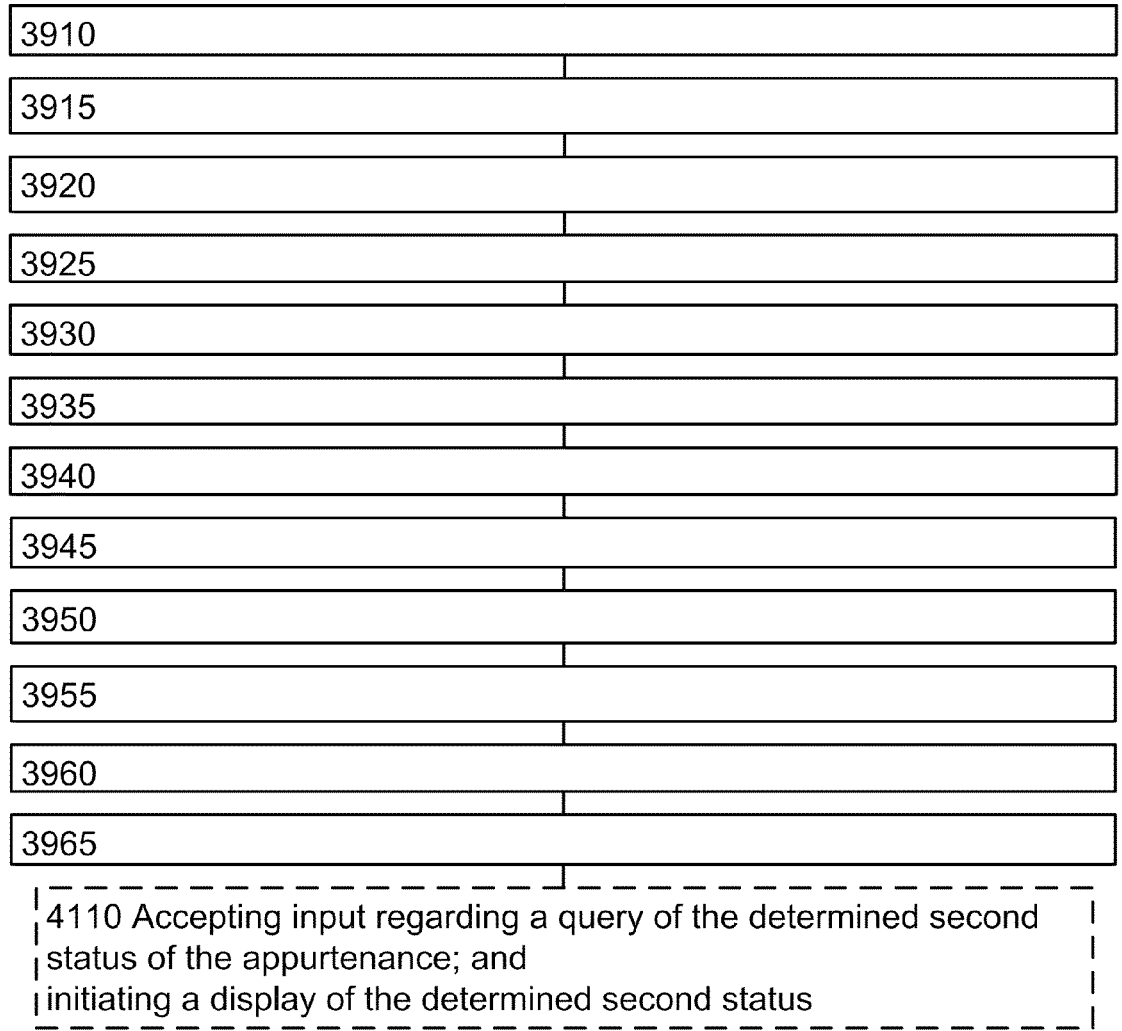
FIG. 41 is a flowchart showing aspects of a method such as displayed in FIG. 39.

FIG. 41 shows aspects of the flowchart shown in FIG. 39. FIG. 40 illustrates that, in some embodiments, the flowchart may contain optional block 4110. In the interests of space in FIG. 41, some of the text of FIG. 39 has been omitted but it should be considered that the blocks continue to represent the same aspects of the flowchart. Block 4110 shows accepting input regarding a query of the determined second status of the appurtenance; and initiating a display of the determined second status. For example, input regarding a query can be accepted at a user interface operably attached to the central assembly, and instructions can be sent to the user interface to initiate a display on a monitor of the determined second status. For example, input regarding a query can be accepted at a local unit and transmitted to the central assembly, which may transmit a response that initiates a display of the determined second status at the local unit.

FIG. 42 illustrates aspects of a local unit 540. The local unit 540 can be operated by a user 500. The local unit 540 can include circuitry. As shown in FIG. 42, the local unit 540 can include circuitry 4200 configured to monitor an appurtenance attached to a wound dressing. The circuitry 4200 includes circuitry 4210 for transmitting a first signal configured to be received by an appurtenance attached to a wound dressing. The circuitry 4200 includes circuitry 4220 for receiving a first signal from the appurtenance. The circuitry 4200 includes circuitry 4230 for associating a first time point with the receipt of the first signal. The circuitry 4200 includes circuitry 4240 for transmitting a second signal configured to be received by the appurtenance. The circuitry 4200 includes circuitry 4250 for receiving a second signal from the appurtenance. The circuitry 4200 includes circuitry 4260 for associating a second time point with the receipt of the second signal.

FIG. 43 illustrates aspects of a local unit 540. The local unit 540 can be operated by a user 500. The local unit 540 can include circuitry. As shown in FIG. 43, the local unit 540 can include circuitry 4300 configured to monitor an appurtenance attached to a wound dressing. The circuitry 4300 includes circuitry 4310 for transmitting a first signal from a local unit, the first signal configured to be received by an appurtenance attached to a wound dressing. The circuitry 4300 includes circuitry 4320 for receiving a first signal from the appurtenance at the local unit. The circuitry 4300 includes circuitry 4330 for transmitting information regarding the first signal from the local unit to a central assembly. The circuitry 4300 includes circuitry 4340 for associating a first time point with the receipt of the first signal. The circuitry 4300 includes circuitry 4350 for transmitting a second signal from the local unit, the second signal configured to be received by the appurtenance. The circuitry 4300 includes circuitry 4360 for receiving a second signal from the appurtenance at the local unit. The circuitry 4300 includes circuitry 4370 for transmitting information regarding the first signal from the local unit to a central assembly. The circuitry 4300 includes circuitry 4380 for associating a second time point with the receipt of the second signal.

FIG. 44 illustrates aspects of a central assembly. The central assembly can be operated by a user 700. The central assembly can include circuitry. As shown in FIG. 44, the central assembly can include circuitry 4400 configured for monitoring an appurtenance attached to a wound dressing. The circuitry 4400 includes circuitry 4410 for receiving a first transmission from a local unit, the first transmission including first information regarding an appurtenance attached to a wound dressing. The circuitry 4400 includes circuitry 4415 for associating a first time point with the receipt of the first transmission. The circuitry 4400 includes circuitry 4420 for associating wound dressing parameters with the received first information regarding the appurtenance. The circuitry 4400 includes circuitry 4425 for determining, based on the associated wound dressing parameters and the received first information, a first status of the appurtenance. The circuitry 4400 includes circuitry 4430 for determining, based on the determined first status of the appurtenance, a first response. The circuitry 4400 includes circuitry 4435 for saving into memory as a record of the appurtenance the first time point, the received first information and the associated wound dressing parameters. The circuitry 4400 includes circuitry 4440 for receiving a second transmission from the local unit, the second transmission including second information regarding the appurtenance attached to the wound dressing. The circuitry 4400 includes circuitry 4445 for associating a second time point with the receipt of the second transmission. The circuitry 4400 includes circuitry 4450 for associating the record of the appurtenance with the received second information regarding the appurtenance. The circuitry 4400 includes circuitry 4455 for determining, based on the associated record and the received second information, a second status of the appurtenance. The circuitry 4400 includes circuitry 4460 for determining, based on the determined second status of the appurtenance, a second response. The circuitry 4400 includes circuitry 44565 for saving into memory with the record of the appurtenance the second time point and the received second information.

FIG. 45 illustrates aspects of a computer system. The computer system can include a local unit, 540. The local unit 540 can be operated by a user 500. As shown in FIG. 45, a local unit 540 can include a computer system 4500 configured to monitor an appurtenance attached to a wound dressing. The computer system can include 4510, one or more instructions for transmitting a first signal configured to be received by an appurtenance attached to a wound dressing. The computer system can include 4520, one or more instructions for receiving a first signal from the appurtenance. The computer system can include 4530, one or more instructions for associating a first time point with the receipt of the first signal. The computer system can include 4540, one or more instructions for transmitting a second signal configured to be received by the appurtenance. The computer system can include 4550, one or more instructions for receiving a second signal from the appurtenance. The computer system can include 4560, one or more instructions for associating a second time point with the receipt of the second signal.

FIG. 46 illustrates aspects of a computer system. The computer system can include a local unit, 540. The local unit 540 can be operated by a user 500. As shown in FIG. 46, a local unit 540 can include a computer system 4600 configured to monitor an appurtenance attached to a wound dressing. The computer system can include 4610, one or more instructions for transmitting a first signal from a local unit, the first signal configured to be received by an appurtenance attached to a wound dressing. The computer system can include 4620, one or more instructions for receiving a first signal from the appurtenance at the local unit. The computer system can include 4630, one or more instructions for transmitting information regarding the first signal from the local unit to a central assembly. The computer system can include 4640, one or more instructions for associating a first time point with the receipt of the first signal. The computer system can include 4650, one or more instructions for transmitting a second signal from the local unit, the second signal configured to be received by the appurtenance. The computer system can include 4660, one or more instructions for receiving a second signal from the appurtenance at the local unit. The computer system can include 4670, one or more instructions for transmitting information regarding the first signal from the local unit to a central assembly. The computer system can include 4680, one or more instructions for associating a second time point with the receipt of the second signal.

FIG. 47 illustrates aspects of a computer system. The computer system can include a central assembly. The central assembly can be operated by a user 700. As shown in FIG. 47, a central assembly can include a computer system 4700 configured to monitor an appurtenance attached to a wound dressing. The computer system can include 4710, one or more instructions for receiving a first transmission from a local unit, the first transmission including first information regarding an appurtenance attached to a wound dressing. The computer system can include 4715, one or more instructions for associating a first time point with the receipt of the first transmission. The computer system can include 4720, one or more instructions for associating wound dressing parameters with the received first information regarding the appurtenance. The computer system can include 4725, one or more instructions for determining, based on the associated wound dressing parameters and the received first information, a first status of the appurtenance. The computer system can include 4730, one or more instructions for determining, based on the determined first status of the appurtenance, a first response. The computer system can include 4735, one or more instructions for saving into memory as a record of the appurtenance the first time point, the received first information and the associated wound dressing parameters. The computer system can include 4740, one or more instructions for receiving a second transmission from the local unit, the second transmission including second information regarding the appurtenance attached to the wound dressing. The computer system can include 4745, one or more instructions for associating a second time point with the receipt of the second transmission. The computer system can include 4750, one or more instructions for associating the record of the appurtenance with the received second information regarding the appurtenance. The computer system can include 4755, one or more instructions for determining, based on the associated record and the received second information, a second status of the appurtenance. The computer system can include 4760, one or more instructions for determining, based on the determined second status of the appurtenance, a second response. The computer system can include 4765, one or more instructions for saving into memory with the record of the appurtenance the second time point and the received second information.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations can include executing a special-purpose instruction sequence or invoking circuitry for enabling, triggering, coordinating, requesting, or otherwise causing one or more occurrences of virtually any functional operations described herein. In some variants, operational or other logical descriptions herein can be expressed as source code and compiled or otherwise invoked as an executable instruction sequence. In some contexts, for example, implementations can be provided, in whole or in part, by source code, such as C++, or other code sequences. In other implementations, source or other code implementation, using commercially available and/or techniques in the art, can be compiled/ /implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) can be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

At least a portion of the devices and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, changes and modifications can be made without departing from the subject matter described herein and its broader aspects and, therefore, the appended claims are to encompass within their scope all such changes and modifications as are within the true spirit and scope of the subject matter described herein. Terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the recited operations therein may generally be performed in any order. Also, although various operational flows are presented in a sequence(s), it should be understood that the various operations can be performed in other orders than those which are illustrated, or can be performed concurrently. Examples of such alternate orderings can include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

EXAMPLES

Example 1

An Appurtenance to a Wound Dressing Configured to Detect and Report Fluid in a Wound Dressing An appurtenance to a wound dressing is constructed from a flexible thin plastic substrate which is configured in a substantially planar shape. A passive RFID antenna is attached to a surface of the substrate with epoxy. Circuitry for the RFID is attached to the substrate with adhesive and connected to the antenna with conductive ink (e.g., polymer with flecks of silver) as needed to create an operational RFID. Also a port for a polyester tube with approximately 0.5 mm inside diameter is mounted in contact with the antenna with epoxy. The polyester tube projects away from the surface of the substrate for approximately 4 millimeters (mm). Encapsulating epoxy material is used to cover the RFID circuit, the conductive ink, conductive epoxy and exterior of the tube port. A space is maintained around the edge of the polyester tube adjacent to the antenna. The space is configured to allow fluid to flow from the tube into contact with the surface of the antenna. The space is approximately 1 mm high and of sufficient lateral dimensions to cover a region of the antenna (e.g. 2-3 mm across). Methods and circuitry to construct passive RFID tags are described (see e.g., U.S. Pat. No. 7,479,886 issued to Burr, titled "Antenna Capacitance for Energy Storage" and Chawla, "An Overview of Passive RFID," *IEEE Applications & Practice*, 11-17, (September 2007), which are each incorporated herein by reference).

The substrate of the appurtenance is attached to the outer surface of a wound dressing with adhesive. A styrene copolymer pressure-sensitive adhesive can be used. In addition, the distal end of the polyester tube is pressed into the layers of the wound dressing with finger-tip pressure (see FIG. 2B). The wound dressing is of sufficient thickness so as to maintain the end of the polyester tube within the layers of the wound dressing, allowing for both the length of the tube itself and the angle it projects from the substrate. For example, if the tube is 4 mm long, the wound dressing can be 6 mm thick, or greater. For example, if the tube is 4 mm long, the wound dressing can be 4 mm thick if the tube is placed at a sufficient angle to maintain the distal end of the tube within the wound dressing. The wound dressing with the appurtenance is placed immediately over the wound and the RFID identity number, patient information, the time and date are entered into a central computer system after interrogating the RFID tag with a RFID reader in a local unit and accessing the patient's electronic medical record. If the patient is wearing an RFID identification device (such as a wristband with an embedded RFID), the patient information can be input into the system by scanning the identification device in association with scanning the appurtenance.

A RFID reader in a local unit proximal to the patient (e.g., on the edge patient's hospital bed or on a bedside table) is used to periodically interrogate the appurtenance on the wound dressing by transmitting a signal in the UHF range (e.g. 902-928 MHz). The local unit can be set to interrogate the appurtenance on a regular schedule, for example every 5 minutes, every 10 minutes, or every half hour. The local unit may also be set to interrogate the appurtenance on command by a user, such as a nurse, orderly, or other medical caregiver.

The appurtenance receives the incident UHF waves and harvests energy to activate the RFID circuitry and transmit a backscatter signal to the RFID reader. The signal encodes the identity of the RFID device and the signal reflects the status of the antenna. If moisture present in the wound dressing reaches levels sufficient for fluid to flow from the wound dressing into the tube of the appurtenance and into contact with the RFID antenna of the appurtenance, contact with the fluid on the antenna will modulate function of the antenna. This modulation, which can be a complete loss of function or a reduction or alteration of the "dry" signal, notifies the system that the wound dressing should be checked by a medical caregiver. Excess moisture to the level of fluid flow into the appurtenance can be caused, by example, from the patient bleeding at the wound site, or excess wound exudates.

The RFID reader in the local unit receives signals from the appurtenance RFID device and transmits signals to a central computer that convey: the patient identity, time, date, and moisture status of the wound dressing. The central computer may notify caregivers, for example through a message sent to the nursing station, if the antenna signal from the appurtenance is modulated in a subsequent query, or series of queries. The local unit may also indicate to a healthcare worker the need to change a wound dressing based on the elapsed time since the wound dressing was applied (i.e. when the appurtenance was first "read" into the system).

Example 2

An Appurtenance to a Wound Dressing Configured to Detect and Report Fluid Directly from the Wound or Wound Bed An appurtenance to a wound dressing is constructed substantially similarly as described in Example 1, above. However, the wound dressing is of sufficient thickness so as to allow the end of the polyester tube to protrude through the layers of the wound dressing, allowing for both the length of the tube itself and the angle it projects from the substrate. For example, if the tube is 6 mm long, the wound dressing can be 4 mm thick, depending on the angle of the tube projection through the wound dressing. For example, if the tube is 4 mm long, the wound dressing can be 4 mm thick if the tube is placed at a sufficient angle to allow the distal end of the tube to be at the surface of, or protrude from, the wound dressing. The polyester tube should not protrude from the wound dressing in a manner to create a new injury or puncture in the wound or body part. In contrast, if a wound contains a region that is a hollow or depression relative to the adjacent body part surface, the polyester tube can be positioned with its terminal region within this hollow or depression. The appurtenance and affixed wound dressing may then be monitored substantially similarly as described in Example 1, above.

Example 3

An Appurtenance Inserted into a Wound Dressing to Monitor Wound Healing and Infection is Constructed Using a Passive RFID Tag and Sensors Inside an Enclosure of a Height and Width to Fit Substantially within the Wound Dressing An appurtenance for a wound dressing configured to monitor wound healing and infection is constructed with an enclosure structure surrounding the appurtenance components. The appurtenance to a wound dressing includes a programmable RFID sensor device. The device is constructed with a RFID device on a printed circuit board with external sensors. For example, the device may contain a dipole antenna of 22-gauge copper magnet wire, a rectifier to convert incoming UHF energy into DC voltage, a capacitor to store the voltage, and a programmable microcontroller to perform sensing and computation (see e.g., Sample et al., "Design of an RFID-Based Battery-Free Programmable Sensing Platform," *IEEE Trans. Instr. Meas.* 57: 2608-2615, 2008 which is incorporated herein by reference). The RFID device may also have multiple sensors connected to the microcontroller to detect wound healing and infection. Each sensor projects into the lower portion of the appurtenance relative to the insertion point into the wound dressing. The sensors are located substantially within the enclosure and adjacent to an opening in the enclosure. For example, a moisture sensor comprised of two electrodes located adjacent to an opening in the enclosure can be used to monitor the amount of fluids (e.g., exudate and blood) inside the wound dressing emanating from the wound. The electrode-based moisture sensor correlates moisture levels and impedance in the sensor (see e.g., McColl et al., "Monitoring Moisture without Disturbing the Wound Dressing," *Wounds UK* 5: 94-99, 2009 which is incorporated herein by reference). Wound moisture levels are correlated with healing, and a rapid increase in moisture level may indicate a microbial infection is present (see e.g., U.S. Pat. No. 6,963,772 to Bloom et al. titled "User-Retainable Temperature and Impedance Monitoring Methods and Devices," which is incorporated herein by reference). The RFID device includes a second sensor configured to measure the temperature of the wound dressing, and by extension the adjacent wound region. For example, an external analog temperature sensor can be connected to the microcontroller of the device and extend into the wound dressing to monitor the temperature of the wound dressing and adjacent wound region. RFID devices with external temperature sensors accurate to approximately 2° C. are described (see e.g., Sample et al., "Design of an RFID-Based Battery-Free Programmable Sensing Platform," *IEEE Trans. Instr. Meas.* 57: 2608-2615, 2008 which is incorporated herein by reference). Methods to use temperature sensors to detect the presence of microbial infections are known. For example, a thermistor-based sensor is used to monitor the temperature of a wound and indicate the presence of an infection or normal wound healing (see e.g., U.S. Pat. No. 6,963,772 to Bloom et al. titled "User-Retainable Temperature and Impedance Monitoring Methods and Devices," which is incorporated herein by reference).

The appurtenance to a wound dressing is constructed in a "thumb tack" or "rivet" shaped design. The device enclosure is approximately 1-2 cm in diameter at the top and includes a region approximately 5 mm long that extends into the wound dressing. The enclosure contains the thermistor-based temperature sensor which is exposed to the wound surface and the moisture sensor, both positioned adjacent to an opening in the enclosure. In addition, the appurtenance is constructed with a pressure-sensitive adhesive on the underside of the flange at the top and barbs on the projection to hold the attachment firmly in place after insertion in the bandage.

Methods and materials to construct RFID tags and housings are described (see e.g., U.S. Pat. No. 6,693,513 to Tuttle, titled "Wireless Identification device, RFID Device with Push-On/Push Off Switch, and Method of Manufacturing Wireless Identification Device" and Sample et al., "Design of an RFID-Based Battery-Free Programmable Sensing Platform," *IEEE Trans. Instr. Meas.* 57: 2608-2615, 2008 which are each incorporated herein by reference).

The wound dressing appurtenance is used to monitor healing and infection of an individual's wound and to signal healthcare workers when the wound and the wound dressing need attention. The appurtenance is inserted manually in the wound dressing, and the combination unit is placed immediately over the wound to position the moisture and temperature sensors in the wound dressing proximal to the wound. The attachment receives UHF waves (e.g., approximately at 902-928 MHz) from a RFID reader in a local unit that is installed near the patient (e.g., within 10-15 meters for optimal signal from UHF waves), for example on the bed or on the wall of the hospital room. The RFID device receives UHF waves transmitted from the reader via the antenna, power harvesting circuitry, rectifying circuitry and a capacitor to empower the RFID device with direct (DC) current at approximately 1.8 volts. The power is used to drive the microcontroller which energizes the sensors, collects and computes data from the sensors and transmits a unique identification code and the collected sensor data to the RFID reader; the time and date of the signal transmission are also encoded and sent to the RFID reader. The local unit including the RFID reader includes circuitry and processors to transmit the data to a central computer where it is entered into an electronic medical record for the patient and also sent to a healthcare worker assigned to the patient or the room.

Patient information, the bandage attachment ID code and the program for signal transmission from the local unit are entered in the central computer system and verified when the bandage appurtenance is installed by an initial signal transmission from the local unit. For example, a bandage appurtenance with a designated ID number is assigned to a patient by entering the ID number into the patient's electronic medical record when the appurtenance is inserted in the patient's wound dressing. The healthcare worker may use a mobile computer, e.g., laptop computer, to enter the ID number, the type of wound, type of bandage and the interrogation schedule for the local unit. The patient information and the ID code are verified by an initial interrogation by the RFID reader within the local unit.

Example 4

A Bandage Appurtenance System is Used to Monitor Wound Dressings on a Patient with Recurrent Bacterial Infections A patient with a history of methicillin resistant *staphylococcus aureus* (MRSA) infections is treated for a leg wound with a wound dressing and an appurtenance system that monitors the wound dressing for signs of infection and sends a signal when the wound dressing may need attention from a caregiver. The appurtenance to the wound dressing system reports data on the status of the wound dressing locally (within 10 meters of the patient) to a local unit containing a RFID reader. The local unit then processes the incoming signal and transmits information over an intranet or the internet to a central computer assembly. The appurtenance to the wound dressing system includes: an appurtenance to the wound dressing, which is a RFID sensor device; a local unit including a RFID reader which interrogates the attachment with UHF waves and receives and transmits data; and a central computer assembly which stores the data and transmits an alert for health caregivers in response to the information transmitted by the local unit.

An appurtenance to the wound dressing is constructed including a RFID device that contains a microcontroller and multiple sensors. Each of the sensors is substantially enclosed within a projection which extends into the wound dressing when the appurtenance is in use. The RFID device is constructed on a printed circuit board with external sensors. For example, the device may contain a dipole antenna of 22-gauge copper magnet wire, a rectifier to convert incoming UHF energy into DC, a capacitor to store the current, and a programmable microcontroller (e.g., a MSP430™ microcontroller available from Texas Instruments, Dallas, Tex.) to perform sensing and computation (see e.g., Sample et al., "Design of an RFID-Based Battery-Free Programmable Sensing Platform," *IEEE Trans. Instr. Meas.* 57: 2608-2615, 2008 which is incorporated herein by reference). The RFID device has ports on the microcontroller to connect multiple sensors to detect wound healing and infection. The appurtenance receives UHF waves (e.g., approximately at 902-928 MHz) from a local unit containing a RFID reader that is installed near the patient (e.g., within 10-15 meters for UHF waves). A long range RFID reader operating in the UHF band with an input/output interface for the internet or the local area network is available from GAO RFID Inc., Seattle, Wash. The RFID device in the appurtenance receives UHF waves transmitted from the reader integrated into the local unit via the appurtenance antenna, power harvesting circuitry, rectifying circuitry and capacitor. The incoming UHF signal empowers the RFID device of the appurtenance with DC current at approximately 1.8 volts. The power is used to drive the microcontroller which energizes the sensors, collects and processes data from the sensors and makes a transmission. The appurtenance transmits a unique identification code with the collected sensor data to the RFID reader in the local unit; the time and date of the signal transmission are also encoded and sent to the RFID reader.

Sensors which detect moisture, temperature and *Staphylococcus aureus* proteins are placed inside hollow tubes which project from the bottom of the bandage appurtenance into the wound dressing. Tubes approximately 2-4 mm long, and approximately 5 mm in diameter project from the appurtenance. These projections contain the sensors and determine their effective penetration into the wound dressing. For example, a moisture sensor comprised of two electrodes which extend into the wound dressing through a projection can be used to monitor the amount of fluids (e.g., exudate and blood) emanating from the wound. Electrode-based moisture sensors are used to correlate wound moisture levels and impedance in the sensor (see e.g., McColl et al., "Monitoring Moisture without Disturbing the Wound Dressing," *Wounds UK* 5: 94-99, 2009 which is incorporated herein by reference) while wound moisture levels are correlated with healing. For example, a rapid increase in moisture level may indicate a microbial infection is present (see e.g., U.S. Pat. No. 6,963,772 to Bloom et al. titled "User-Retainable Temperature and Impedance Monitoring Methods and Devices," which is incorporated herein by reference). A second projection tube contains a thermistor-based temperature sensor which projects to a region adjacent to the wound surface. For example, an external analog temperature sensor can be connected to the microcontroller of the device and extend into the wound dressing to monitor the temperature of the wound. The approximate distance between the wound surface and the interior of the wound dressing can be taken into account when estimating temperature of the actual wound. RFID devices with external temperature sensors accurate to approximately 2° C. are described (see e.g., Sample et al., "Design of an RFID-Based Battery-Free Programmable Sensing Platform," *IEEE Trans. Instr. Meas.* 57: 2608-2615, 2008 which is incorporated herein by reference). Methods to use temperature sensors to detect the presence of microbial infections are known. For example, a thermistor-based sensor is used to monitor the temperature of a wound and indicate the presence of an infection or normal wound healing (see e.g., U.S. Pat. No. 6,963,772 to Bloom et al. titled "User-Retainable Temperature and Impedance Monitoring Methods and Devices," which is incorporated herein by reference). An average temperature taken over time, or a graph showing temperature readings over time can be presented to a system user by the central assembly computing system.

To specifically detect *S. aureus* in the wound, a third sensor is connected to the microcontroller and inserted in a tube projecting into the wound dressing. A nano-cantilever device that signals electronically when it binds a *S. aureus* antigen is constructed using a carbon nanotube and a monoclonal antibody (see e.g., U.S. Pat. No. 7,612,424 to Espinosa and Ke titled "Nanoelectromechanical Bistable Cantilever Device," which is incorporated herein by reference). The nano-cantilever is functionalized with a monoclonal antibody specific for poly-N-acetylglucosamine (PNAG), a *S. aureus* antigen (see Kelly-Quintos et al., "Characterization of the Opsonic and Protective Activity Against *Staphylococcus aureus* of Fully Human Monoclonal Antibodies Specific for the Bacterial Surface Polysaccharide Poly-N-Acetylglucosamine" *Infection and Immunity* 74: 2742-2750 (2006) which is incorporated herein by reference). Signals from the nano-cantilever, moisture sensor and temperature sensor are received by the microcontroller and transmitted to the local unit via the integrated RFID reader.

The local unit transmits signals received from the appurtenance to the wound dressing to a central computer assembly that stores the data and alerts hospital caregivers if an infection is detected or the wound dressing needs attention. For example, if the patient's bandage appurtenance is interrogated by the RFID reader and the *S. aureus* sensor (i.e. nano-cantilever) signals that *S. aureus* antigen is detected in the wound dressing, the local unit including the RFID reader transmits the information to the central computer assembly that issues an alert (e.g., email) to the nurses and/or doctors attending to the patient. Moreover, the wound dressing data is stored in the patient's electronic health record. The local unit also has programs and circuitry to interrogate the bandage appurtenance according to a predetermined schedule and report back to the central computer assembly. The wound dressing appurtenance system interacts with healthcare personnel through the central computer assembly and records and stores information on the wound dressing, changes in the wound dressing, infections and wound healing. An individual user may query the system for information, and the system can be preset to report at a particular time (e.g. the start of the day, or the start of a medical work shift).

Example 5

An Individual with $2^{nd}$ Degree Burns on their Leg is Treated with Wound Dressings and a Wound Dressing Monitor System to Monitor the Moisture Level and Infection Status of the Burn Wounds An individual has suffered $2^{nd}$ degree burn wounds that cover approximately 200 cm² of the leg. Medical personnel have chosen an absorbent wound dressing which removes excess exudates but retains moisture in the wound. For example, an antimicrobial wound dressing (e.g., Mepilex® Ag available from Molnlycke Health Care US, LLC, Norcross, Ga.) is applied as an inner layer over the wound and a gauze dressing is applied as an absorbent outer layer to hold the inner layer dressing in place. To monitor the wound dressing, 3 bandage appurtenances are inserted approximately every 5 cm over the length of the wound site to monitor different areas of the burn wound. Each wound dressing appurtenance has a unique RFID identifier, a microcontroller, a moisture sensor and bacterial sensors. The placement and identification information for each appurtenance and the patient is read into the system with a local unit including an RFID reader at the time the wound dressing is placed on the patient's leg wound.

Each disposable wound dressing appurtenance includes a RFID device and a sensor with a microcontroller to direct sensing in the wound dressing. The system also includes a local unit configured to interrogate the wound dressing appurtenances and to communicate information to a central computer assembly for the wound monitoring system. A UHF RFID sensor device with a microcontroller and external sensors (see e.g., Sample et al., "Design of an RFID-Based Battery-Free Programmable Sensing Platform," *IEEE Trans. Instr. Meas.* 57: 2608-2615, 2008 which is incorporated herein by reference) is constructed with a plastic housing and projections which extend from the surface of the appurtenance into the wound dressing. A projection contains a moisture sensor. For example, a moisture sensor comprised of two electrodes which project into the wound dressing to reach the wound surface can be used to monitor the amount of fluids (e.g., exudate and blood) emanating from the wound. Electrode-based moisture sensors are used to correlate wound moisture levels and impedance in the sensor (see e.g., McColl et al., "Monitoring Moisture without Disturbing the Wound Dressing," *Wounds UK* 5: 94-99, 2009 which is incorporated herein by reference) and wound moisture levels are correlated with healing. For example, a rapid increase in moisture level may indicate a microbial infection is present (see e.g., U.S. Pat. No. 6,963,772 to Bloom et al. titled "User-Retainable Temperature and Impedance Monitoring Methods and Devices," which is incorporated herein by reference). Bacterial sensors to detect proteins specific to *Staphylococcus aureus* and *Pseudomonas aeruginosa*, pathogens which frequently infect burn wounds, are constructed within projections configured to extend into the wound dressing from the appurtenance surface. Information from these sensors is transmitted to the microcontroller. For example, a nano-cantilever device that signals electronically when it binds a *S. aureus* antigen is constructed using a carbon nanotube (see e.g., U.S. Pat. No. 7,612,424 to Espinosa and Ke titled "Nanoelectromechanical Bistable Cantilever Device," which is incorporated herein by reference). The nano-cantilever is functionalized with a monoclonal antibody specific for poly-N-acetylglucosamine (PNAG), a *S. aureus* antigen (see Kelly-Quintos et al., "Characterization of the Opsonic and Protective Activity Against *Staphylococcus aureus* of Fully Human Monoclonal Antibodies Specific for the Bacterial Surface Polysaccharide Poly-N-Acetylglucosamine" *Infection and Immunity* 74: 2742-2750 (2006) which is incorporated herein by reference). An equivalent nano-cantilever device to detect *P. aeruginosa* is constructed with a specific anti-P. aeruginosa monoclonal antibody (available from Abcam, San Francisco, Calif.). The bacterial sensors may project in different tubes or the same projection tube. When the sensors encounter bacterial antigens, a signal is transmitted to the microcontroller. A corresponding signal is then transmitted from the appurtenance to the local unit in response to a query signal from the local unit.

One part of the wound dressing becomes saturated with exudates fluid after 16 hours and the proximal moisture sensor in the appurtenance attached to that region of the wound dressing signals the local unit (programmed to interrogate the appurtenance every 4 hours) that the dressing is saturated. The local unit signals that a dressing needs attention with an LED light on the local unit and also sends a signal with information regarding the RFID identity, patient ID and moisture sensor data to a central computer assembly. The central computer assembly is configured to alert hospital personnel. The information is also automatically entered into the patient's electronic medical record by the central computer assembly.

A nurse responds to the central computer assembly alert which has been sent to the nursing station. The nurse physically inspects the wound dressing identified by the alert information. The saturated portion of the wound dressing is removed and disposed of, with the appurtenance still attached. The wound dressing is replaced and a new dressing appurtenance with a new RFID number and the patient's ID is inserted in the new wound dressing.

Example 6

Wound Dressing Appurtenance Used to Monitor a Wound Dressing on an Individual with a Venous Leg Ulcer An individual with a chronic wound, a venous leg ulcer, is treated in the patient's home with a wound dressing and a wound dressing appurtenance system to monitor the wound dressing and indicate when the dressing needs attention. Information regarding a series of wound dressings over time is also automatically saved into the patient's medical record for reference by medical personnel. The appurtenance system includes: a wound dressing appurtenance with a RFID sensor; a local unit with a RFID reader and a central computer assembly associated with the patient's clinic or hospital.

The patient's leg ulcer is treated in the patient's home by a nurse, who chooses a wound dressing including absorbent padding and a short stretch bandage (available from Activa Healthcare). The appurtenance is inserted into the dressing over the wound with a projection penetrating into the wound dressing. The appurtenance is fixed securely in place with adhesive on the flange of the device and by virtue of barbs on the outside of the appurtenance that affix it securely to the wound dressing.

The disposable appurtenance includes a programmable RFID sensor device. The appurtenance is constructed with a RFID tag on a printed circuit board with external sensors. For example, the appurtenance may contain a dipole antenna of 22-gauge copper magnet wire, a rectifier to convert incoming UHF energy into DC, a capacitor to store the energy, and a programmable microcontroller to perform sensing and computation (see e.g., Sample et al., "Design of an RFID-Based Battery-Free Programmable Sensing Platform," *IEEE Trans. Instr. Meas.* 57: 2608-2615, 2008 which is incorporated herein by reference). A moisture sensor comprised of two electrodes which project into the wound dressing can be used to monitor the amount of fluids (e.g., exudate and blood) emanating from the wound into the dressing. The electrode-based moisture sensor correlates moisture levels and impedance in the sensor (see e.g., McColl et al., *Wounds UK* 5: 94-99, 2009 which is incorporated herein by reference). Wound moisture levels are correlated with healing, and a rapid increase in moisture level, may indicate a microbial infection is present (see e.g., U.S. Pat. No. 6,963,772 issued to Bloom et al. on Nov. 8, 2005 which is incorporated herein by reference).

The nurse installs the appurtenance system in the patient's home to allow remote monitoring of the leg ulcer. After manually pushing the appurtenance into the wound dressing, a local unit is used to query the appurtenance for its unique identification code and then to monitor the appurtenance. A local unit including a mobile RFID reader is installed in the patient's home. For example, a long range RFID reader operating in the UHF band with an input/output interface for the internet is available from GAO RFID Inc. The local unit transmits UHF waves (e.g., approximately at 902-928 MHz) from the bedside, a chair, or a table (e.g., within 10-15 meters of the wound dressing with the affixed appurtenance). The local unit is programmed by the nurse using a laptop computer to enter the RFID number, patient identification, and schedule for appurtenance interrogation (e.g., every 2 hours). The nurse also establishes a link between the local unit and a central computer assembly affiliated with the hospital or clinic. For example, a link to the patient's internet service is established to transmit data from the local unit to the central computer assembly. Information from the local unit may also be configured to automatically be included in the patient's electronic health record by the central computer assembly.

If the moisture sensor of the appurtenance detects excess moisture in the wound dressing, an alert is signaled to the patient and the hospital's central computer. The local unit receives a signal of excess moisture (i.e., low impedance) from the moisture sensor in the appurtenance and an LED on the local unit alerts the patient or a family member that the wound dressing needs attention. Also the local unit transmits the signal of excess moisture to the central computer assembly where an alert (e.g., an e-mail) is created for the nurses on duty.

The nurse receiving the alert can contact the patient and/or the patient can phone the nurse when the LED on the local unit lights up. The nurse can recommend the patient change the dressing or visit the patient to change the dressing and inspect the wound directly. The nurse, the patient or another caregiver can change the dressing and insert a new appurtenance in the dressing over the wound site. The new dressing appurtenance is verified by interrogating the new appurtenance with the local unit and the information is sent to the central computer assembly.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for monitoring a wound dressing, comprising:
an appurtenance to the wound dressing distinct from the wound dressing, wherein the appurtenance includes an appurtenance surface positioned and configured to abut and adhesively attach to an outer surface of the wound dressing, the appurtenance includes one or more projections that project from the appurtenance surface and are configured to pierce into the wound dressing, the one or more projections further configured to sample a fluid associated with a wound, a processor, and at least one transmitter operably attached to the processor;
one or more sensors configured to sense at least one characteristic of the wound dressing;

a selectively actuated switch configured to allow the at least one transmitter to transmit a signal in response to the one or more sensors sensing the at least one characteristic; and a local unit including a receiver for the at least one transmitter, at least one processor operably attached to the receiver, and at least one communication unit operably attached to the processor.

2. The system of claim 1, wherein
the one or more sensors are operably attached to the processor.

3. The system of claim 1, wherein the one or more projections of the appurtenance comprise:
one or more fluid conduits between an interior of the wound dressing and the appurtenance.

4. The system of claim 1, wherein the at least one transmitter included in the appurtenance comprises:
a radio-frequency identification (RFID) transmitter.

5. The system of claim 1, wherein the at least one transmitter included in the appurtenance comprises:
a near field communication (NFC) device.

6. The system of claim 1, wherein the appurtenance comprises:
at least one antenna.

7. The system of claim 1, wherein the appurtenance comprises:
a receiver.

8. The system of claim 1, wherein the appurtenance comprises:
at least one indicator.

9. The system of claim 1, wherein the local unit comprises:
a radio-frequency identification (RFID) receiver.

10. The system of claim 1, wherein the local unit comprises:
a near field communication (NFC) device.

11. The system of claim 1, wherein the local unit comprises:
at least one user interface.

12. The system of claim 1, wherein the local unit is configured to communicate with a remote system.

13. The system of claim 1, wherein the local unit is of a size, a shape and a configuration for portable handheld use.

14. The system of claim 1, wherein the at least one communication unit comprises at least one of: a visual display, a sound generator, a vibrating unit, and one or more light displays.

15. The system of claim 1, wherein the at least one communication unit comprises:
at least one transmitter.

16. A system for monitoring a wound dressing, comprising:
an appurtenance to the wound dressing distinct from the wound dressing that includes an appurtenance surface positioned and configured to abut and adhesively attach to an outer surface of the wound dressing, a substrate, a transmission unit, a selectively activated switch, and a projection projecting from the appurtenance surface wherein the projection has a size and shape configured to pierce the outer surface of the wound dressing, extend into an interior region of the wound dressing, and sample a fluid associated with a wound;

a local unit, including a receiver configured to receive signals from the transmission unit including information related to the wound or wound dressing, a transmitter configured to send signals to the transmission unit, a processor, nonvolatile memory, and a power source; and a central assembly, including a processor, a receiver configured to receive signals from the local unit including the information related to the wound or wound dressing, and at least one user interface, the processor configured to determine a suggested response to be taken by a caregiver based at least partially based on the information.

17. The system of claim 16, wherein the transmission unit of the appurtenance comprises:
a radio frequency identification (RFID) unit.

18. The system of claim 16, wherein the transmission unit of the appurtenance comprises:
a near field communication (NFC) device.

19. The system of claim 16, wherein the transmission unit of the appurtenance comprises:
at least two antennas.

20. The system of claim 16, wherein the selectively activated switch is a binary switch.

21. The system of claim 16, wherein the selectively activated switch comprises:
a conduit configured to permit a flow of the fluid from the interior region of the wound dressing through the projection and into a location adjacent to the transmission unit.

22. The system of claim 16, wherein the projection comprises:
a substantially hollow structure.

23. The system of claim 16, wherein the local unit comprises:
a radio frequency identification (RFID) device.

24. The system of claim 16, wherein the local unit comprises:
a user interface.

25. The system of claim 16, wherein the local unit comprises:
an auditory signal generator.

26. The system of claim 16, wherein the local unit comprises:
a communication device configured to send the signals to the central assembly.

27. The system of claim 16, wherein the local unit is configured to send and receive signals from a plurality of appurtenances.

28. The system of claim 16, wherein the central assembly comprises:
a transmitter configured to send signals to the local unit.

29. The system of claim 16, wherein the central assembly comprises:
a transmitter configured to send signals to one or more mobile devices.

30. The system of claim 16, wherein the receiver of the central assembly is configured to receive signals from a plurality of local units.

31. The system of claim 16, wherein the central assembly comprises:
a transmitter configured to send signals to a plurality of local units.

32. A system for monitoring a wound dressing, comprising:
an appurtenance to the wound dressing distinct from the wound dressing that includes an appurtenance surface positioned and configured to abut and adhesively attach to an outer surface of the wound dressing, a substrate, a transmission unit, a selectively activated switch, and a projection projecting from the appurtenance surface wherein the projection has a size and shape configured to pierce the outer surface of the wound dressing, extend into an interior region of the wound dressing a selected depth, and sample a fluid associated with a wound;

a local unit, including a receiver unit configured to receive signals from the transmission unit including information related to the wound or wound dressing, a transmitter configured to send signals to the transmission unit, a processor, nonvolatile memory, and a power source;

a central assembly, including a processor, a receiver configured to receive signals from the local unit including the information related to the wound or wound dressing, a transmitter, and at least one user interface, the processor configured to determine a suggested response to be taken by a caregiver based at least partially based on the information, wherein the suggested response is for the caregiver to physically check the wound dressing; and one or more user indicator devices including a receiver configured to receive signals from the central assembly, a processor, nonvolatile memory, and an indicator configured to indicate the suggested response responsive to receiving the signals from the central assembly.

33. The system of claim 32, wherein the transmission unit of the appurtenance comprises:

a radio frequency identification (RFID) unit.

34. The system of claim 32, wherein the transmission unit of the appurtenance comprises:

a near field communication (NFC) device.

35. The system of claim 32, wherein the transmission unit of the appurtenance comprises:

at least two antennas.

36. The system of claim 32, wherein the selectively activated switch is a binary switch.

37. The system of claim 32, wherein the selectively activated switch comprises:

a conduit configured to permit a flow of the fluid from the interior region of the wound dressing through the projection and into a region of the appurtenance adjacent to the transmission unit.

38. The system of claim 32, wherein the projection comprises:

a substantially hollow structure.

39. The system of claim 32, wherein the appurtenance comprises:

at least one sensor configured to respond to a substance within the wound dressing and communicate a response to the selectively activated switch.

40. The system of claim 32, wherein the local unit comprises:

a radio frequency identification (RFID) device.

41. The system of claim 32, wherein the local unit comprises:

a near field communication (NFC) device.

42. The system of claim 32, wherein the local unit comprises:

an auditory signal generator.

43. The system of claim 32, wherein the local unit comprises:

a communication device configured to send the signals to the central assembly and receive signals from the central assembly.

44. The system of claim 32, wherein the local unit is configured to send and receive signals from a plurality of appurtenances.

45. The system of claim 32, wherein the central assembly comprises:

a transmitter configured to send signals to one or more mobile devices.

46. The system of claim 32, wherein the receiver of the central assembly is configured to receive signals from a plurality of local units.

47. The system of claim 32, wherein the central assembly comprises:

a receiver configured to interact with a computer system.

* * * * *

UNITED STATES PATENT AND TRADEMARK OFFICE
CERTIFICATE OF CORRECTION

PATENT NO. : 9,084,530 B2  Page 1 of 1
APPLICATION NO. : 13/445220
DATED : July 21, 2015
INVENTOR(S) : Duesterhoft et al.

It is certified that error appears in the above-identified patent and that said Letters Patent is hereby corrected as shown below:

In the Claims

Column 53, Line 67, Claim 16:
"processor, nonvolatile memory, and a power source; and" should be
-- processor, non-volatile memory, and a power source; and --

Column 54, Line 6, Claim 16:
"caregiver based at least partially based on the information" should be
-- caregiver at least partially based on the information --

Column 55, Line 7, Claim 32:
"processor, nonvolatile memory, and a power source; and" should be
-- processor, non-volatile memory, and a power source; and --

Column 55, Line 13, Claim 32:
"taken by a caregiver based at least partially based on the . . ." should be
-- taken by a caregiver at least partially based on the . . . --

Column 55, Line 18, Claim 32:
"a processor, nonvolatile memory, and an indicator. . ." should be
-- a processor, non-volatile memory, and an indicator. . . --

Signed and Sealed this
Twenty-first Day of June, 2016

Michelle K. Lee
*Director of the United States Patent and Trademark Office*